(12) United States Patent
Milne et al.

(10) Patent No.: US 8,969,354 B2
(45) Date of Patent: Mar. 3, 2015

(54) FATTY ACID FUMARATE DERIVATIVES AND THEIR USES

(71) Applicants: Jill C. Milne, Brookline, MA (US); Michael R. Jirousek, Cambridge, MA (US); Jean E. Bemis, Arlington, MA (US); Chi B. Vu, Arlington, MA (US)

(72) Inventors: Jill C. Milne, Brookline, MA (US); Michael R. Jirousek, Cambridge, MA (US); Jean E. Bemis, Arlington, MA (US); Chi B. Vu, Arlington, MA (US)

(73) Assignee: Catabasis Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/673,588

(22) Filed: Nov. 9, 2012

(65) Prior Publication Data

US 2013/0065909 A1 Mar. 14, 2013

Related U.S. Application Data

(63) Continuation of application No. 12/986,713, filed on Jan. 7, 2011, now abandoned.

(60) Provisional application No. 61/293,396, filed on Jan. 8, 2010, provisional application No. 61/294,578, filed on Jan. 13, 2010.

(51) Int. Cl.
*A61K 31/4965* (2006.01)
*A61K 31/40* (2006.01)
(Continued)

(52) U.S. Cl.
CPC ............ *C07D 207/40* (2013.01); *C07C 233/49* (2013.01); *C07D 295/18* (2013.01); *C07C 233/38* (2013.01); *A61K 47/481* (2013.01); *C07D 241/04* (2013.01); *C07D 339/04* (2013.01); *C07C 323/41* (2013.01); *C07C 233/20* (2013.01)
USPC ...... 514/255.01; 514/563; 514/440; 514/425; 514/546; 554/58; 554/42; 544/387; 548/544; 549/39

(58) Field of Classification Search
CPC .. A61K 47/481; C07C 233/20; C07C 233/38; C07C 233/49; C07C 323/41; C07D 207/40; C07D 241/04; C07D 295/18; C07D 339/04
USPC .............. 554/42, 58; 514/255, 425, 440, 546, 514/563; 544/387; 548/544; 549/39
See application file for complete search history.

(56) References Cited

U.S. PATENT DOCUMENTS 5,242,905 A * 9/1993 Blank ........................ 514/18.6
5,798,389 A * 8/1998 Kanayama et al. ........... 514/560
(Continued)

FOREIGN PATENT DOCUMENTS

WO WO-97/44063 A2 11/1997
WO WO-2008/097596 A2 8/2008

OTHER PUBLICATIONS

Office Action for Chinese Application No. 201180012336.4 mailed Aug. 19, 2013 (5 pages).
(Continued)

*Primary Examiner* — Deborah D Carr
(74) *Attorney, Agent, or Firm* — Goodwin Procter LLP

(57) ABSTRACT

The invention relates to Fatty Acid Fumarate Derivatives; compositions comprising an effective amount of a Fatty Acid Fumarate Derivative; and methods for treating or preventing cancer, a metabolic disorder or neurodegenerative disorder comprising the administration of an effective amount of a Fatty Acid Fumarate Derivative.

33 Claims, 4 Drawing Sheets

(51) Int. Cl.

| | |
|---|---|
| *C07C 233/00* | (2006.01) |
| *C07D 295/00* | (2006.01) |
| *C07D 207/00* | (2006.01) |
| *C07D 339/02* | (2006.01) |
| *C07C 233/49* | (2006.01) |
| *C07D 295/18* | (2006.01) |
| *C07C 233/38* | (2006.01) |
| *C07D 207/40* | (2006.01) |
| *A61K 47/48* | (2006.01) |
| *C07D 241/04* | (2006.01) |
| *C07D 339/04* | (2006.01) |
| *C07C 323/41* | (2006.01) |
| *C07C 233/20* | (2006.01) |

(56) References Cited

U.S. PATENT DOCUMENTS 6,387,945 B2    5/2002  Packer et al.
6,956,059 B2 *  10/2005 Coupland .................... 514/613
2011/0172240 A1  7/2011  Milne et al.

OTHER PUBLICATIONS

International Search Report and Written Opinion for International Application No. PCT/US2011/020534, mailed Mar. 10, 2011, 7 pages.

Supplementary European Search Report and Search Opinion for EP 11732212.3 dated Mar. 31, 2014 (7 pages).

* cited by examiner

FATTY ACID FUMARATE DERIVATIVES AND THEIR USES

PRIORITY CLAIM

This application is a continuation application of U.S. patent application Ser. No. 12/986,713 filed Jan. 7, 2011, which claims priority to U.S. Provisional Application 61/293,396 filed Jan. 8, 2010, and U.S. Provisional Application 61/294,578, filed Jan. 13, 2010, the entire disclosures of which are relied upon and incorporated into this application by reference for all purposes.

FIELD OF THE INVENTION

The invention relates to Fatty Acid Fumarate Derivatives; compositions comprising an effective amount of a Fatty Acid Fumarate Derivative; and methods for treating or preventing cancer, and metabolic, autoimmune or neurodegenerative disorders, comprising the administration of an effective amount of a Fatty Acid Fumarate Derivative. All patents, patent applications, and publications cited herein are hereby incorporated by reference in their entireties.

BACKGROUND OF THE INVENTION

Oily cold water fish, such as salmon, trout, herring, and tuna are the source of dietary marine omega-3 fatty acids, with eicosapentaenoic acid (EPA) and docosahexaenoic acid (DHA) being the key marine derived omega-3 fatty acids. Omega-3 fatty acids have previously been shown to improve insulin sensitivity and glucose tolerance in normoglycemic men and in obese individuals. Omega-3 fatty acids have also been shown to improve insulin resistance in obese and non-obese patients with an inflammatory phenotype. Lipid, glucose, and insulin metabolism have been shown to improve in overweight hypertensive subjects through treatment with omega-3 fatty acids. Omega-3 fatty acids (EPA/DHA) have also been shown to decrease triglycerides and to reduce the risk for sudden death caused by cardiac arrhythmias in addition to improve mortality in patients at risk of a cardiovascular event. Omega-3 fatty acids have also been taken as dietary supplements part of therapy used to treat dyslipidemia, and anti-inflammatory properties. A higher intake of omega-3 fatty acids lower levels of circulating TNF-α and IL-6, two of the cytokines that are markedly increased during inflammation processes (Chapkin et al, *Prostaglandins, Leukot Essent Fatty Acids* 2009, 81, p. 187-191; Duda et al, *Cardiovasc Res* 2009, 84, p. 33-41). In addition, a higher intake of omega-3 fatty acids has been shown to increase levels of the well-characterized anti-inflammatory cytokine IL-10 (Bradley et al, *Obesity* (Silver Spring) 2008, 16, p. 938-944). A recent study (Wang et al, *Molecular Pharmaceutics* 2010, 7, p. 2185-2193) has demonstrated that DHA could also induce the Nrf2 and the Nrf2-target gene Heme-oxygenase 1 (HO-1) and this pathway could play a significant role in suppressing LPS-mediated inflammation.

Both DHA and EPA are characterized as long chain fatty acids (aliphatic portion between 12-22 carbons). Medium chain fatty acids are characterized as those having the aliphatic portion between 6-12 carbons. Lipoic acid is a medium chain fatty acid found naturally in the body. It plays many important roles such as free radical scavenger, chelator to heavy metals and signal transduction mediator in various inflammatory and metabolic pathways, including the NF-κB pathway (Shay, K. P. et al. *Biochim. Biophys. Acta* 2009, 1790, 1149-1160). Lipoic acid has been found to be useful in the treatment of a number of chronic diseases that are associated with oxidative stress (for a review see Smith, A. R. et al *Curr. Med. Chem.* 2004, 11, p. 1135-46). Lipoic acid has now been evaluated in the clinic for the treatment of diabetes (Morcos, M. et al *Diabetes Res. Clin. Pract.* 2001, 52, p. 175-183) and diabetic neuropathy (Mijnhout, G. S. et al *Neth. J. Med.* 2010, 110, p. 158-162). Lipoic acid has also been found to be potentially useful in treating cardiovascular diseases (Ghibu, S. et al, *J. Cardiovasc. Pharmacol.* 2009, 54, p. 391-8), Alzheimer's disease (Maczurek, A. et al, *Adv. Drug Deliv. Rev.* 2008, 60, p. 1463-70) and multiple sclerosis (Yadav, V. *Multiple Sclerosis* 2005, 11, p. 159-65; Salinthone, S. et al, *Endocr. Metab. Immune Disord. Drug Targets* 2008, 8, p. 132-42).

Fumaric acid and its ester derivatives, either the mono alkyl hydrogen fumarates or dialkyl fumarates, have been used as therapeutic agents for the treatment of psoriasis, an autoimmune and Th1-mediated skin disease (Altmeyer et al, *J. of the American Academy of Dermatology* 1994, 30, p. 977-981). In clinical studies with psoriasis patients that have been administered with fumarates, a reduction of peripheral CD4+ and CD8+-T lymphocytes has been observed. These agents have been reported to inhibit LPS-induced NF-κB activation in dendritic cells and endothelial cells in vitro (Loewe et al., *J. Immunol.* 2004, 168, 4781-4787; Litjens et al., *Eur. J. Immunol.* 2004, 34, 565-575). Dialkyl and monoalkyl fumarates have also demonstrated oral efficacy in the chronic experimental autoimmune encephalomyelitis (EAE) mouse model for multiple sclerosis (MS). In this particular model, C57BL/6 mice were challenged with the immunopeptide MOG 35-55 in order to induce disabilities that were equivalent to those exhibited by MS patients. Oral treatment with either dialkyl or monoalkyl fumarate resulted in a significant improvement in the disability score. The anti-inflammatory cytokine IL-10 was particularly elevated in the blood among the animals treated with either dialkyl or monoalkyl fumarate. Furthermore, histological analysis of the spinal cord of animals treated with either dialkyl or monoalkyl fumarate showed a strongly reduced macrophage inflammation (Schilling et al., *Clinical and Experimental Immunology* 2006, 145, 101-107). Dialkyl and monoalkyl fumarate esters have also been used in a number of reported studies with patients exhibiting the relapsing-remitting form of multiple sclerosis. Patients treated with 720 mg of fumarate esters daily for 70 weeks exhibited a significant reduction in inflammatory brain lesions, as noted by the reduction of new gadolinium-enhancing (Gd+) lesions in various MRI taken during the course of the treatment (Schimrigk et al., *Eur. J. Neurology* 2006, 13, 604-610). More recently, fumarates have been shown to activate Nrf2, a transcription factor that is responsible for the induction of a number of important antioxidants and detoxification enzymes that protect mammalian cells against reactive oxygen/nitrogen species and electrophiles (Lukashev, M. E. "Nrf2 screening assays and related methods and compositions" WO 08097596 A2; Wilms et al, *Journal of Neuroinflammation* 2010, 7:30).

Chronic oxidative stress and inflammation have now been linked to the development and progression of a number of debilitating diseases beyond multiple sclerosis. Some of these diseases include renal failure, heart failure, atherosclerosis, osteoporosis, cancer, chronic obstructive pulmonary disease (COPD), Parkinson's disease and Alzheimer's disease. Activation of the Nrf2 pathway in order to resolve this chronic oxidative stress and inflammation appears to be a particularly promising new therapeutic approach (For a review see Gozzelino, R. et al *Annu. Rev. Pharmacol. Toxicol.* 2010, 50, p. 323-54). For instance, small molecule activators of Nrf2 have now been shown to be effective in the cisplatin-induced nephrotoxicity mouse model (Aleksunes et al, *J. Pharmacology & Experimental Therapeutics* 2010, 335, p. 2-12), the transgenic Tg19959 mouse model of Alzheimer's disease (Dumont et al, *J. Neurochem.* 2009, 109, p. 502-12), the mouse model for COPD (Sussan, T. E. et al *Proc. Natl. Acad. Sci. USA* 2009, 106, p. 250-5), and the murine 4T1 breast tumor model (Ling, X. et al *Cancer Res.* 2007, 67, p. 4210-8).

The ability to provide the effects of fatty acids and fumarates in a synergistic way would provide benefits in treating a variety of cancer, metabolic, autoimmune and neurodegenerative diseases.

SUMMARY OF THE INVENTION

The invention is based in part on the discovery of Fatty Acid Fumarate Derivatives and their demonstrated effects in achieving improved treatment that cannot be achieved by administering fumarates or fatty acids alone or in combination. These novel compounds are useful in the treatment or prevention of metabolic disorders including atherosclerosis, dyslipidemia, coronary heart disease, hypercholesterimia, Type 2 diabetes, elevated cholesterol, metabolic syndrome, diabetic nephropathy, IgA nephropathy, chronic kidney disease (CKD) and cardiovascular disease. In addition, they are useful in the treatment of autoimmune diseases such as rheumatoid arthritis, psoriasis, systemic lupus erythematosus, inflammatory bowel diseases (including colitis and Crohn's disease), respiratory diseases such as asthma, cystic fibrosis, COPD and neurodegenerative diseases such as multiple sclerosis, Parkinson's disease and Alzheimer's disease, Huntington's disease, amyotrophic lateral sclerosis (ALS) and muscular dystrophy. The compounds described herein are also useful in treating a variety of cancer such as carcinoma, sarcoma, lymphoma, leukemia, melanoma, mesothelioma, multiople myeloma, seminoma, and cancer of the bladder, blood, bone, brain, breast, central nervous system, colon, endometrium, esophagus, genitourinary tract, head, larynx, liver, lung, neck, ovary, pancreas, prostate, testicle, spleen, small intestine, large intestine or stomach.

Accordingly in one aspect, a molecular conjugate is described which comprises a fumarate and a fatty acid wherein the fatty acid is selected from the group consisting of omega-3 fatty acids, fatty acids that are metabolized in vivo to omega-3 fatty acids, and lipoic acid, and the conjugate is capable of hydrolysis to produce free fumarate and free fatty acid. In some embodiments, the fatty acid is selected from the group consisting of all-cis-7,10,13-hexadecatrienoic acid, α-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid, tetracosahexaenoic acid and lipoic acid. In other embodiments, the fatty acid is selected from eicosapentaenoic acid, docosahexaenoic acid and lipoic acid. In some embodiments, the hydrolysis is enzymatic.

In another aspect, compounds of the Formula I and Formula II are described:

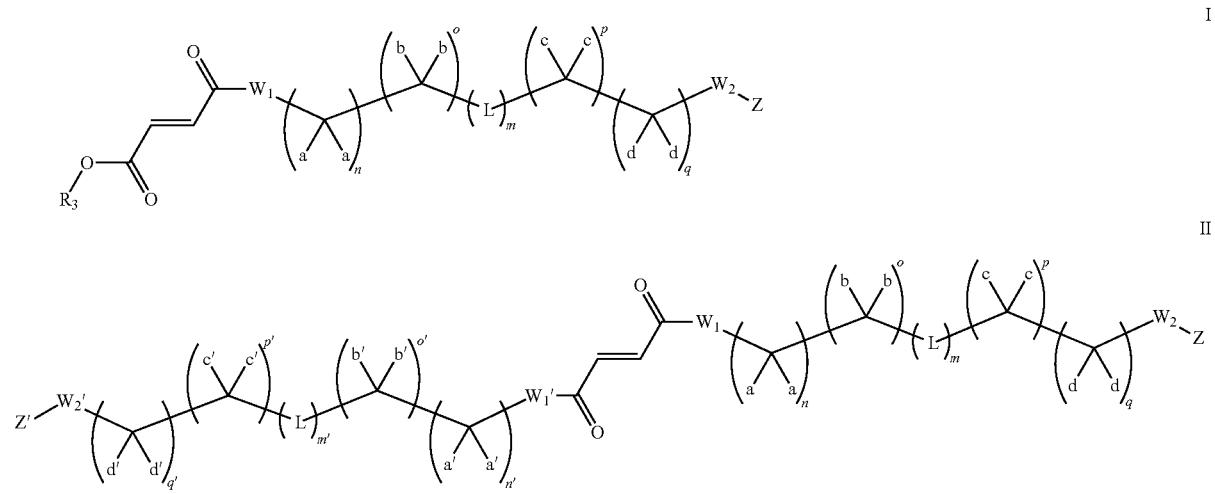

and pharmaceutically acceptable salts, hydrates, solvates, prodrugs, enantiomers, and stereoisomers thereof;

wherein each $W_1$, $W_2$, $W_1'$, and $W_2'$ is independently null, O, S, NH, or NR, or $W_1$ and $W_2$, or $W_1'$ and $W_2'$ can be taken together to form an optionally substituted imidazolidine or piperazine group;

each a, b, c, d, a', b', c', and d' is independently —H, -D, —CH$_3$, —OCH$_3$, —OCH$_2$CH$_3$, —C(O)OR, —O—Z, or benzyl, or two of a, b, c, and d or any two of a', b', c', and d' can be taken together, along with the single carbon to which they are bound, to form a cycloalkyl or heterocycle;

each n, o, p, q, n', o', p', and q' is independently 0, 1, or 2;

each L and L' is independently null, —O—, —C(O)—, —S—, —S(O)—, —S(O)$_2$—, —S—S—, —(C$_1$-C$_6$ alkyl)-, —(C$_3$-C$_6$ cycloalkyl)-, a heterocycle, a heteroaryl,

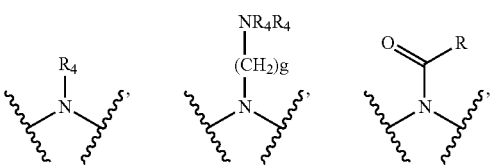

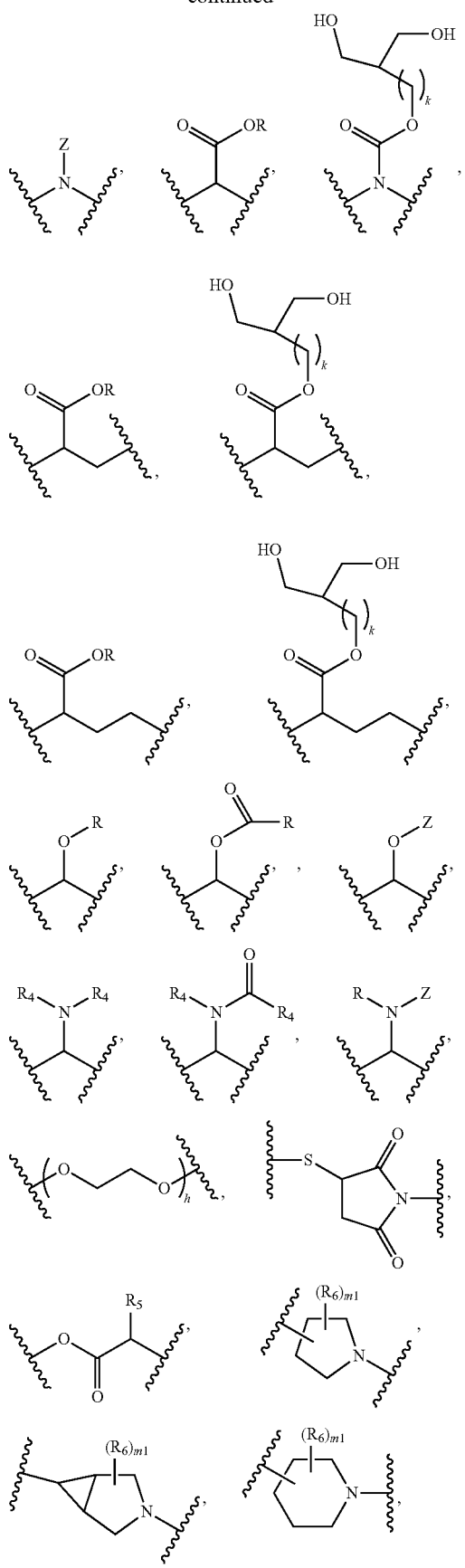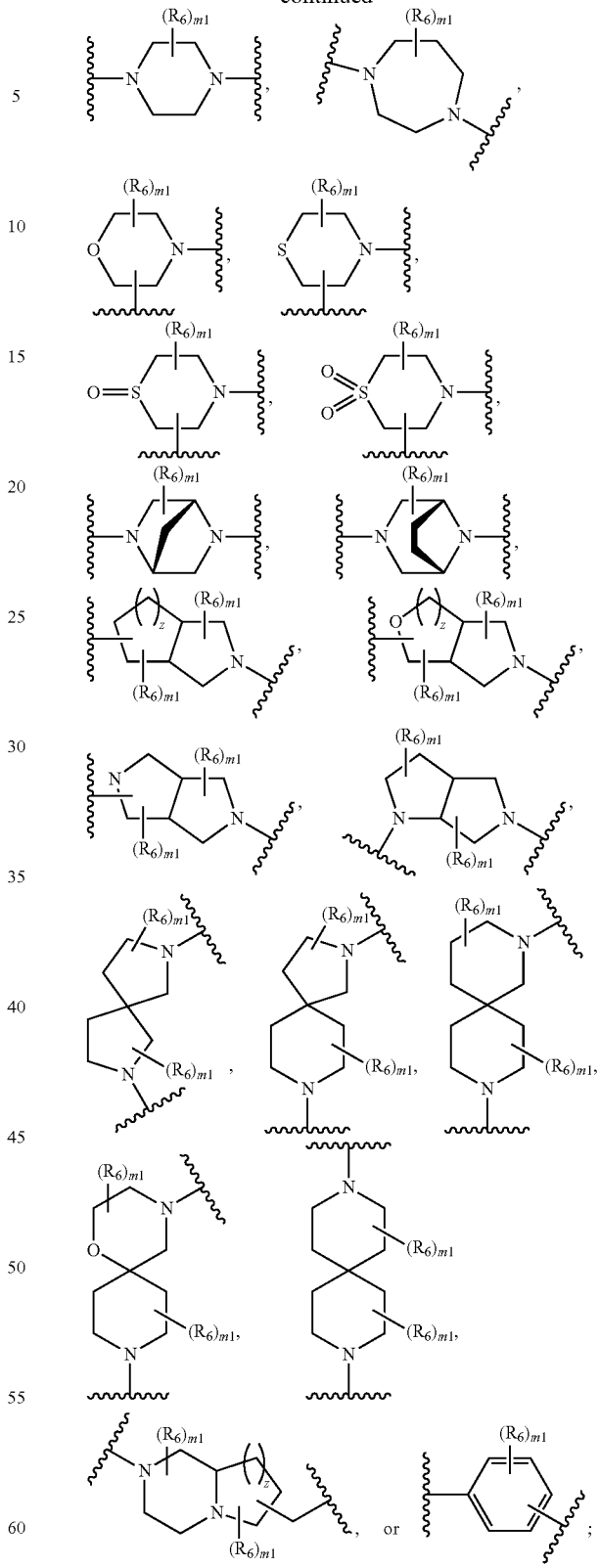
wherein the representation of L and L' is not limited directionally left to right as is depicted, rather either the left side or the right side of L and L' can be bound to the $W_1$ or $W_1$' side of the compound of Formula I or Formula II, respectively;

each $R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each g is independently 2, 3, or 4;
each h is independently 1, 2, 3, or 4;
each m and m' is independently 0, 1, 2, or 3; if m or m' is more than 1, then L or L'can be the same or different;
each m1 is independently 0, 1, 2, or 3;
k is 0, 1, 2, or 3;
z is 1, 2, or 3;
each $R_4$ is independently H or optionally substituted $C_1$-$C_6$ alkyl, wherein a methylene unit of the $C_1$-$C_6$ alkyl can be optionally substituted for either O or NR, and in $NR_4R_4$, both $R_4$ when taken together with the nitrogen to which they are attached can form a heterocyclic ring such as a pyrrolidine, piperidine, morpholine, piperazine or pyrrole;
each Z and Z' is independently H,

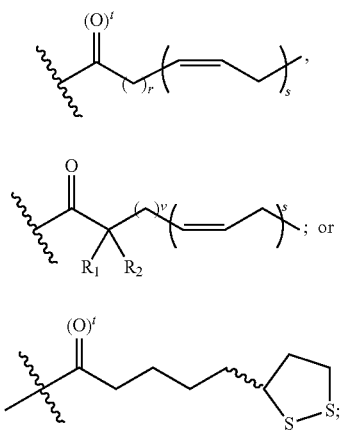

provided that
there is at least one

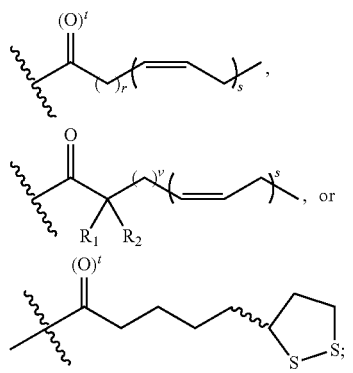

in the compound;
each t is independently 0 or 1;
each r is independently 2, 3, or 7;
each s is independently 3, 5, or 6;
each v is independently 1, 2, or 6;

each $R_1$ and $R_2$ is independently —H, -D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each $R_3$ is independently H, —$C_1$-$C_6$ alkyl or —C($CH_2$OH)$_2$;

each $R_5$ is independently e, H or straight or branched $C_1$-$C_{10}$ alkyl which can be optionally substituted with OH, $NH_2$, $CO_2$R, $CONH_2$, phenyl, $C_6H_4$OH, imidazole or arginine;

each e is independently H or any one of the side chains of the naturally occurring amino acids;

each R is independently —H or straight or branched $C_1$-$C_4$ alkyl optionally substituted with OH or halogen;

provided that
when each of m, n, o, p, and q, is 0, $W_1$ and $W_2$ is each null, and Z is

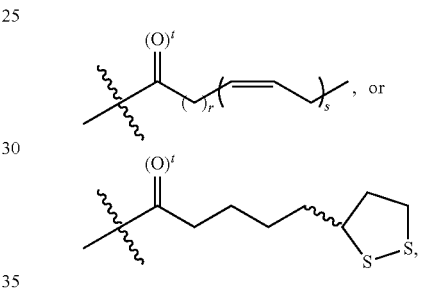

then t must be 0;
when each of m', n', o', p', and q', is 0, $W_1$' and $W_2$' is each null, and Z' is

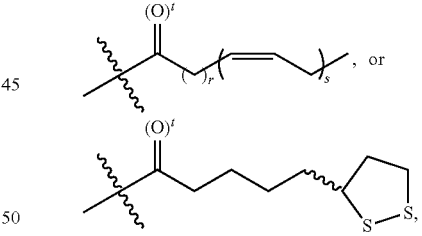

then t must be 0; and
when each of m, n, o, p, and q is 0, and $W_1$ and $W_2$ is each null, or when each of m', n', o', p', and q', is 0, $W_1$' and $W_2$' is each null, then Z or Z' must not be

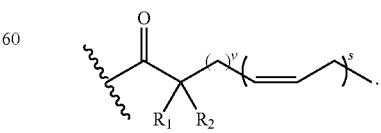

In another aspect, compounds of the Formula IA are described:

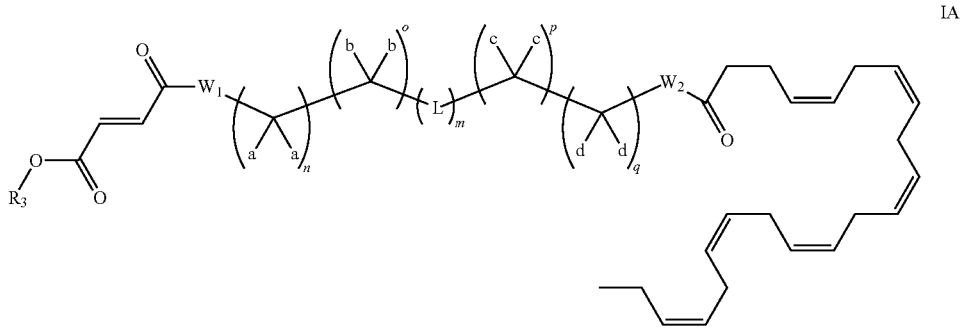

and pharmaceutically acceptable salts, hydrates, solvates, prodrugs, enantiomers, and stereoisomers thereof;

wherein each $W_1$ and $W_2$ is independently null, O, S, NH, or NR, or $W_1$ and $W_2$ can be taken together to form an optionally substituted imidazolidine or piperazine group;

each a, b, c, and d is independently —H, -D, —CH$_3$, —OCH$_3$, —OCH$_2$CH$_3$, —C(O)OR, or benzyl, or two of a, b, c, and d can be taken together, along with the single carbon to which they are bound, to form a cycloalkyl or heterocycle;

each n, o, p, and q is independently 0, 1, or 2;

each L is independently null, —O—, —C(O)—, —S—, —S(O)—, —S(O)$_2$—, —S—S—, —(C$_1$-C$_6$ alkyl)-, —(C$_3$-C$_6$ cycloalkyl)-, a heterocycle, a heteroaryl,

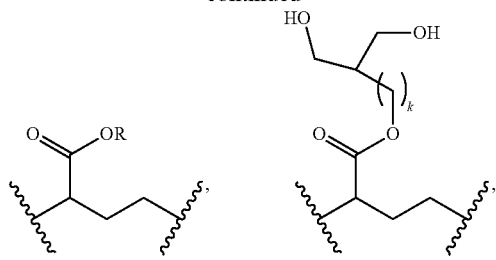

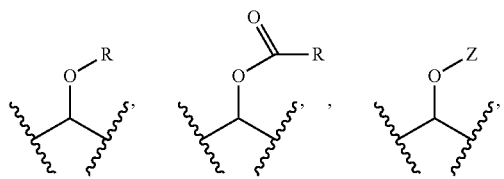

-continued

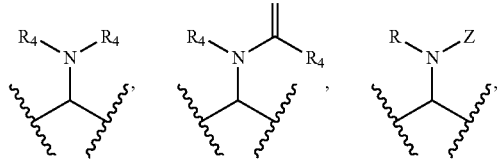

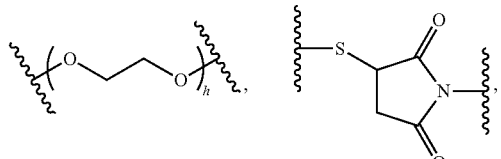

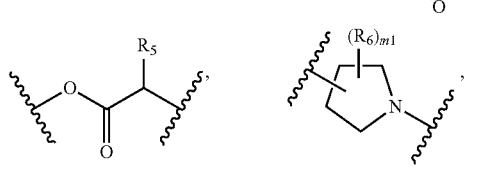

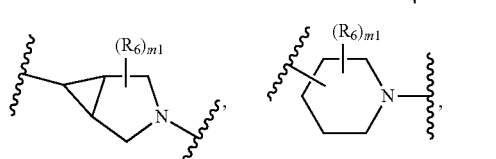

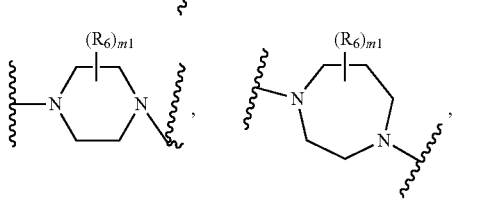

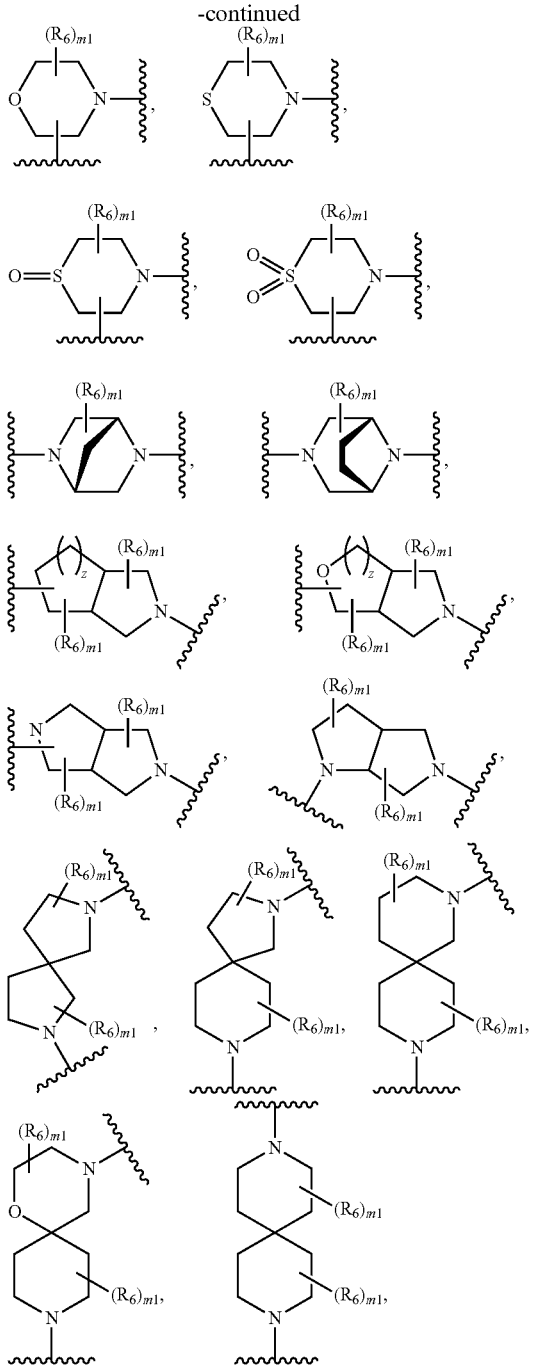

wherein the representation of L is not limited directionally left to right as is depicted, rather either the left side or the right side of L can be bound to the $W_1$ side of the compound of Formula IA;

each $R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each g is independently 2, 3, or 4;

each h is independently 1, 2, 3, or 4; each m is independently 0, 1, 2, or 3; if m is more than 1, then L can be the same or different;

each m1 is independently 0, 1, 2, or 3;

k is 0, 1, 2, or 3;

z is 1, 2, or 3;

each $R_4$ is independently H or optionally substituted $C_1$-$C_6$ alkyl, wherein a methylene unit of the $C_1$-$C_6$ alkyl can be optionally substituted for either O or NR, and in $NR_4R_4$, both $R_4$ when taken together with the nitrogen to which they are attached can form a heterocyclic ring such as a pyrrolidine, piperidine, morpholine, piperazine or pyrrole;

each $R_3$ is independently H, —$C_1$-$C_6$ alkyl or —C($CH_2$OH)$_2$;

each $R_5$ is independently e, H or straight or branched $C_1$-$C_{10}$ alkyl which can be optionally substituted with OH, $NH_2$, $CO_2$R, $CONH_2$, phenyl, $C_6H_4$OH, imidazole or arginine;

each e is independently H or any one of the side chains of the naturally occurring amino acids;

each R is independently —H, or straight or branched $C_1$-$C_4$ alkyl optionally substituted with OH, or halogen.

In another aspect, compounds of Formula IB are described:

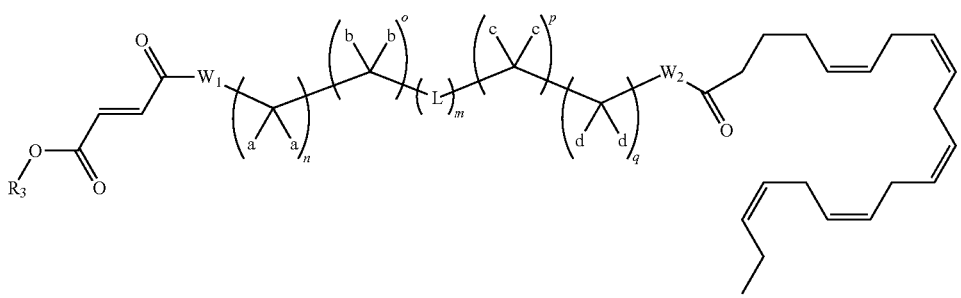

IB and pharmaceutically acceptable salts, hydrates, solvates, prodrugs, enantiomers, and stereoisomers thereof;

wherein each $W_1$ and $W_2$ is independently null, O, S, NH, or NR, or $W_1$ and $W_2$ can be taken together can form an optionally substituted imidazolidine or piperazine group;

each a, b, c, and d is independently —H, -D, —CH$_3$, —OCH$_3$, —OCH$_2$CH$_3$, —C(O)OR, or benzyl, or two of a, b, c, and d can be taken together, along with the single carbon to which they are bound, to form a cycloalkyl or heterocycle;

each n, o, p, and q is independently 0, 1, or 2;

each L is independently null, —O—, —C(O)—, —S—, —S(O)—, —S(O)$_2$—, —S—S—, —(C$_1$-C$_6$ alkyl)-, —(C$_3$-C$_6$ cycloalkyl)-, a heterocycle, a heteroaryl,

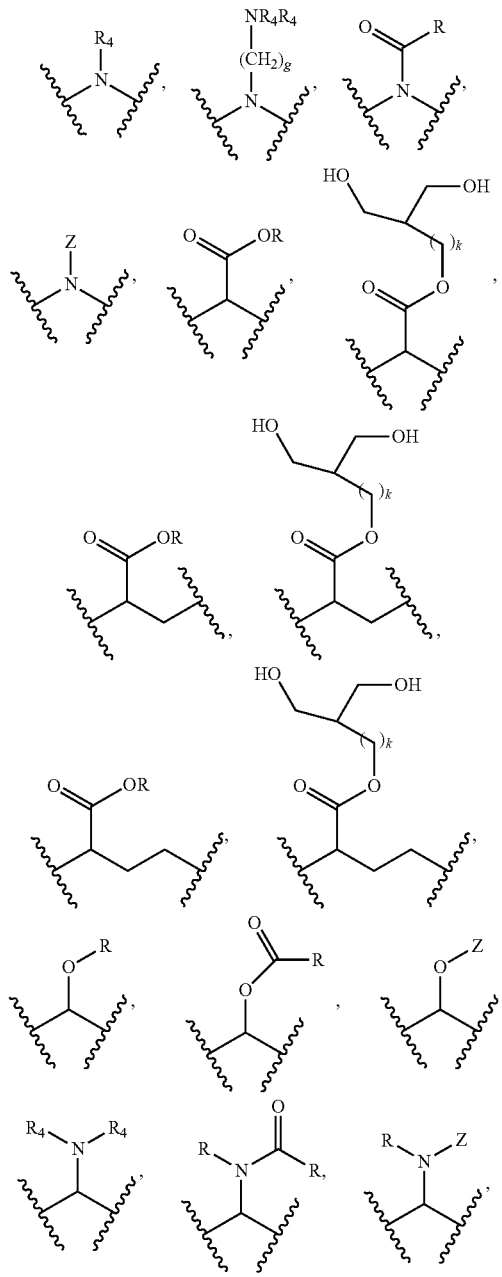

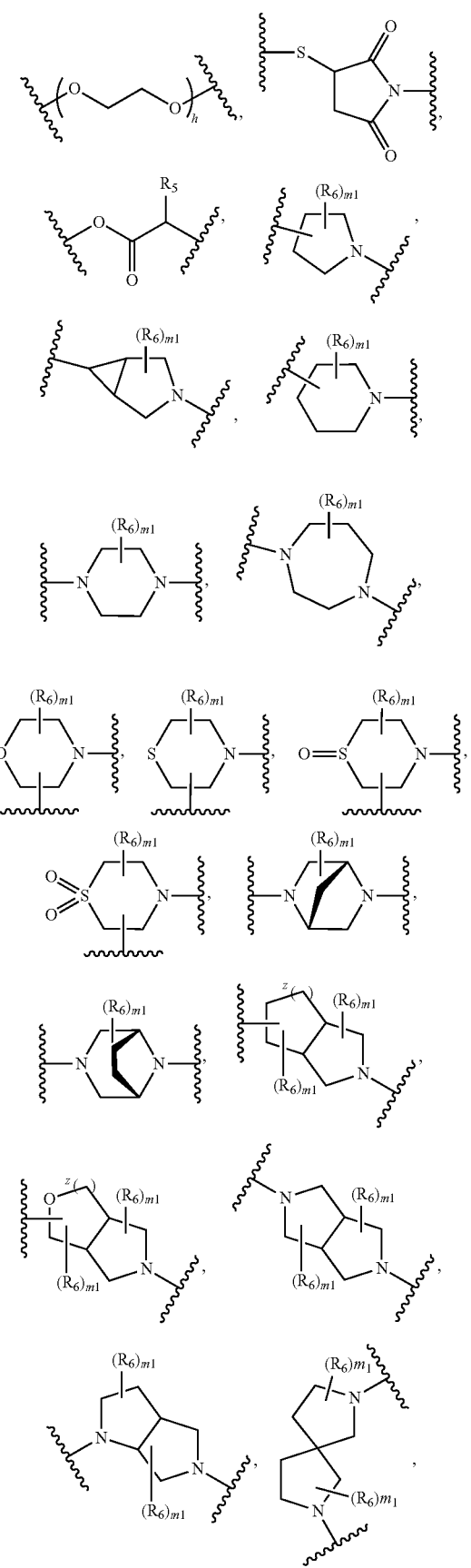

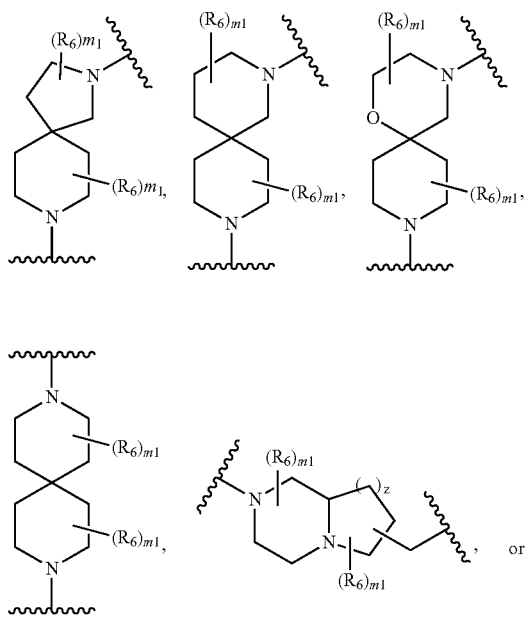

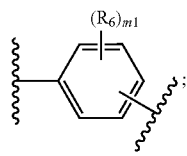

wherein the representation of L is not limited directionally left to right as is depicted, rather either the left side or the right side of L can be bound to the $W_1$ side of the compound of Formula IB;

each $R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each g is independently 2, 3, or 4;

each h is independently 1, 2, 3, or 4;

each m is independently 0, 1, 2, or 3; if m is more than 1, then L can be the same or different;

each m1 is independently 0, 1, 2 or 3;

k is 0, 1, 2, or 3;

z is 1, 2, or 3;

each $R_4$ is independently H or optionally substituted $C_1$-$C_6$ alkyl, wherein a methylene unit of the $C_1$-$C_6$ alkyl can be optionally substituted for either O or NR, and in $NR_4R_4$, both $R_4$ when taken together with the nitrogen to which they are attached can form a heterocyclic ring such as a pyrrolidine, piperidine, morpholine, piperazine or pyrrole;

each $R_3$ is independently H, —$C_1$-$C_6$ alkyl or —C(CH$_2$OH)$_2$;

each $R_5$ is independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids;

each R is independently —H, or straight or branched $C_1$-$C_4$ alkyl optionally substituted with OH, or halogen.

In another aspect, compounds of Formula IC are described:

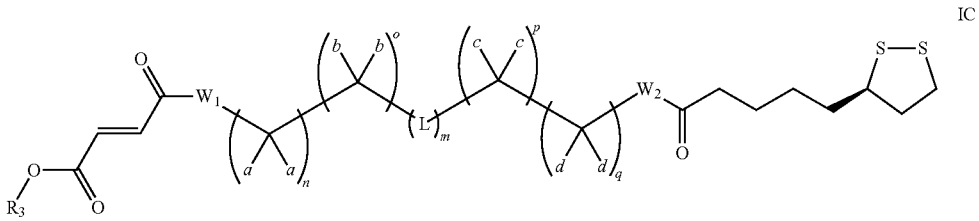

and pharmaceutically acceptable salts, hydrates, solvates, prodrugs, enantiomers, and stereoisomers thereof;

wherein each $W_1$ and $W_2$ is independently null, O, S, NH, or NR, or $W_1$ and $W_2$ can be taken together can form an optionally substituted imidazolidine or piperazine group;

each a, b, c, and d is independently —H, -D, —$CH_3$, —$OCH_3$, —$OCH_2CH_3$, —C(O)OR, or benzyl, or two of a, b, c, and d can be taken together, along with the single carbon to which they are bound, to form a cycloalkyl or heterocycle;

each n, o, p, and q is independently 0, 1, or 2;

each L is independently null, —O—, —C(O)—, —S—, —S(O)—, —S(O)$_2$—, —S—S—, —($C_1$-$C_6$ alkyl)-, —($C_3$-$C_6$ cycloalkyl)-, a heterocycle, a heteroaryl,

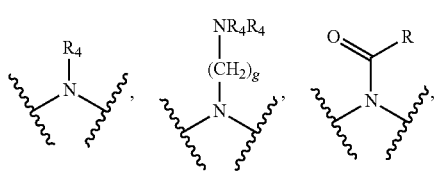

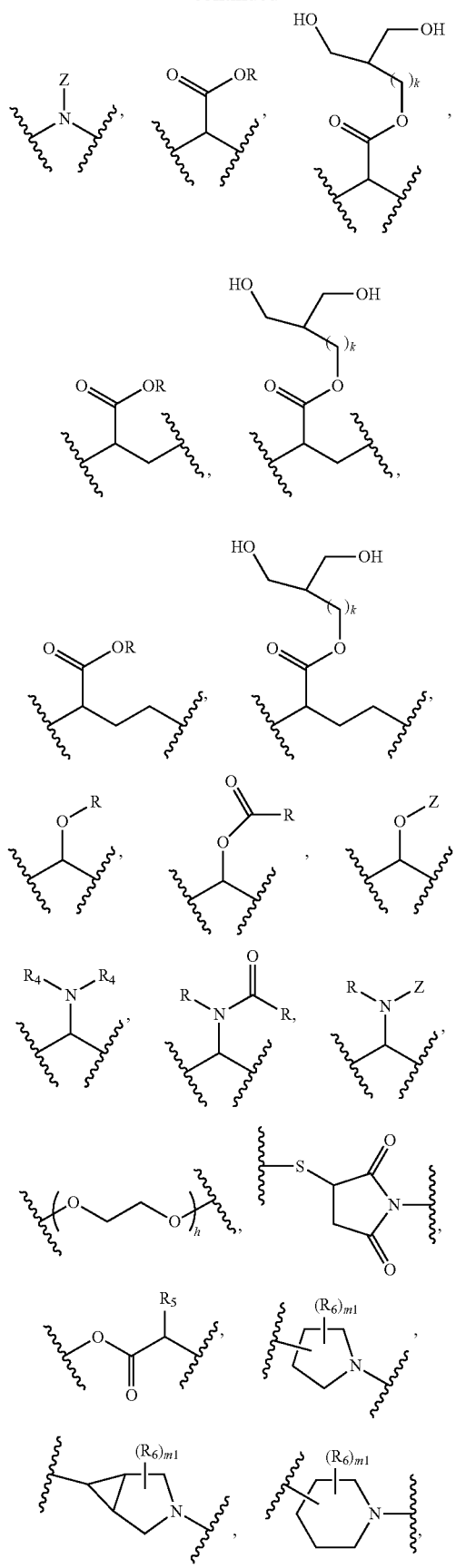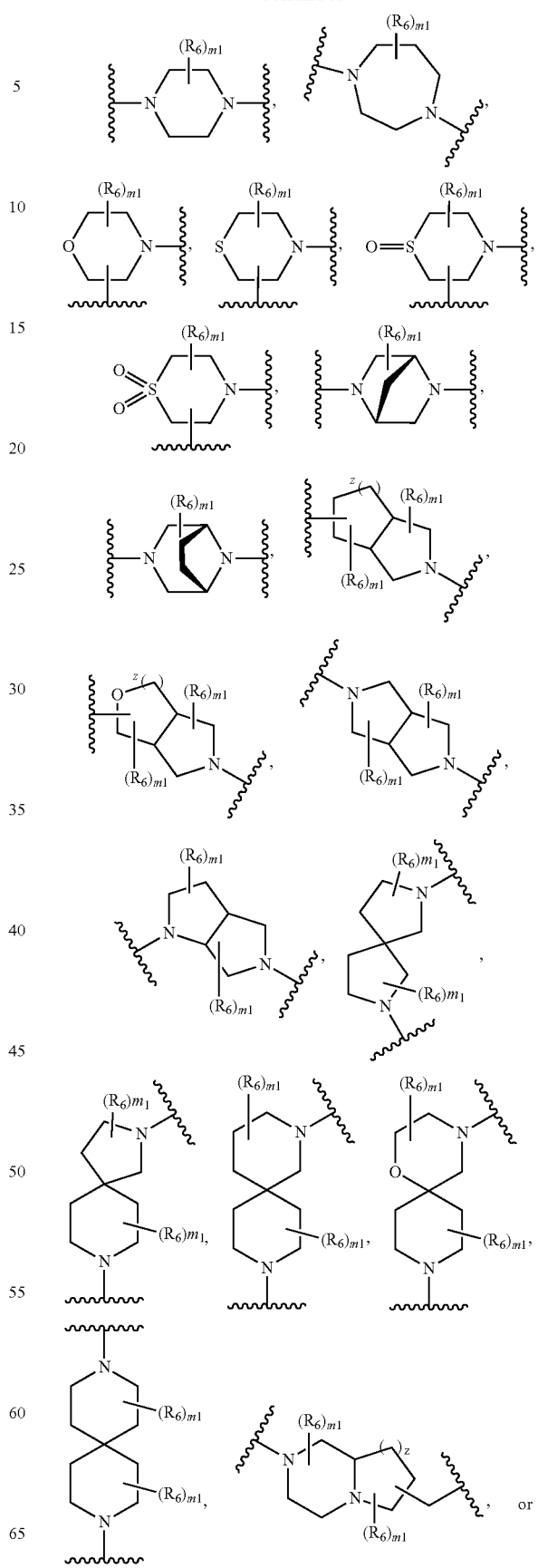

-continued

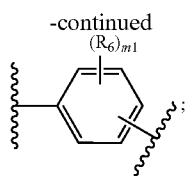

wherein the representation of L is not limited directionally left to right as is depicted, rather either the left side or the right side of L can be bound to the $W_1$ side of the compound of Formula IC;

each $R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl;

each g is independently 2, 3, or 4;

each h is independently 1, 2, 3, or 4;

each m is independently 0, 1, 2, or 3; if m is more than 1, then L can be the same or different;

each m1 is independently 0, 1, 2, or 3;

k is 0, 1, 2, or 3;

z is 1, 2, or 3;

each $R_4$ is independently H or optionally substituted $C_1$-$C_6$ alkyl, wherein a methylene unit of the $C_1$-$C_6$ alkyl can be optionally substituted for either O or NR, and in $NR_4R_4$, both $R_4$ when taken together with the nitrogen to which they are attached can form a heterocyclic ring such as a pyrrolidine, piperidine, morpholine, piperazine or pyrrole;

each $R_3$ is independently H, —$C_1$-$C_6$ alkyl or —C(CH$_2$OH)$_2$;

each $R_5$ is independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids;

each R is independently —H, or straight or branched $C_1$-$C_4$ alkyl optionally substituted with OH or halogen.

In compounds of Formula I, IA, IB, IC, and II, any one or more of H may be substituted with a deuterium. It is also understood that in compounds of Formula I, IA, IB, IC, and II, that a methyl substituent can be substituted with a $C_1$-$C_6$ alkyl.

Also described are pharmaceutical formulations comprising at least one Fatty Acid Fumarate Derivative.

Also described herein are methods of treating a disease susceptible to treatment with a Fatty Acid Fumarate Derivative in a patient in need thereof by administering to the patient an effective amount of a Fatty Acid Fumarate Derivative.

Also described herein are methods of treating metabolic disorders or autoimmune disease or neurodegenerative diseases by administering to a patient in need thereof an effective amount of a Fatty Acid Fumarate Derivative.

Also described herein are methods of treating neurodegenerative diseases by administering to a patient in need thereof an effective amount of a Fatty Acid Fumarate Derivative.

Also described herein are methods of treating cancer by administering to a patient in need thereof an effective amount of a Fatty Acid Fumarate Derivative.

The invention also includes pharmaceutical compositions that comprise an effective amount of a Fatty Acid Fumarate Derivative and a pharmaceutically acceptable carrier. The compositions are useful for treating or preventing a metabolic disorder, neurodegenarative diseases, and cancer. The invention includes a Fatty Acid Fumarate Derivative when provided as a pharmaceutically acceptable prodrug, a hydrate, a salt, such as a pharmaceutically acceptable salt, enantiomer, stereoisomer, or mixtures thereof.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DETAILED DESCRIPTION OF THE INVENTION

Figure 1:
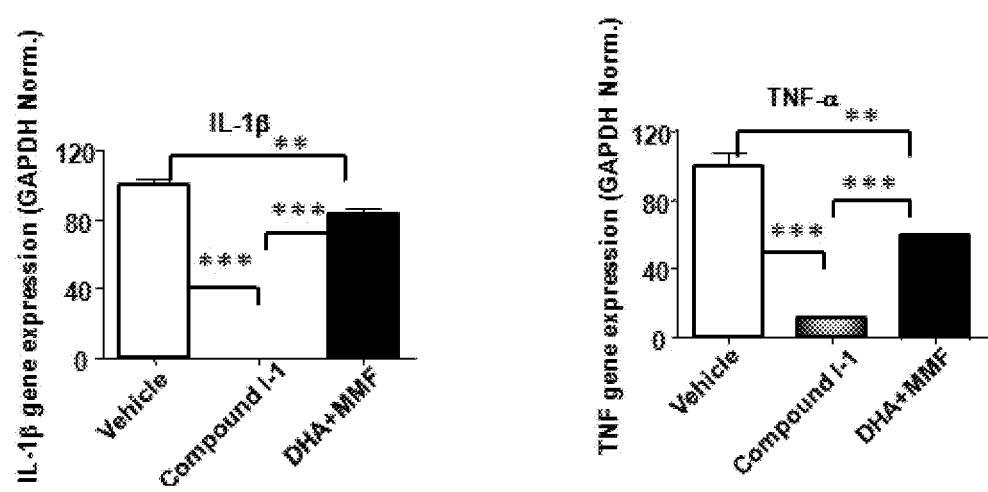
FIG. 1 is a graphical representation of the effect of IL-1β and TNF-α gene expression in RAW264.7 macrophages that were treated with either compound I-1 or a combination of mono methyl fumarate and DHA.

Metabolic disorders are a wide variety of medical disorders that interfere with a subject's metabolism. Metabolism is the process a subject's body uses to transform food into energy. Metabolism in a subject with a metabolic disorder is disrupted in some way. Autoimmune diseases arise from an overactive immune response of the body against tissues normally present in the body. Neurodegenerative diseases result from the deterioration of neurons or their myelin sheaths, which would eventually lead to a variety of CNS-related dysfunctions. The Fatty Acid Fumarate Derivatives possess the ability to treat or prevent metabolic disorders, autoimmune or neurodegenerative diseases. In addition, the Fatty Acid Fumarate Derivatives can also be used to treat a variety of cancers such as carcinoma, sarcoma, lymphoma, leukemia, melanoma, mesothelioma, multiople myeloma, seminoma, and cancer of the bladder, blood, bone, brain, breast, central nervous system, colon, endometrium, esophagus, genitourinary tract, head, larynx, liver, lung, neck, ovary, pancreas, prostate, testicle, spleen, small intestine, large intestine or stomach.

The Fatty Acid Fumarate Derivatives have been designed to bring together fumaric acid and ester analogs thereof and fatty acids into a single molecular conjugate. The activity of the Fatty Acid Fumarate Derivatives is substantially greater than the sum of the components suggesting that the activity induced by the Fatty Acid Fumarate Derivatives is synergistic.

DEFINITIONS

The following definitions are used in connection with the Fatty Acid Fumarate Derivatives:

The term "Fatty Acid Fumarate Derivatives" includes any and all possible isomers, stereoisomers, enantiomers, diastereomers, tautomers, pharmaceutically acceptable salts, hydrates, solvates, and prodrugs of the Fatty Acid Fumarate Derivatives described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

"$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl.

"$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl.

"$C_1$-$C_5$ alkyl" refers to a straight or branched chain saturated hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl. It is understood that any of the substitutable hydrogens on a cycloalkyl can be substituted with halogen, $C_1$-$C_3$ alkyl, hydroxyl, alkoxy and cyano groups.

The term "heterocycle" as used herein refers to a monocyclic or bicyclic hydrocarbon containing 3-12 carbon atoms wherein at least one of the carbon atoms is substituted with a O, N, or S. Examples of a heterocycle include, but are not limited to, aziridine, oxirane, thiirane, azetidine, oxetane, thietane, pyrrolidine, tetrahydrofurane, tetrahydrothiophene, piperidine, tetrahydropyran, thiane, imidazolidine, oxazolidine, thiazolidine, dioxolane, dithiolane, piperazine, oxazine, dithiane, dioxane, diazabicycloheptane and diazabicyclooctane.

The term "heteroaryl" as used herein refers to a monocyclic or bicyclic ring structure having 5 to 12 ring atoms wherein one or more of the ring atoms is a heteroatom, e.g. N, O or S and wherein one or more rings of the bicyclic ring structure is aromatic. Some examples of heteroaryl are pyridyl, furyl, pyrrolyl, thienyl, thiazolyl, oxazolyl, imidazolyl, indolyl, tetrazolyl, benzofuryl, xanthenes and dihydroindole. It is understood that any of the substitutable hydrogens on a heteroaryl can be substituted with halogen, $C_1$-$C_3$ alkyl, hydroxyl, alkoxy and cyano groups.

The term "any one of the side chains of the naturally occurring amino acids" as used herein means a side chain of any one of the following amino acids: Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Arginine, Serine, Histidine, and Tyrosine.

The term "fatty acid" as used herein means an omega-3 fatty acid, fatty acids that are metabolized in vivo to omega-3 fatty acids, and lipoic acid. Non-limiting examples of fatty acids are all-cis-7,10,13-hexadecatrienoic acid, α-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA or all-cis-5,8,11,14,17-eicosapentaenoic acid), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15,18,21-docosahexaenoic acid), tetracosahexaenoic acid (nisinic acid or all-cis-6,9,12,15,18,21-tetracosenoic acid) and stereoisomers of lipoic acid.

A "subject" is a mammal, e.g., a human, mouse, rat, guinea pig, dog, cat, horse, cow, pig, or non-human primate, such as a monkey, chimpanzee, baboon or rhesus.

The invention also includes pharmaceutical compositions comprising an effective amount of a Fatty Acid Fumarate Derivative and a pharmaceutically acceptable carrier. The invention includes a Fatty Acid Fumarate Derivative when provided as a pharmaceutically acceptable prodrug, hydrate, salt, such as a pharmaceutically acceptable salt, enantiomers, stereoisomers, or mixtures thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "metabolic disorder," as used herein refers to disorders, diseases and syndromes involving dyslipidemia, and the terms metabolic disorder, metabolic disease, and metabolic syndrome are used interchangeably herein.

An "effective amount" when used in connection with a Fatty Acid Fumarate Derivative is an amount effective for treating or preventing a metabolic disorder.

The term "carrier," as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating," with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer," "administering," or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a Fatty Acid Fumarate Derivative.

The following abbreviations are used herein and have the indicated definitions: BSA is bovine serum albumin, DCC is dicyclohexylcarbodiimide, CDI is 1,1'-carbonyldiimidazole, DMEM is Dulbecco's modified Eagle's medium, EDC is 1-Ethyl-3-[3-dimethylaminopropyl]carbodiimide hydrochloride, EtOAc is ethyl acetate, HATU is 2-(1H-7-Azabenzotriazol-1-yl)-1,1,3,3-tetramethyl uronium hexafluorophosphate methanaminium, RT is room temperature, TFA is trifluoroacetic acid, and h is hour.

Compounds

The present invention provides Fatty Acid Fumarate Derivatives according to Formula I, IA, IB, IC, and II, as set forth below.

Described herein are compounds of Formula I and Formula II:

and pharmaceutically acceptable salts, hydrates, solvates, prodrugs, enantiomers, and stereoisomers thereof;

wherein $W_1$, $W_2$, a, b, c, d, m, ml, n, o, p, q, L, Z, r, s, t, v, R, $R_1$, $R_2$, $R_3$, $R_4$, $R_5$, $R_6$, $W_1'$, $W_2'$, a', c', b', d', n', o', p', q', ml', L', and Z' is as defined above for Formula I and Formula II, provided that there is at least one

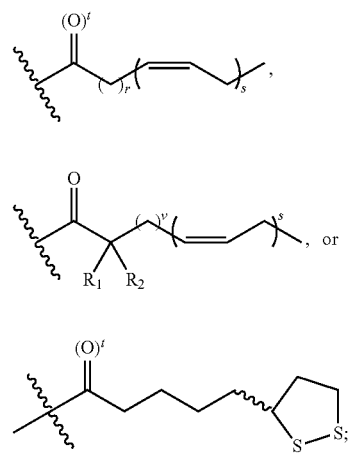

in the compound.

In some embodiments, one Z is

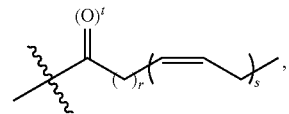

and r is 2.

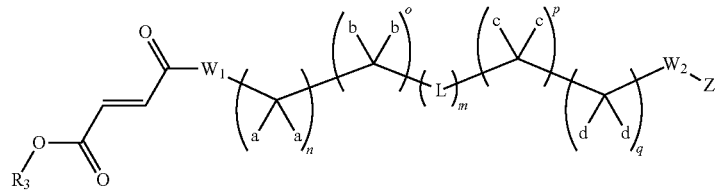

I

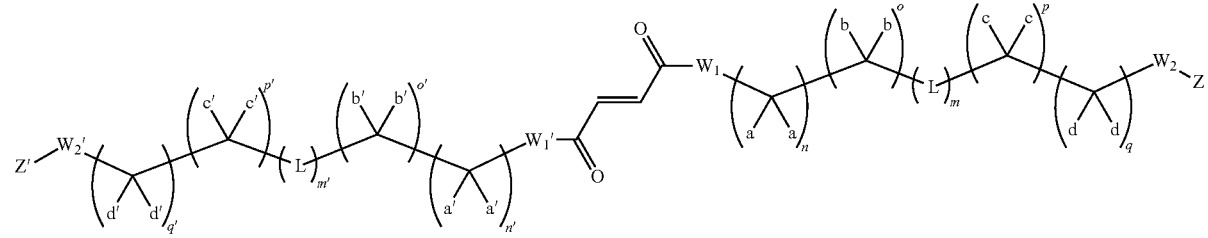

II

In some embodiments, one Z is

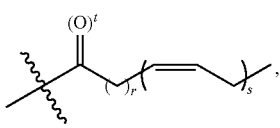

and r is 3.

In some embodiments, one Z is

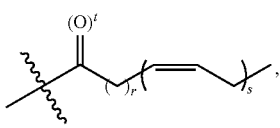

and r is 7.

In other embodiments, one Z is

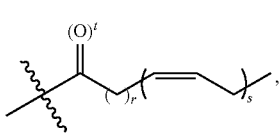

and s is 3.

In some embodiments, one Z is

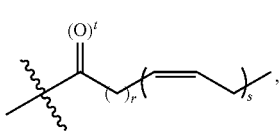

and s is 5.

In some embodiments, one Z is

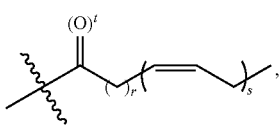

and s is 6.

In some embodiments, one Z is

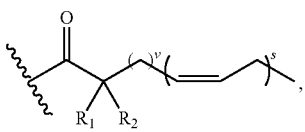

and v is 1.

In other embodiments, one Z is

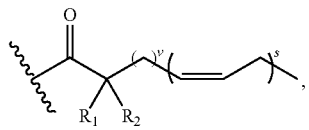

and v is 2.

In some embodiments, one Z is

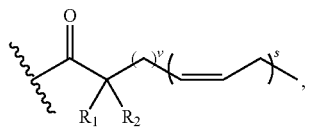

and v is 6.

In some embodiments, one Z is

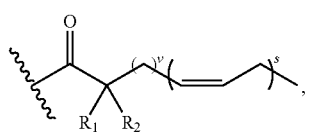

and s is 3.

In some embodiments, one Z is

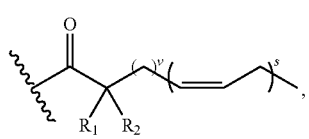

and s is 5.

In other embodiments, one Z is

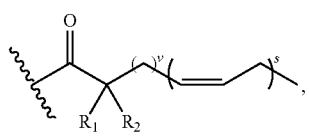

and s is 6.

In other embodiments, Z is

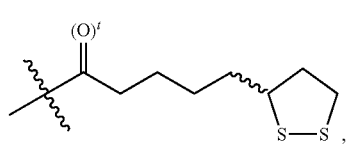

and t is 1.

In some embodiments, Z is

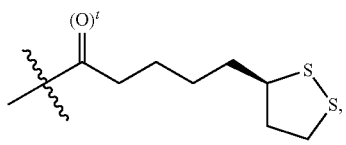

and t is 1.

In another aspect, compounds of Formula IA are described:

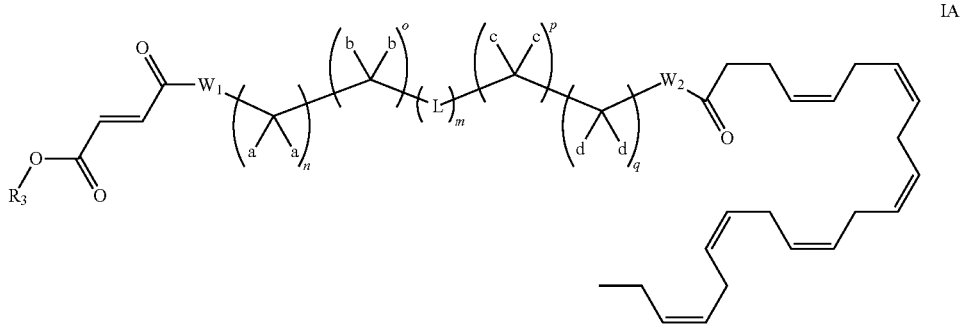

IA and pharmaceutically acceptable salts, hydrates, solvates, prodrugs, enantiomers, and stereoisomers thereof;
wherein
$W_1, W_2, a, b, c, d, m, ml, n, o, p, q, L, R, R_1, R_2, R_3, R_4, R_5, R_6$ are as defined above for Formula IA.

In another aspect, compounds of Formula IB are described:

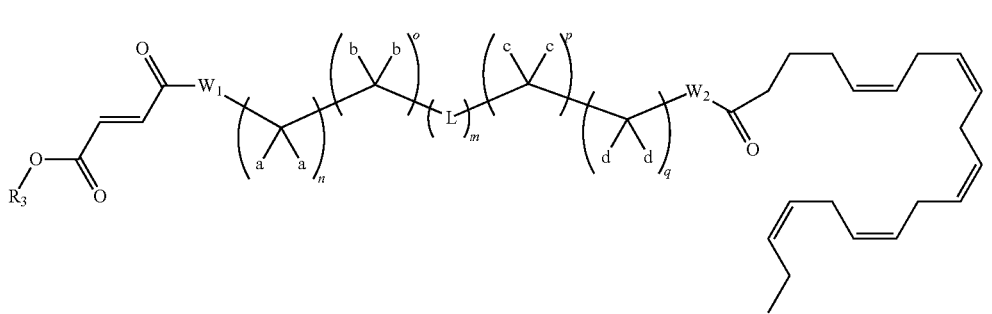

IB and pharmaceutically acceptable salts, hydrates, solvates, prodrugs, enantiomers, and stereoisomers thereof;
wherein
$W_1, W_2, a, b, c, d, m, ml, n, o, p, q, L, R, R_1, R_2, R_3, R_4, R_5, R_6$ are as defined above for Formula IB.

In another aspect, compounds of Formula IC are described:

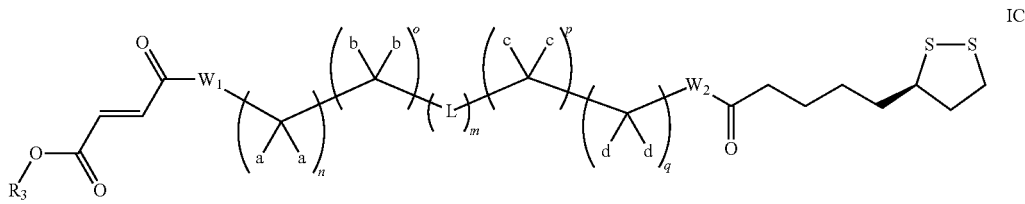

IC and pharmaceutically acceptable salts, hydrates, solvates, prodrugs, enantiomers, and stereoisomers thereof;
wherein
$W_1, W_2, a, b, c, d, m, ml, n, o, p, q, L, R, R_1, R_2, R_3, R_4, R_5$ and $R_6$ are as defined above for Formula IC.

The following embodiments are illustrative of compounds of Formula I, IA, IB, IC, and II.

In some embodiments, $R_3$ is $CH_3$.
In some embodiments, $R_3$ is —$CH_2CH_3$.
In some embodiments, $R_3$ is H.
In some embodiments, $W_1$ is NH.
In some embodiments, $W_2$ is NH.
In some embodiments, $W_t$ is O.
In some embodiments, $W_2$ is O.
In some embodiments, $W_1$ is null.
In some embodiments, $W_2$ is null.
In some embodiments, $W_1$ and $W_2$ are each NH.
In some embodiments, $W_1$ and $W_2$ are each null.
In some embodiments, $W_1$ is O and $W_2$ are NH.
In some embodiments, $W_1$ and $W_2$ is NR, and R are $CH_3$.
In some embodiments, m is 0.
In other embodiments, m is 1.
In other embodiments, m is 2.

In some embodiments, L is —S— or —S—S—.
In some embodiments, L is —O—.
In some embodiments, L is —C(O)—.
In some embodiments, L is heteroaryl.
In some embodiments, L is heterocycle.
In some embodiments, L is

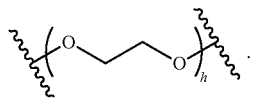

In some embodiments, L is

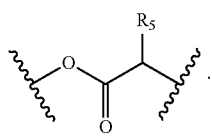

In some embodiments, L is

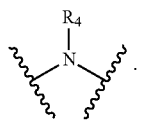

In some embodiments, L is

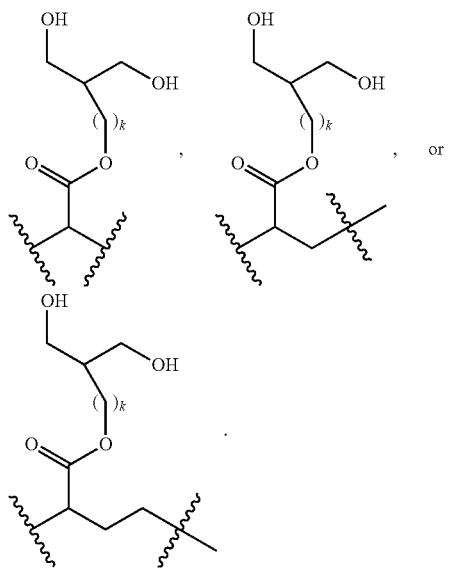

In some embodiments, L is

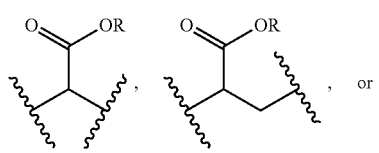

In some embodiments, L is

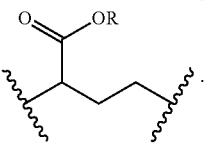

In some embodiments, L is

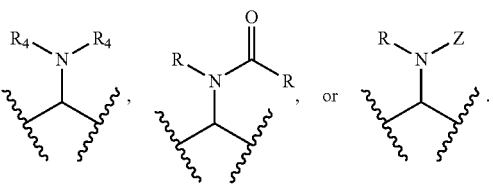

In some embodiments, L is

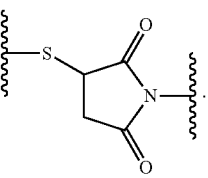 [SMILES: *SC1CC(=O)N(*)C1=O]

In some embodiments, L is

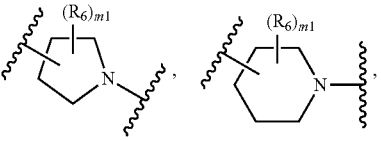
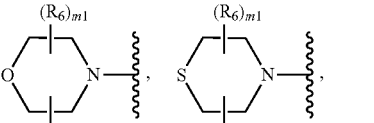
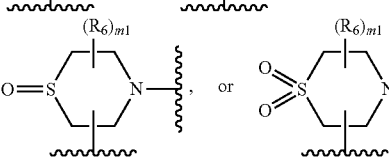

In some embodiments, L is

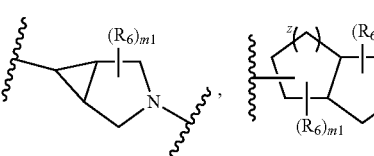
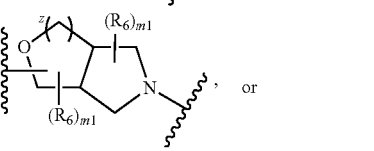

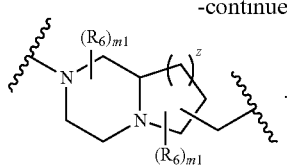

In some embodiments, L is

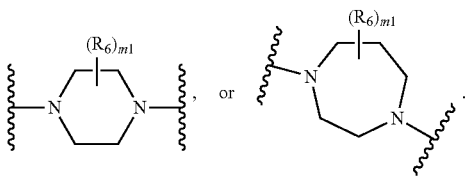

In some embodiments, L is

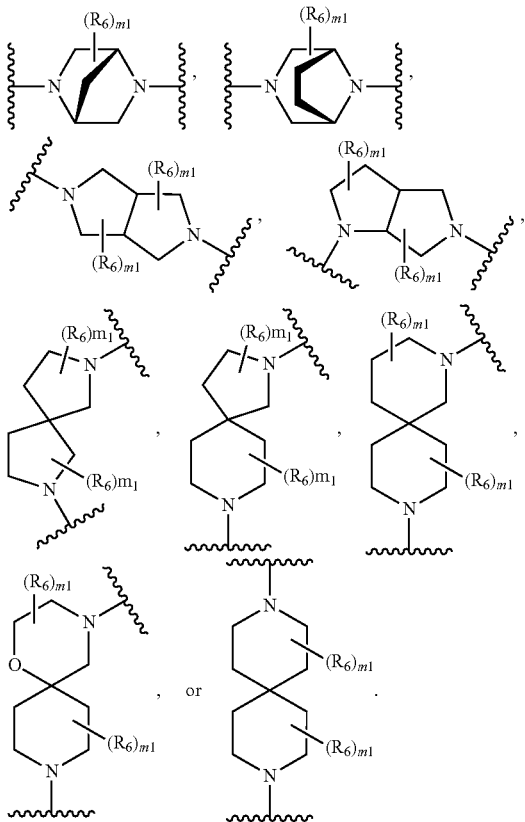

In other embodiments, one of n, o, p, and q is 1.
In some embodiments, two of n, o, p, and q are each 1.
In other embodiments, three of n, o, p, and q are each 1.
In some embodiments n, o, p, and q are each 1.
In some embodiments, two of n, o, p, and q are each 1 and the other two are each 0.
In some embodiments, r is 2 and s are 6.
In some embodiments, r is 3 and s are 5.
In some embodiments, t is 1.
In some embodiments, $W_1$ and $W_2$ are each NH, m is 0, n, and o are each 1, and p and q are each 0.
In some embodiments, $W_1$ and $W_2$ are each NH, m is 1, n, o, p, and q are each 1, and L is O.

In some embodiments, $W_1$ and $W_2$ are each NH, m is 1, n, o, p, and q are each 1, and L is

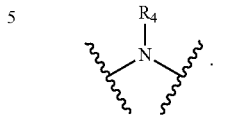

In some embodiments, $W_1$ and $W_2$ are each NH, m is 1, n, o, p, and q are each 1, and L is —S—S—.

In some embodiments, $W_1$ and $W_2$ are each NH, m is 1, n and o are each 0, p and q are each 1, and L is

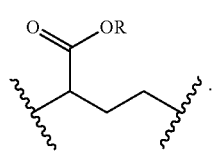

In some embodiments, $W_1$ and $W_2$ are each NH, m is 1, k is 0, n and o are each 0, p and q are each 1, and L is

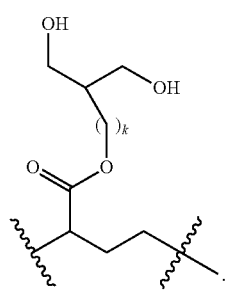

In some embodiments, $W_1$ and $W_2$ are each NH, m is 1, n and o are each 1, p and q are each 0, and L is

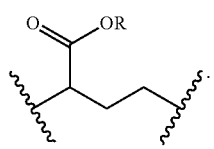

In some embodiments, $W_1$ and $W_2$ are each NH, m is 1, k is 0, n is 1, o, p and q are each 0, and L is

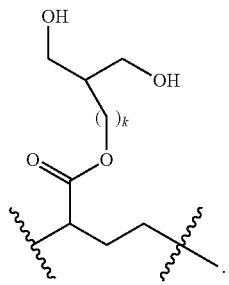

In some embodiments, $W_1$ and $W_2$ are each NH, m is 1, n, o, and p are each 0, and q is 1, and L is

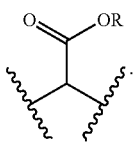

In some embodiments, $W_1$ and $W_2$ are each NH, m is 1, k is 1, n, o, and p are each 0, and q is 1, and L is

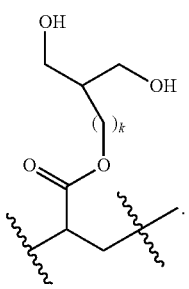

In some embodiments, $W_1$ and $W_2$ are each NH, m is 1, n is 1, and o, p, and q are each 0, and L is

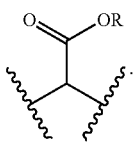

In some embodiments, $W_1$ and $W_2$ are each NH, m is 1, k is 1, o, p, and q are each 0, and L is

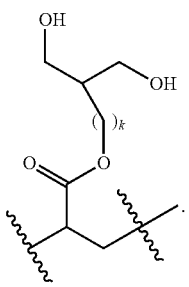

In some embodiments, $W_1$ and $W_2$ are each NH, m is 1, n, o, p, and q are each 1, and L is

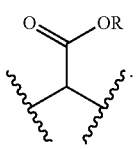

In some embodiments, $W_1$ and $W_2$ are each NH, m is 1, n, o, p, and q are each 1, and L is

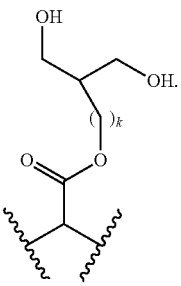

In some embodiments, $W_1$ and $W_2$ are each NH, m is 0, k is 1, o and p are each 1, and q is 0.

In some embodiments, $W_1$ and $W_2$ are each NH, m is 0, n, o, p, and q are each 1.

In some embodiments, $W_1$ and $W_2$ are each NH, m is 0, n and o are each 1, p and q are each 0, and each a is $CH_3$.

In some embodiments, $W_1$ and $W_2$ are each NH, m is 0, n and o are each 1, p and q are each 0, and each b is $CH_3$.

In some embodiments, $W_1$ and $W_2$ are each NH, m is 1, n, o, p, and q are each 1, $R_4$ is H, and L is

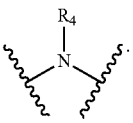

In some embodiments, $W_1$ and $W_2$ are each NH, m is 1, n, p and q are each 1, and o is 2, $R_4$ is H, and L is

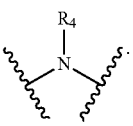

In some embodiments, $W_1$ and $W_2$ are each NH, m is 1, n, o, p are each 1, and q is 2, and L is

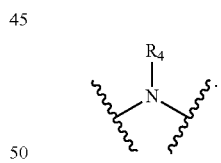

In some embodiments, $W_1$ and $W_2$ are each NH, m is 1, n, o, p, and q are each 1, and L is

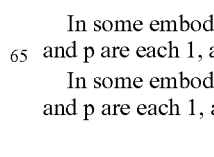

In some embodiments, $W_1$ and $W_2$ are each NH, m is 1, n and p are each 1, and o and q are each 0, and L is —C(O)—.

In some embodiments, $W_1$ and $W_2$ are each NH, m is 1, n and p are each 1, and o, and q are each 0, and L is

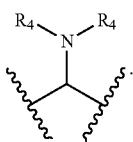

In some embodiments, $W_1$ and $W_2$ are each NH, m is 1, n, o, p, q are each 1, and L is

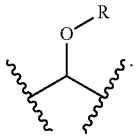

In some embodiments, $W_1$ and $W_2$ are each NH, m is 1, n, o, p, and q are each 1, h is 1, and L is

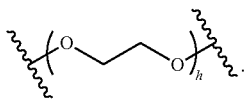

In some embodiments, $W_1$ and $W_2$ are each NH, m is 1, n, o, p, and q are each 1, and L is —S—.

In some embodiments, $W_1$ and $W_2$ are each NH, m is 1, n, o, p are each 0, q is 1, one d is —CH$_3$, and L is

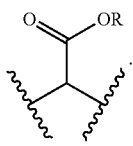

In some embodiments, $W_1$ and $W_2$ are each NH, m is 2, n, o, p, and q are each 0, one L is

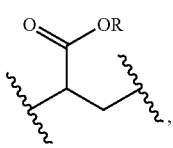

and one L is

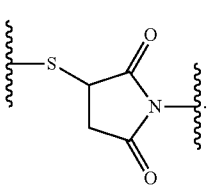 [SMILES: *SC1CC(=O)N(*)C1=O]

In some embodiments, m is 0, n, o, p, and q are each 0, and $W_1$ and $W_2$ are taken together to form an optionally substituted piperazine group.

In some embodiments, m is 1, n, o, p, and q are each 0, $W_1$ and $W_2$ are each null, and L is

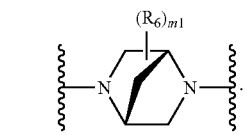

In some embodiments, m is 1, n and p are each 1, o and q are each 0, $W_1$ and $W_2$ are each NH, and L is $C_3$-$C_6$ cycloalkyl.

In some embodiments, m is 1, n is 1, o, p, and q are each 0, $W_1$ and $W_2$ are each NH, and L is $C_3$-$C_6$ cycloalkyl.

In some embodiments, m is 1, n, o, p, are each 0, q is 1, $W_1$ and $W_2$ are each NH, and L is $C_3$-$C_6$ cycloalkyl.

In some embodiments, m is 1, n, o, p, and q are each 0, $W_1$ is NH, $W_2$ is null, and L is

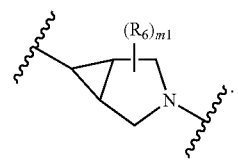

In some embodiments, m is 1, n, o, p, and q are each 0, $W_1$ is null, $W_2$ is NH, and L is

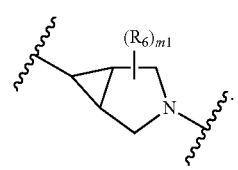

In some embodiments, m is 1, n, o, p, and q are each 0, $W_1$ is NH, $W_2$ is null, and L is

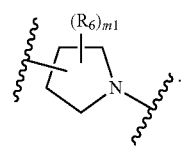

In some embodiments, m is 1, n, o, p, and q are each 0, $W_1$ is null, $W_2$ is NH, and L is

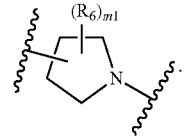

In some embodiments, m is 1, n is 1, o, p, and q are each 0, $W_1$ is NH, $W_2$ is null, and L is

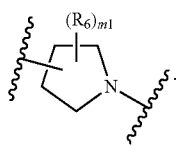

In some embodiments, m is 1, n, o, p, are each 0, q is 1, $W_1$ is null, $W_2$ is NH, and L is

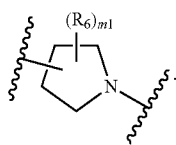

In some embodiments, m is 1, n, o, p, and q are each 0, $W_1$ is NH, $W_2$ is null, and L is

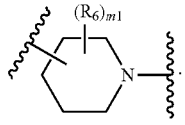

In some embodiments, m is 1, n, o, p, and q are each 0, $W_1$ is null, $W_2$ is NH, and L is

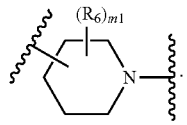

In some embodiments, m is 1, n is 1, o, p, and q are each 0, $W_1$ is NH, $W_2$ is null, and L is

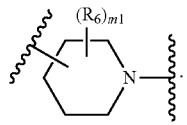

In some embodiments, m is 1, n, o, p, are each 0, q is 1, $W_1$ is null, $W_2$ is NH, and L is

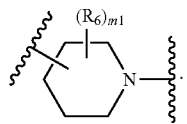

In some embodiments, m is 1, n is 1, o, p, and q are each 0, $W_1$ is NH, $W_2$ is null, and L is

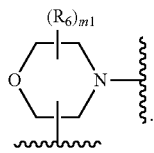

In some embodiments, m is 1, n, o, p, are each 0, q is 1, $W_1$ is null, $W_2$ is NH, and L is

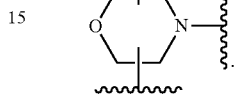

In some embodiments, m is 1, n, o, p, q are each 0, $W_1$ and $W_2$ is null, and L is

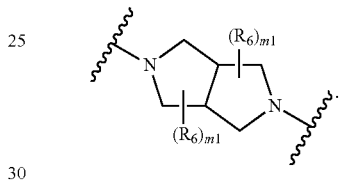

In some embodiments, m is 1, n, o, p, q are each 0, $W_1$ and $W_2$ is null, and L is

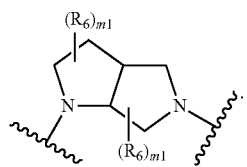

In some embodiments, m is 1, n, o, p, q are each 0, $W_1$ is NH, $W_2$ is null, and L is

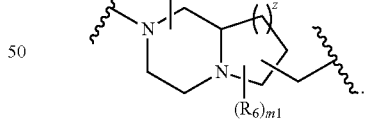

In some embodiments, m is 1, n, o, p, q are each 0, $W_1$ is null, $W_2$ is NH, and L is

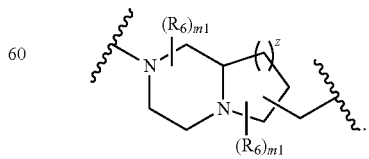

In some embodiments, m is 1, n, o, p, are each 0, q is 1, $W_1$ and $W_2$ are each and NH, is null, L is

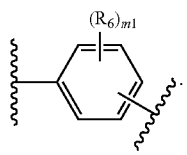

In some embodiments, m is 1, n, o, p, are each 0, q is 1, $W_1$ and $W_2$ are each NH, is null, and L is a heteroaryl.

In some of the foregoing embodiments, r is 2, s is 6 and t is 1.

In some of the foregoing embodiments, r is 3, s is 5 and t is 1.

In some of the foregoing embodiments, Z is

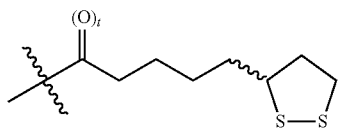

and t is 1.

In the compounds of Formula I, IA, IB, IC and II, any one or more of H may be substituted with a deuterium.

In other illustrative embodiments, compounds of Formula I, IA, IB, IC and II are as set forth below:
- (E)-methyl 4-(2-(4Z,7Z,10Z,13Z,16Z,19Z)-docosa-4,7,10,13,16,19-hexaenamidoethylamino)-4-oxobut-2-enoate (I-1);
- (E)-methyl 4-(2-(5Z,8Z,11Z,14Z,17Z)-icosa-5,8,11,14,17-pentaenamidoethylamino)-4-oxobut-2-enoate (I-2);
- (E)-methyl 4-(2-(2-(4Z,7Z,10Z,13Z,16Z,19Z)-docosa-4,7,10,13,16,19-hexaenamidoethoxy)ethylamino)-4-oxobut-2-enoate (I-3);
- (E)-methyl 4-(2-((2-(4Z,7Z,10Z,13Z,16Z,19Z)-docosa-4,7,10,13,16,19-hexaenamidoethyl)(methyl)amino)ethylamino)-4-oxobut-2-enoate (I-4);
- (E)-methyl 4-(2-(2-(2-(4Z,7Z,10Z,13Z,16Z,19Z)-docosa-4,7,10,13,16,19-hexaenamidoethyl)disulfanyl)ethylamino)-4-oxobut-2-enoate (I-5);
- (S)-methyl 6-((4Z,7Z,10Z,13Z,16Z,19Z)-docosa-4,7,10,13,16,19-hexaenamido)-2-((E)-4-methoxy-4-oxobut-2-enamido)hexanoate (I-6);
- (S)-6-((4Z,7Z,10Z,13Z,16Z,19Z)-docosa-4,7,10,13,16,19-hexaenamido)-2-((E)-4-methoxy-4-oxobut-2-enamido)hexanoic acid (I-7);
- (S)-1,3-dihydroxypropan-2-yl 6-((4Z,7Z,10Z,13Z,16Z,19Z)-docosa-4,7,10,13,16,19-hexaenamido)-2-((E)-4-methoxy-4-oxobut-2-enamido)hexanoate (I-8);
- (S)-methyl 2-((4Z,7Z,10Z,13Z,16Z,19Z)-docosa-4,7,10,13,16,19-hexaenamido)-6-((E)-4-methoxy-4-oxobut-2-enamido)hexanoate (I-9);
- (S)-2-((4Z,7Z,10Z,13Z,16Z,19Z)-docosa-4,7,10,13,16,19-hexaenamido)-6-((E)-4-methoxy-4-oxobut-2-enamido)hexanoic acid (I-10);
- (S)-1,3-dihydroxypropan-2-yl 2-((4Z,7Z,10Z,13Z,16Z,19Z)-docosa-4,7,10,13,16,19-hexaenamido)-6-((E)-4-methoxy-4-oxobut-2-enamido)hexanoate (I-11);
- (E)-methyl 4-(3-(4Z,7Z,10Z,13Z,16Z,19Z)-docosa-4,7,10,13,16,19-hexaenamido-1-methoxy-1-oxopropan-2-ylamino)-4-oxobut-2-enoate (I-12);
- 3-(4Z,7Z,10Z,13Z,16Z,19Z)-docosa-4,7,10,13,16,19-hexaenamido-2-((E)-4-methoxy-4-oxobut-2-enamido)propanoic acid (I-13);
- (E)-methyl 4-(1-(1,3-dihydroxypropan-2-yloxy)-3-(4Z,7Z,10Z,13Z,16Z,19Z)-docosa-4,7,10,13,16,19-hexaenamido-1-oxopropan-2-ylamino)-4-oxobut-2-enoate (I-14);
- (E)-methyl 4-(2-(4Z,7Z,10Z,13Z,16Z,19Z)-docosa-4,7,10,13,16,19-hexaenamido-3-methoxy-3-oxopropylamino)-4-oxobut-2-enoate (I-15);
- 2-(4Z,7Z,10Z,13Z,16Z,19Z)-docosa-4,7,10,13,16,19-hexaenamido-3-((E)-4-methoxy-4-oxobut-2-enamido)propanoic acid (I-16);
- (E)-methyl 4-(3-(1,3-dihydroxypropan-2-yloxy)-2-(4Z,7Z,10Z,13Z,16Z,19Z)-docosa-4,7,10,13,16,19-hexaenamido-3-oxopropylamino)-4-oxobut-2-enoate (I-17);
- 2-(2-(4Z,7Z,10Z,13Z,16Z,19Z)-docosa-4,7,10,13,16,19-hexaenamidoethyl)-4-((E)-4-methoxy-4-oxobut-2-enamido)butanoic acid (I-18);
- (E)-methyl 4-(3-((1,3-dihydroxypropan-2-yloxy)carbonyl)-5-(4Z,7Z,10Z,13Z,16Z,19Z)-docosa-4,7,10,13,16,19-hexaenamidopentylamino)-4-oxobut-2-enoate (I-19);
- (E)-methyl 4-(3-(4Z,7Z,10Z,13Z,16Z,19Z)-docosa-4,7,10,13,16,19-hexaenamidopropylamino)-4-oxobut-2-enoate (I-20);
- (E)-methyl 4-(4-(4Z,7Z,10Z,13Z,16Z,19Z)-docosa-4,7,10,13,16,19-hexaenamidobutylamino)-4-oxobut-2-enoate (I-21);
- (E)-methyl 4-(1-(4Z,7Z,10Z,13Z,16Z,19Z)-docosa-4,7,10,13,16,19-hexaenamido-2-methylpropan-2-ylamino)-4-oxobut-2-enoate (I-22);
- (E)-methyl 4-(2-(4Z,7Z,10Z,13Z,16Z,19Z)-docosa-4,7,10,13,16,19-hexaenamido-2-methylpropylamino)-4-oxobut-2-enoate (I-23);
- (E)-methyl 4-(2-(2-(4Z,7Z,10Z,13Z,16Z,19Z)-docosa-4,7,10,13,16,19-hexaenamidoethylamino)ethylamino)-4-oxobut-2-enoate (I-24);
- (E)-methyl 4-(3-(2-(4Z,7Z,10Z,13Z,16Z,19Z)-docosa-4,7,10,13,16,19-hexaenamidoethylamino)propylamino)-4-oxobut-2-enoate (I-25);
- (E)-methyl 4-(2-(3-(4Z,7Z,10Z,13Z,16Z,19Z)-docosa-4,7,10,13,16,19-hexaenamidopropylamino)ethylamino)-4-oxobut-2-enoate (I-26);
- (E)-methyl 4-(2-((3-(4Z,7Z,10Z,13Z,16Z,19Z)-docosa-4,7,10,13,16,19-hexaenamidopropyl)(ethyl)amino)ethylamino)-4-oxobut-2-enoate (I-27);
- (E)-methyl 4-(2-(N-(3-(4Z,7Z,10Z,100Z,13Z,16Z,19Z)-docosa-4,7,10,13,16,19-hexaenamidopropyl)acetamido)ethylamino)-4-oxobut-2-enoate (I-28);
- (E)-methyl 4-(2-((2-(4Z,7Z,10Z,13Z,16Z,19Z)-docosa-4,7,10,13,16,19-hexaenamidoethyl)(2-morpholinoethyl)amino)ethylamino)-4-oxobut-2-enoate (I-29);
- (E)-methyl 4-(2-((2-(4Z,7Z,10Z,13Z,16Z,19Z)-docosa-4,7,10,13,16,19-hexaenamidoethyl)(3-(piperazin-1-yl)propyl)amino)ethylamino)-4-oxobut-2-enoate (I-30);
- (E)-methyl 4-(3-(4Z,7Z,10Z,13Z,16Z,19Z)-docosa-4,7,10,13,16,19-hexaenamido-2-oxopropylamino)-4-oxobut-2-enoate (I-31);
- (E)-methyl 4-(3-(4Z,7Z,10Z,13Z,16Z,19Z)-docosa-4,7,10,13,16,19-hexaenamido-2-morpholinopropylamino)-4-oxobut-2-enoate (I-32);
- (E)-methyl 4-(3-(4Z,7Z,10Z,13Z,16Z,19Z)-docosa-4,7,10,13,16,19-hexaenamido-2-(piperazin-1-yl)propylamino)-4-oxobut-2-enoate (I-33);
- (E)-methyl 4-(5-(4Z,7Z,10Z,13Z,16Z,19Z)-docosa-4,7,10,13,16,19-hexaenamido-3-hydroxypentylamino)-4-oxobut-2-enoate (I-34);
- (E)-methyl 4-(5-(4Z,7Z,10Z,13Z,16Z,19Z)-docosa-4,7,10,13,16,19-hexaenamido-3-morpholinopentylamino)-4-oxobut-2-enoate (I-35);

(E)-methyl 4-(2-(2-(2-(4Z,7Z,10Z,13Z,16Z,19Z)-docosa-4,7,10,13,16,19-hexaenamidoethoxy)ethoxy)ethylamino)-4-oxobut-2-enoate (I-36);
(E)-methyl 4-(2-(2-(4Z,7Z,10Z,13Z,16Z,19Z)-docosa-4,7,10,13,16,19-hexaenamidoethylthio)ethylamino)-4-oxobut-2-enoate (I-37);
(E)-methyl 4-(3-(2-(4Z,7Z,10Z,13Z,16Z,19Z)-docosa-4,7,10,13,16,19-hexaenamidoacetoxy)-1-methoxy-1-oxobutan-2-ylamino)-4-oxobut-2-enoate (I-38);
(E)-methyl 4-((R)-3-(1-(2-(4Z,7Z,10Z,13Z,16Z,19Z)-docosa-4,7,10,13,16,19-hexaenamidoethyl)-2,5-dioxopyrrolidin-3-ylthio)-1-methoxy-1-oxopropan-2-ylamino)-4-oxobut-2-enoate (I-39);
(E)-methyl 4-(4-(4Z,7Z,10Z,13Z,16Z,19Z)-docosa-4,7,10,13,16,19-hexaenoylpiperazin-1-yl)-4-oxobut-2-enoate (I-40);
(E)-methyl 4-((2R,6S)-4-((4Z,7Z,10OZ,13Z,16Z,19Z)-docosa-4,7,10,13,16,19-hexaenoyl)-2,6-dimethylpiperazin-1-yl)-4-oxobut-2-enoate (I-41);
(E)-methyl 4-((1S,4S)-5-((4Z,7Z,10Z,13Z,16Z,19Z)-docosa-4,7,10,13,16,19-hexaenoyl)-2,5-diaza-bicyclo[2.2.1]heptan-2-yl)-4-oxobut-2-enoate (I-42);
(E)-methyl 4-((2-((4Z,7Z,10Z,13Z,16Z,19Z)-docosa-4,7,10,13,16,19-hexaenamidomethyl)cyclopropyl)methylamino)-4-oxobut-2-enoate (I-43);
(E)-methyl 4-((4-(4Z,7Z,10Z,13Z,16Z,19Z)-docosa-4,7,10,13,16,19-hexaenamidocyclohexyl)methylamino)-4-oxobut-2-enoate (I-44);
(E)-methyl 4-(4-((4Z,7Z,10Z,13Z,16Z,19Z)-docosa-4,7,10,13,16,19-hexaenamidomethyl)cyclohexylamino)-4-oxobut-2-enoate (I-45);
(E)-methyl 4-(3-(4Z,7Z,10Z,13Z,16Z,19Z)-docosa-4,7,10,13,16,19-hexaenoyl-3-aza-bicyclo[3.1.0]hexan-6-ylamino)-4-oxobut-2-enoate (I-46);
(E)-methyl 4-(6-(4Z,7Z,10Z,13Z,16Z,19Z)-docosa-4,7,10,13,16,19-hexaenamido-3-aza-bicyclo[3.1.0]hexan-3-yl)-4-oxobut-2-enoate (I-47);
(E)-methyl 4-((S)-1-((4Z,7Z,10Z,13Z,16Z,19Z)-docosa-4,7,10,13,16,19-hexaenoyl)pyrrolidin-3-ylamino)-4-oxobut-2-enoate (I-48);
(E)-methyl 4-((S)-3-((4Z,7Z,10Z,13Z,16Z,19Z)-docosa-4,7,10,13,16,19-hexaenamido)pyrrolidin-1-yl)-4-oxobut-2-enoate (I-49);
(E)-methyl 4-((1-(4Z,7Z,10Z,13Z,16Z,19Z)-docosa-4,7,10,13,16,19-hexaenoylpyrrolidin-2-yl)methylamino)-4-oxobut-2-enoate (I-50);
(E)-methyl 4-(2-((4Z,7Z,10Z,13Z,16Z,19Z)-docosa-4,7,10,13,16,19-hexaenamidomethyl)pyrrolidin-1-yl)-4-oxobut-2-enoate (I-51);
(E)-methyl 4-(1-(4Z,7Z,10Z,13Z,16Z,19Z)-docosa-4,7,10,13,16,19-hexaenoylpiperidin-4-ylamino)-4-oxobut-2-enoate (I-52);
(E)-methyl 4-(4-(4Z,7Z,10Z,13Z,16Z,19Z)-docosa-4,7,10,13,16,19-hexaenamidopiperidin-1-yl)-4-oxobut-2-enoate (I-53);
(E)-methyl 4-((1-(4Z,7Z,10Z,13Z,16Z,19Z)-docosa-4,7,10,13,16,19-hexaenoylpiperidin-4-yl)methylamino)-4-oxobut-2-enoate (I-54);
(E)-methyl 4-(4-((4Z,7Z,10Z,13Z,16Z,19Z)-docosa-4,7,10,13,16,19-hexaenamidomethyl)piperidin-1-yl)-4-oxobut-2-enoate (I-55);
(E)-methyl 4-((1-(4Z,7Z,10Z,13Z,16Z,19Z)-docosa-4,7,10,13,16,19-hexaenoylpiperidin-2-yl)methylamino)-4-oxobut-2-enoate (I-56);
(E)-methyl 4-(2-((4Z,7Z,10Z,13Z,16Z,19Z)-docosa-4,7,10,13,16,19-hexaenamidomethyl)piperidin-1-yl)-4-oxobut-2-enoate (I-57);
(E)-methyl 4-((4-(4Z,7Z,10Z,13Z,16Z,19Z)-docosa-4,7,10,13,16,19-hexaenoylmorpholin-3-yl)methylamino)-4-oxobut-2-enoate (I-58);
(E)-methyl 4-(3-((4Z,7Z,10Z,13Z,16Z,19Z)-docosa-4,7,10,13,16,19-hexaenamidomethyl)morpholino)-4-oxobut-2-enoate (I-59);
(E)-methyl 4-(5-(4Z,7Z,10Z,13Z,16Z,19Z)-docosa-4,7,10,13,16,19-hexaenoyl-hexahydropyrrolo[3,4-c]pyrrol-2(1H)-yl)-4-oxobut-2-enoate (I-60);
(E)-methyl 4-(1-(4Z,7Z,10Z,13Z,16Z,19Z)-docosa-4,7,10,13,16,19-hexaenoyl-hexahydropyrrolo[3,4-b]pyrrol-5(1H)-yl)-4-oxobut-2-enoate (I-61);
(E)-methyl 4-((2-(4Z,7Z,10Z,13Z,16Z,19Z)-docosa-4,7,10,13,16,19-hexaenoyloctahydropyrrolo[1,2-a]pyrazin-7-yl)methylamino)-4-oxobut-2-enoate (I-62);
(E)-methyl 4-(7-((4Z,7Z,10Z,13Z,16Z,19Z)-docosa-4,7,10,13,16,19-hexaenamidomethyl)-hexahydropyrrolo[1,2-a]pyrazin-2(1H)-yl)-4-oxobut-2-enoate (I-63);
(E)-methyl 4-(4-((4Z,7Z,10Z,13Z,16Z,19Z)-docosa-4,7,10,13,16,19-hexaenamidomethyl)phenylamino)-4-oxobut-2-enoate (I-64);
(E)-methyl 4-(6-((4Z,7Z,10Z,13Z,16Z,19Z)-docosa-4,7,10,13,16,19-hexaenamidomethyl)pyridin-2-ylamino)-4-oxobut-2-enoate (I-65);
(E)-ethyl 4-(2-(4Z,7Z,10Z,13Z,16Z,19Z)-docosa-4,7,10,13,16,19-hexaenamidoethylamino)-4-oxobut-2-enoate (I-66);
(E)-ethyl 4-(2-((2-(4Z,7Z,10Z,13Z,16Z,19Z)-docosa-4,7,10,13,16,19-hexaenamidoethyl)(methyl)amino)ethylamino)-4-oxobut-2-enoate (I-67);
(E)-ethyl 4-(2-(2-(4Z,7Z,10Z,13Z,16Z,19Z)-docosa-4,7,10,13,16,19-hexaenamidoethylamino)ethylamino)-4-oxobut-2-enoate (I-68);
(S)-6-((4Z,7Z,10Z,13Z,16Z,19Z)-docosa-4,7,10,13,16,19-hexaenamido)-2-((E)-4-ethoxy-4-oxobut-2-enamido)hexanoic acid (I-69);
(S)-2-((4Z,7Z,10OZ,13Z,16Z,19Z)-docosa-4,7,10,13,16,19-hexaenamido)-6-((E)-4-ethoxy-4-oxobut-2-enamido)hexanoic acid (I-70);
(S)-6-((5Z,8Z,11Z,14Z,17Z)-icosa-5,8,11,14,17-pentaenamido)-2-((E)-4-methoxy-4-oxobut-2-enamido)hexanoic acid (I-71);
(S)-2-((5Z,8Z,11Z,14Z,17Z)-icosa-5,8,11,14,17-pentaenamido)-6-((E)-4-methoxy-4-oxobut-2-enamido)hexanoic acid (I-72);
(E)-methyl 4-(2-(2-(5Z,8Z,11Z,14Z,17Z)-icosa-5,8,11,14,17-pentaenamidoethylamino)ethylamino)-4-oxobut-2-enoate (I-73);
(E)-methyl 4-(2-((2-(5Z,8Z,11Z,14Z,17Z)-icosa-5,8,11,14,17-pentaenamidoethyl)(methyl)amino)ethylamino)-4-oxobut-2-enoate (I-74);
(E)-ethyl 4-(2-(5Z,8Z,11Z,14Z,17Z)-icosa-5,8,11,14,17-pentaenamidoethylamino)-4-oxobut-2-enoate (I-75);
(S)-2-((E)-4-ethoxy-4-oxobut-2-enamido)-6-((5Z,8Z,11Z,14Z,17Z)-icosa-5,8,11,14,17-pentaenamido)hexanoic acid (I-76);
(S)-6-((E)-4-ethoxy-4-oxobut-2-enamido)-2-((5Z,8Z,11Z,14Z,17Z)-icosa-5,8,11,14,17-pentaenamido)hexanoic acid (I-77);
(E)-ethyl 4-(2-((2-(5Z,8Z,11Z,14Z,17Z)-icosa-5,8,11,14,17-pentaenamidoethyl)(methyl)amino)ethylamino)-4-oxobut-2-enoate (I-78);
(E)-ethyl 4-(2-(2-(5Z,8Z,11Z,14Z,17Z)-icosa-5,8,11,14,17-pentaenamidoethylamino)ethylamino)-4-oxobut-2-enoate (I-79);

(S)-5-((4Z,7Z,10Z,13Z,16Z,19Z)-docosa-4,7,10,13,16,19-hexaenamido)-2-((E)-4-methoxy-4-oxobut-2-enamido)pentanoic acid (I-80);
(S)-2-((4Z,7Z,10Z,13Z,16Z,19Z)-docosa-4,7,10,13,16,19-hexaenamido)-5-((E)-4-methoxy-4-oxobut-2-enamido)pentanoic acid (I-81);
(S)-1,3-dihydroxypropan-2-yl 5-((4Z,7Z,10Z,13Z,16Z,19Z)-docosa-4,7,10,13,16,19-hexaenamido)-2-((E)-4-methoxy-4-oxobut-2-enamido)pentanoate (I-82);
(S)-1,3-dihydroxypropan-2-yl 2-((4Z,7Z,10Z,13Z,16Z,19Z)-docosa-4,7,10,13,16,19-hexaenamido)-5-((E)-4-methoxy-4-oxobut-2-enamido)pentanoate (I-83);
(S)-5-((5Z,8Z,11Z,14Z,17Z)-icosa-5,8,11,14,17-pentaenamido)-2-((E)-4-methoxy-4-oxobut-2-enamido)pentanoic acid (I-84);
(S)-2-((5Z,8Z,11Z,14Z,17Z)-icosa-5,8,11,14,17-pentaenamido)-5-((E)-4-methoxy-4-oxobut-2-enamido)pentanoic acid (I-85);
(S)-1,3-dihydroxypropan-2-yl 5-((5Z,8Z,11Z,14Z,17Z)-icosa-5,8,11,14,17-pentaenamido)-2-((E)-4-methoxy-4-oxobut-2-enamido)pentanoate (I-86);
(S)-1,3-dihydroxypropan-2-yl 2-((5Z,8Z,11Z,14Z,17Z)-icosa-5,8,11,14,17-pentaenamido)-5-((E)-4-methoxy-4-oxobut-2-enamido)pentanoate (I-87);
(S)-5-((4Z,7Z,10Z,13Z,16Z,19Z)-docosa-4,7,10,13,16,19-hexaenamido)-2-((E)-4-ethoxy-4-oxobut-2-enamido)pentanoic acid (I-88);
(S)-2-((4Z,7Z,10Z,13Z,16Z,19Z)-docosa-4,7,10,13,16,19-hexaenamido)-5-((E)-4-ethoxy-4-oxobut-2-enamido)pentanoic acid (I-89);
(S)-1,3-dihydroxypropan-2-yl 5-((4Z,7Z,10Z,13Z,16Z,19Z)-docosa-4,7,10,13,16,19-hexaenamido)-2-((E)-4-ethoxy-4-oxobut-2-enamido)pentanoate (I-90);
(S)-1,3-dihydroxypropan-2-yl 2-((4Z,7Z,10Z,13Z,16Z,19Z)-docosa-4,7,10,13,16,19-hexaenamido)-5-((E)-4-ethoxy-4-oxobut-2-enamido)pentanoate (I-91);
(S)-2-((E)-4-ethoxy-4-oxobut-2-enamido)-5-((5Z,8Z,11Z,14Z,17Z)-icosa-5,8,11,14,17-pentaenamido)pentanoic acid (I-92);
(S)-5-((E)-4-ethoxy-4-oxobut-2-enamido)-2-((5Z,8Z,11Z,14Z,17Z)-icosa-5,8,11,14,17-pentaenamido)pentanoic acid (I-93);
(S)-1,3-dihydroxypropan-2-yl 2-((E)-4-ethoxy-4-oxobut-2-enamido)-5-((5Z,8Z,11Z,14Z,17Z)-icosa-5,8,11,14,17-pentaenamido)pentanoate (I-94);
(S)-1,3-dihydroxypropan-2-yl 5-((E)-4-ethoxy-4-oxobut-2-enamido)-2-((5Z,8Z,11Z,14Z,17Z)-icosa-5,8,11,14,17-pentaenamido)pentanoate (I-95);
(S)-1,3-dihydroxypropan-2-yl 6-((5Z,8Z,11Z,14Z,17Z)-icosa-5,8,11,14,17-pentaenamido)-2-((E)-4-methoxy-4-oxobut-2-enamido)hexanoate (I-96);
(S)-1,3-dihydroxypropan-2-yl 2-((5Z,8Z,11Z,14Z,17Z)-icosa-5,8,11,14,17-pentaenamido)-6-((E)-4-methoxy-4-oxobut-2-enamido)hexanoate (I-97);
(S)-1,3-dihydroxypropan-2-yl 6-((4Z,7Z,10Z,13Z,16Z,19Z)-docosa-4,7,10,13,16,19-hexaenamido)-2-((E)-4-ethoxy-4-oxobut-2-enamido)hexanoate (I-98);
(S)-1,3-dihydroxypropan-2-yl 2-((E)-4-ethoxy-4-oxobut-2-enamido)-6-((5Z,8Z,11Z,14Z,17Z)-icosa-5,8,11,14,17-pentaenamido)hexanoate (I-99);
(S)-1,3-dihydroxypropan-2-yl 2-((4Z,7Z,10Z,13Z,16Z,19Z)-docosa-4,7,10,13,16,19-hexaenamido)-6-((E)-4-ethoxy-4-oxobut-2-enamido)hexanoate (I-100);
(S)-1,3-dihydroxypropan-2-yl 6-((E)-4-ethoxy-4-oxobut-2-enamido)-2-((5Z,8Z,11Z,14Z,17Z)-icosa-5,8,11,14,17-pentaenamido)hexanoate (I-101);
(E)-4-(2-(4Z,7Z,10Z,13Z,16Z,19Z)-docosa-4,7,10,13,16,19-hexaenamidoethylamino)-4-oxobut-2-enoic acid (I-102);
2-(4Z,7Z,10Z,13Z,16Z,19Z)-docosa-4,7,10,13,16,19-hexaenamidoethyl methyl fumarate (I-103);
(E)-methyl 4-(methyl(2-((4Z,7Z,10Z,13Z,16Z,19Z)—N-methyldocosa-4,7,10,13,16,19-hexaenamido)ethyl)amino)-4-oxobut-2-enoate (I-104);
(R,E)-methyl 4-(2-(5-(1,2-dithiolan-3-yl)pentanamido)ethylamino)-4-oxobut-2-enoate (I-105);
6-(5-((R)-1,2-dithiolan-3-yl)pentanamido)-2-((E)-4-methoxy-4-oxobut-2-enamido)hexanoic acid (I-106);
2-(5-((R)-1,2-dithiolan-3-yl)pentanamido)-6-((E)-4-methoxy-4-oxobut-2-enamido)hexanoic acid (I-107);
(R,E)-methyl 4-(2-(2-(5-(1,2-dithiolan-3-yl)pentanamido)ethylamino)ethylamino)-4-oxobut-2-enoate (I-108);
(R,E)-methyl 4-(2-((2-(5-(1,2-dithiolan-3-yl)pentanamido)ethyl)(methyl)amino)ethylamino)-4-oxobut-2-enoate (I-109);
$N^1$, $N^4$-bis(2-(4Z,7Z,10Z,13Z,16Z,19Z)-docosa-4,7,10,13,16,19-hexaenamidoethyl)fumaramide (II-1); and
$N^1$-(2-(4Z,7Z,10Z,13Z,16Z,19Z)-docosa-4,7,10,13,16,19-hexaenamidoethyl)-N4-(2-(5Z,8Z,11Z,14Z,17Z)-icosa-5,8,11,14,17-pentaenamidoethyl)fumaramide (II-2).

Methods for Using Fatty Acid Fumarate Derivatives

Also provided in the invention is a method for inhibiting, preventing, or treating inflammation or an inflammatory disease in a subject. The inflammation can be associated with an inflammatory disease or a disease where inflammation contributes to the disease. Inflammatory diseases can arise where there is an inflammation of the body tissue. These include local inflammatory responses and systemic inflammation. Examples of such diseases include, but are not limited to: organ transplant rejection; reoxygenation injury resulting from organ transplantation (see Grupp et al., J. Mol. Cell Cardiol. 31: 297-303 (1999)) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, chronic obstructive airway disease, and cystic fibrosis; inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; chronic kidney disease (CKD); IgA nephropathy; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis. Metabolic disease such as type II diabetes mellitus; the prevention of type I diabetes; dyslipedemia; hypertriglyceridemia; diabetic complications, including, but not limited to glaucoma, retinopathy, macula edema, nephropathy, such as microalbuminuria and progressive diabetic nephropathy, polyneuropathy, diabetic neuropathy, atherosclerotic coronary arterial disease, peripheral arterial disease, nonketotic hyperglycemichyperosmolar coma, mononeuropathies, autonomic neuropathy, joint problems, and a skin or mucous membrane complication, such as an infection, a shin spot, a candidal infection or necrobiosis lipoidica diabeticorum; immune-complex vasculitis, systemic lupus erythematosus; inflammatory diseases of the heart such as cardiomyopathy, ischemic heart disease hypercholesterolemia, and atherosclerosis; as well as various other diseases that can have significant inflammatory components, including preeclampsia; chronic liver failure, brain and spinal cord trauma, and cancer. The inflammatory disease can also be a systemic inflammation of the body, exemplified by gram-positive or gram negative shock, hemorrhagic or anaphylactic shock, or shock induced by cancer chemotherapy in response to proinflammatory cytokines, e.g., shock associated with proinflammatory cytokines. Such shock can be induced, e.g., by a chemotherapeutic agent that is administered as a treatment for cancer. Other disorders include depression, obesity, allergic diseases, acute cardiovascular events, arrhythmia, prevention of sudden death, muscle wasting diseases such as Duchenne's Muscular Dystrophy, inflammatory myopathies such as dermatomositis, inclusion body myositis, and polymyositis, and cancer cachexia. Also inflammation that results from surgery and trauma can be treated with a Fatty Acid Fumarate Derivative.

The compounds described herein are also useful in treating a variety of cancers such as carcinoma, sarcoma, lymphoma, leukemia, melanoma, mesothelioma, multiople myeloma, seminoma, and cancer of the bladder, blood, bone, brain, breast, central nervous system, colon, endometrium, esophagus, genitourinary tract, head, larynx, liver, lung, neck, ovary, pancreas, prostate, testicle, spleen, small intestine, large intestine or stomach.

In some embodiments, the subject is administered an effective amount of a Fatty Acid Fumarate Derivative.

Effective dosage amounts of the present invention, when used for the indicated effects, range from about 20 mg to about 5000 mg of the Fatty Acid Fumarate Derivative per day. Compositions for in vivo or in vitro use can contain about 20, 50, 75, 100, 150, 250, 500, 750, 1000, 1250, 2500, 3500, or 5000 mg of the Fatty Acid Fumarate Derivative. In one embodiment, the compositions are in the form of a tablet that can be scored. Effective plasma levels of the Fatty Acid Fumarate Derivative can range from about 0.002 mg to about 100 mg per kg of body weight per day. Appropriate dosages of the Fatty Acid Fumarate Derivatives can be determined as set forth in Goodman, L. S.; Gilman, A. *The Pharmacological Basis of Therapeutics,* 5th ed.; MacMillan: New York, 1975, pp. 201-226.

The invention also includes pharmaceutical compositions useful for treating or preventing a metabolic disorder, or for inhibiting a metabolic disorder, or more than one of these activities. The compositions can be suitable for internal use and comprise an effective amount of a Fatty Acid Fumarate Derivative and a pharmaceutically acceptable carrier. The Fatty Acid Fumarate Derivatives are especially useful in that they demonstrate very low peripheral toxicity or no peripheral toxicity.

Administration of the Fatty Acid Fumarate Derivatives can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a Fatty Acid Fumarate Derivative and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the Fatty Acid Fumarate Derivative is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the Fatty Acid Fumarate Derivatives.

The Fatty Acid Fumarate Derivatives can be also formulated as a suppository that can be prepared from fatty emulsions or suspensions; using polyalkylene glycols such as propylene glycol, as the carrier.

The Fatty Acid Fumarate Derivatives can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Fatty Acid Fumarate Derivatives can also be delivered by the use of monoclonal antibodies as individual carriers to which the Fatty Acid Fumarate Derivatives are coupled. The Fatty Acid Fumarate Derivatives can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Fatty Acid Fumarate Derivatives can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, Fatty Acid Fumarate Derivatives are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 80%, from about 5% to about 60%, or from about 1% to about 20% of the Fatty Acid Fumarate Derivative by weight or volume.

The dosage regimen utilizing the Fatty Acid Fumarate Derivative is selected in accordance with a variety of factors including type, species, age, weight, sex and medical condition of the patient; the severity of the condition to be treated; the route of administration; the renal or hepatic function of the patient; and the particular Fatty Acid Fumarate Derivative employed. A physician or veterinarian of ordinary skill in the art can readily determine and prescribe the effective amount of the drug required to prevent, counter or arrest the progress of the condition.

Fatty Acid Fumarate Derivatives can be administered in a single daily dose, or the total daily dosage can be administered in divided doses of two, three or four times daily. Furthermore, Fatty Acid Fumarate Derivatives can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the Fatty Acid Fumarate Derivative ranges from about 0.1% to about 15%, w/w or w/v.

Methods for Making the Fatty Acid Fumarate Derivatives

Examples of synthetic pathways useful for making Fatty Acid Fumarate Derivatives of Formula I, IA, IB, IC, and II are set forth in the Examples below and generalized in Schemes 1-11.

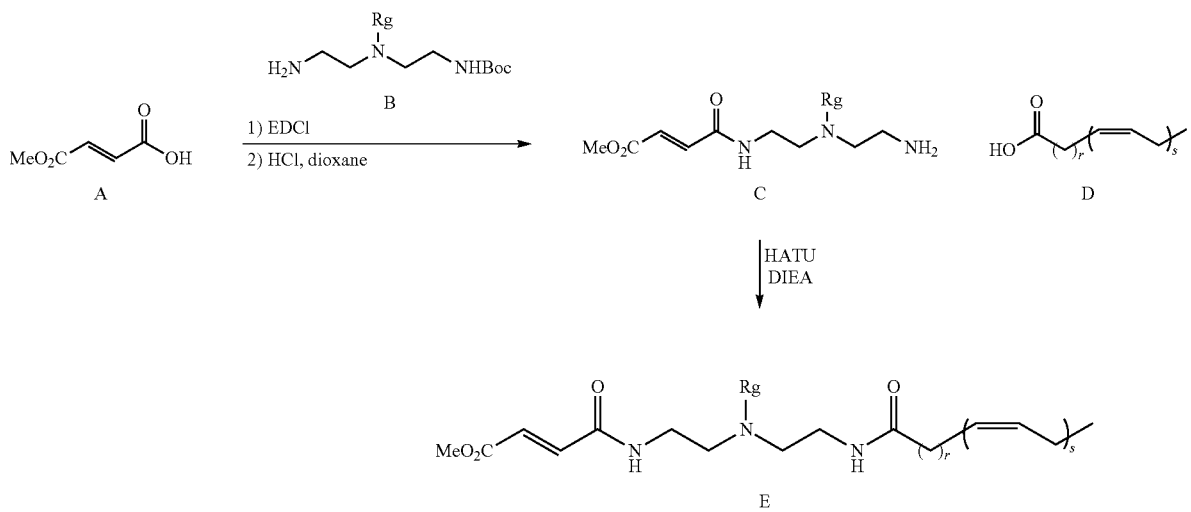

Scheme 1

The mono-BOC protected amine of the Formula B can be obtained from commercial sources or prepared according to the procedures outlined in Krapcho et al, *Synthetic Communications* 1990, 20, p. 2559-2564. The commercially available compound A can be amidated with the amine B using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound C. Activation of compound C with a coupling agent such as HATU in the presence of an amine such as DIEA followed by addition of a fatty acid of Formula D affords compounds of the Formula E. Those skilled in the art will recognize that lipoic acid can be substituted for fatty acid D in this and subsequent schemes.

Scheme 2

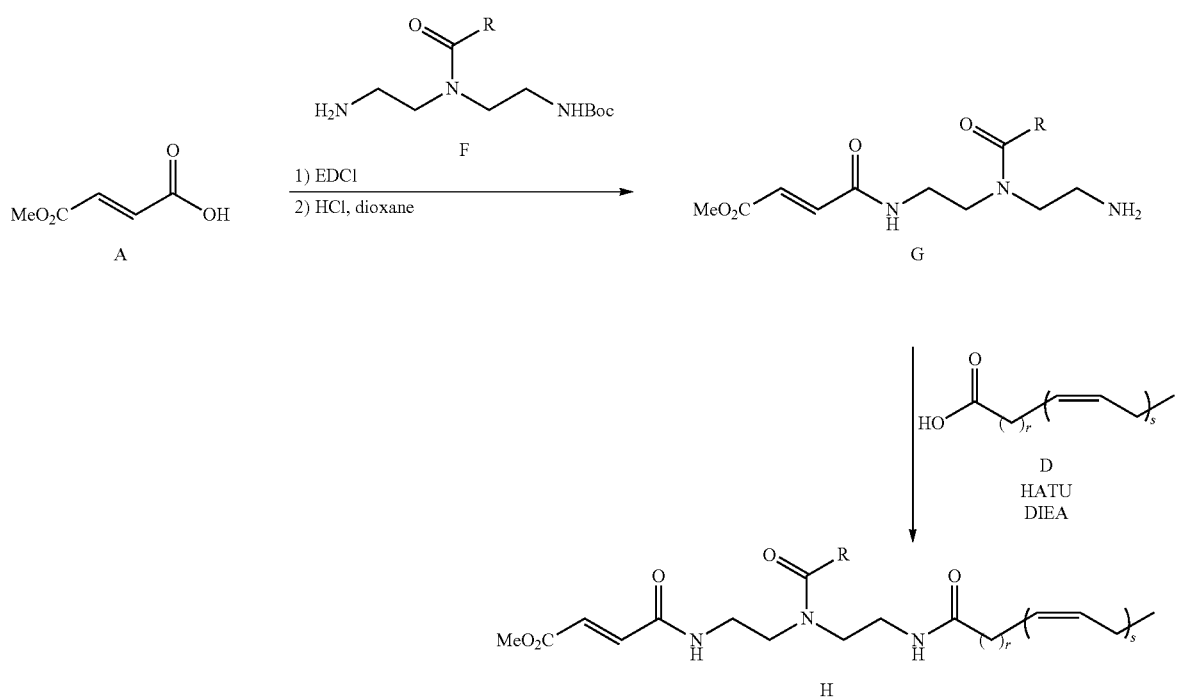

The acylated amine of the Formula F can be prepared using the procedures outlined in Andruszkiewicz et al, *Synthetic Communications,* 2008, 38, p. 905-913. Compound A can be amidated with the amine F using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound G. Activation of compound G with a coupling agent such as HATU in the presence of an amine such as DIEA followed by addition of a fatty acid of Formula D affords compounds of the Formula H.

Scheme 3

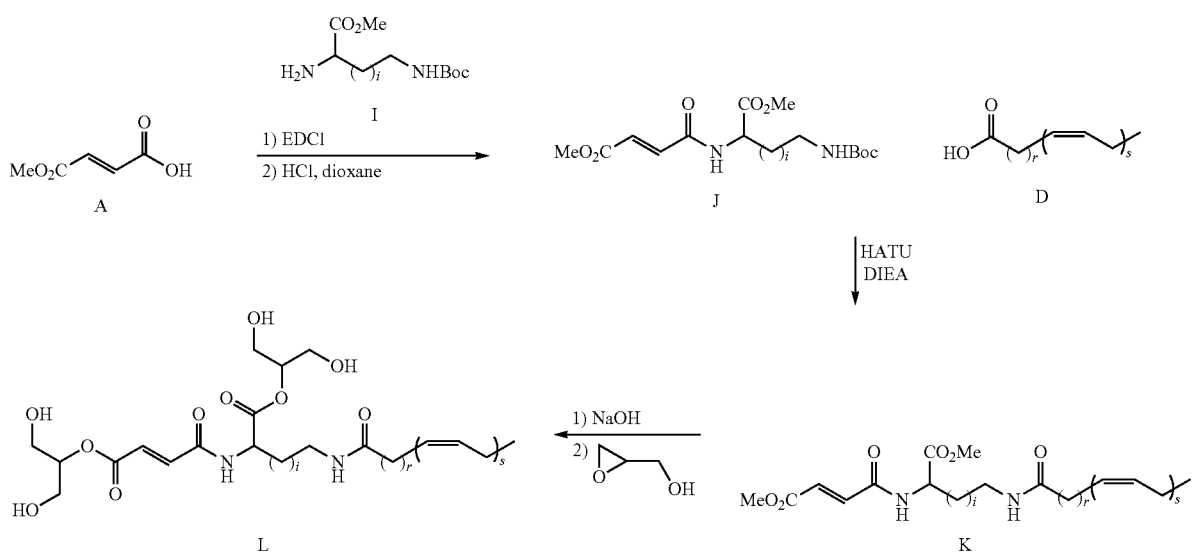

Compound A can be amidated with the corresponding amine I (where i=0, 1, 2 or 3) using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound J. Activation of compound J with a coupling agent such as HATU in the presence of an amine such as DIEA followed by addition of a fatty acid of Formula D affords compounds of the Formula K. Hydrolysis of the ester under basic conditions such as NaOH or LiOH produces the corresponding acid, which can be coupled with glycidyl to afford compounds of the Formula L.

coupling reagent such as DCC, CDI, EDC, or optionally with a tertiary amine base and/or catalyst, e.g., DMAP, followed by deprotection of the BOC group with acids such as TFA or HCl in a solvent such as CH$_2$Cl$_2$ or dioxane to produce the coupled compound N. Activation of compound N with a

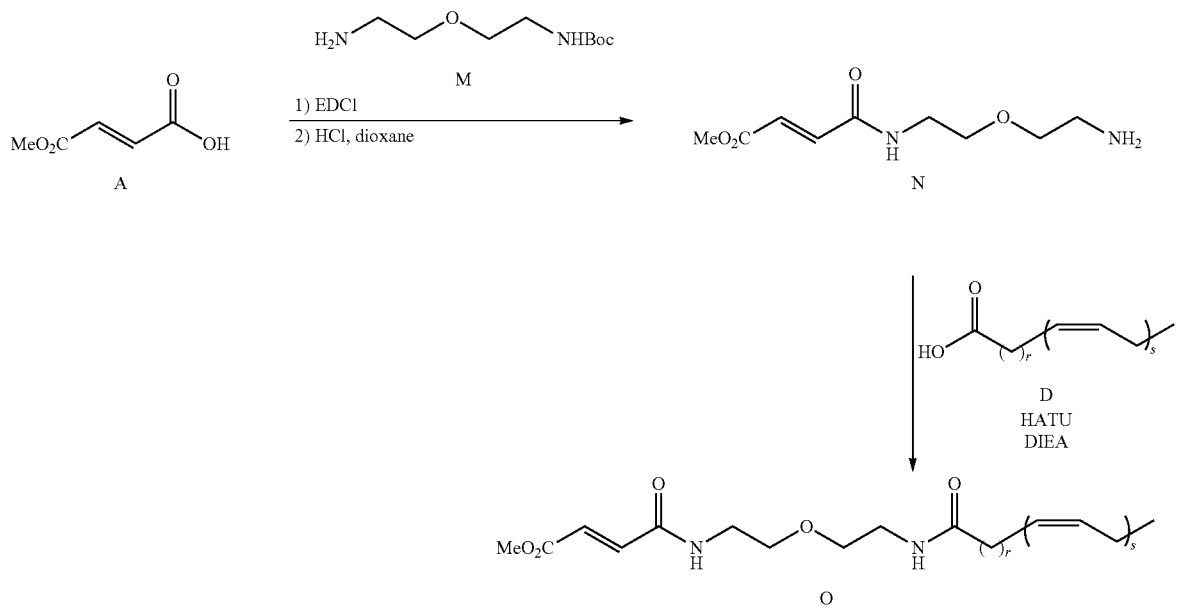

Scheme 4

The amine M can be prepared according to the procedures outlined in Dahan et al, *J. Org. Chem.* 2007, 72, p. 2289-2296. Compound A can be coupled with the amine M using a coupling agent such as HATU in the presence of an amine such as DIEA followed by addition of a fatty acid of Formula D affords compounds of the Formula O.

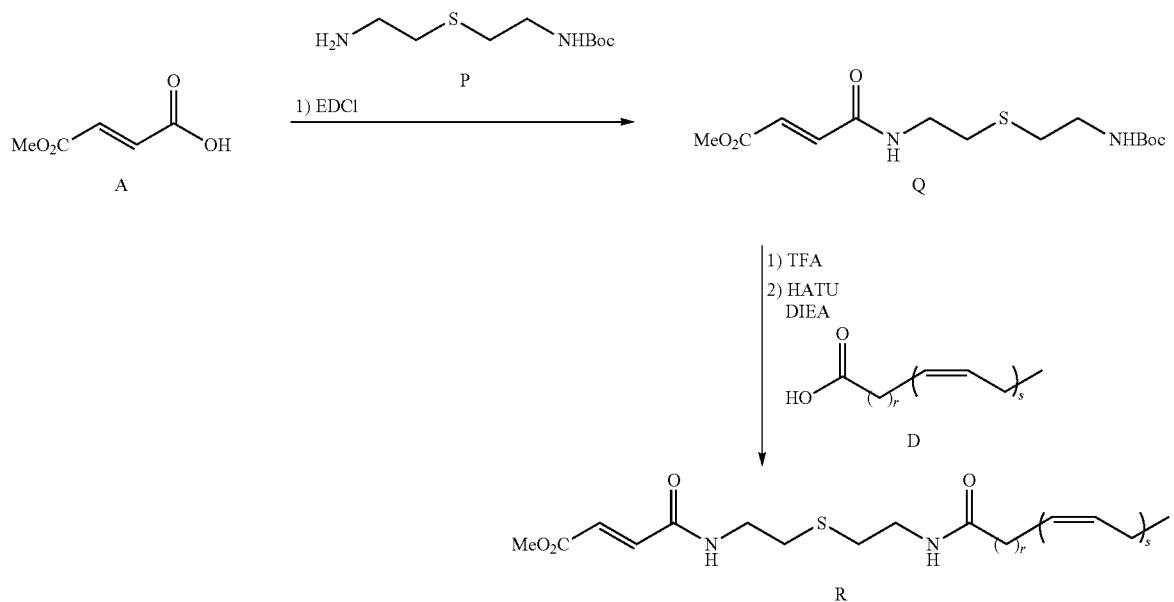

Scheme 5

Compound A can be amidated with the commercially available amine P using a coupling reagent such as DCC, CDI, EDC, or optionally with a tertiary amine base and/or catalyst, e.g., DMAP, to afford compound Q. The BOC group in compound Q can be removed with acids such as TFA or HCl in a solvent such as $CH_2Cl_2$ or dioxane and the resulting amine can be coupled with a fatty acid of Formula D using a coupling agent such as HATU in the presence of an amine such as DIEA to afford compounds of the Formula R. To those familiar in the art, the sulfur group in Formula Q can be oxidized to the corresponding sulfoxide or sulfone using an oxidizing agent such as $H_2O_2$ or oxone.

amidated with the amine T using a coupling reagent such as DCC, CDI, EDC, or optionally with a tertiary amine base and/or catalyst, e.g., DMAP, to afford compound U. The BOC group of compound U can be removed with acids such as TFA or HCl in a solvent such as $CH_2Cl_2$ or dioxane and the resulting amine can be coupled with a fatty acid of Formula D using HATU in the presence of an amine such as DIEA to afford compounds of the Formula V. To those familiar in the art, the hydroxyl group in compound U can be further acylated or converted to an amino group by standard mesylation chemistry followed by displacement with sodium azide and hydrogenation over a catalyst such as Palladium on carbon. The amine can be further acylated or alkylated, followed by the

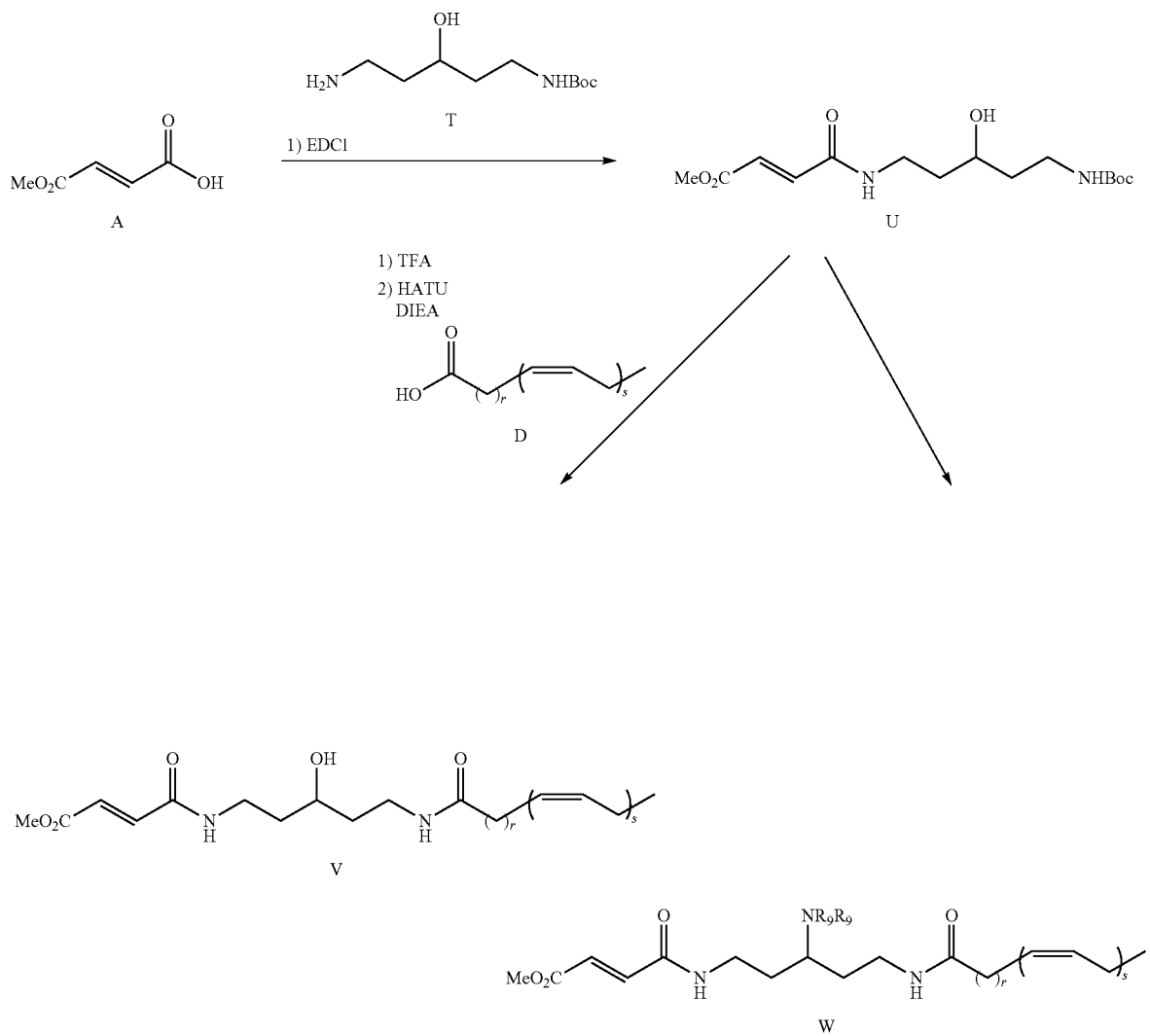

Scheme 6

The amine T can be prepared from the commercially available diamine according to the procedures outlined in Dahan et al, *J. Org. Chem.* 2007, 72, p. 2289-2296. Compound A can be removal of the BOC group. The resulting amine can be coupled with a fatty acid of the Formula D to afford compounds of the Formula W.

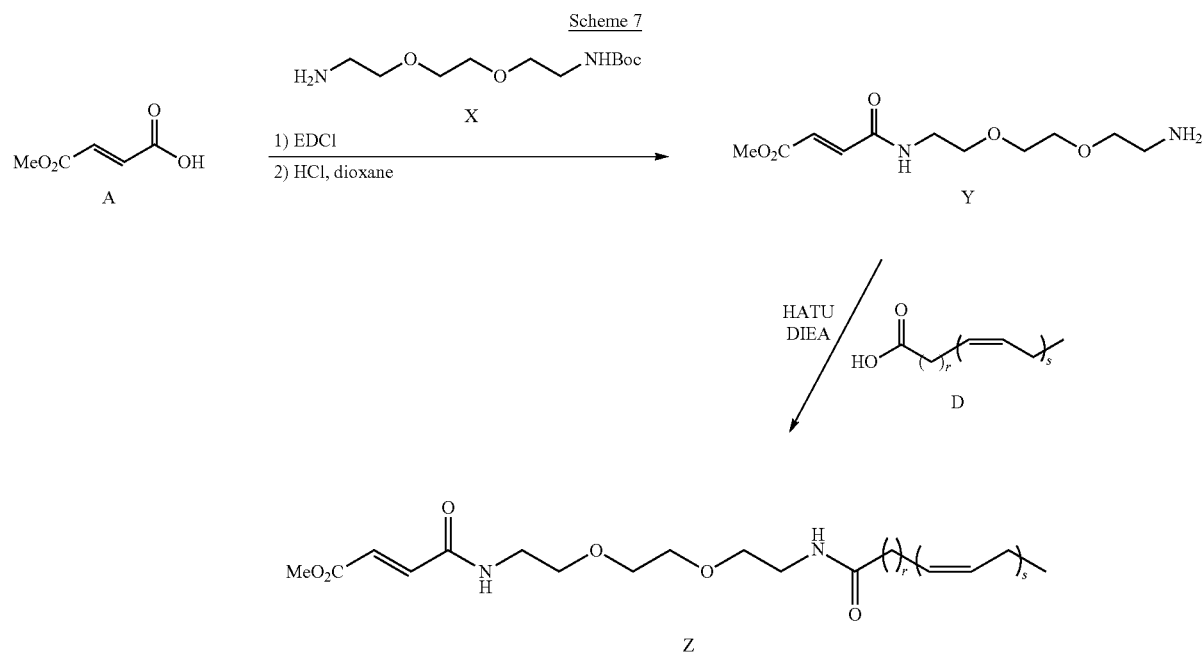

Compound A can be amidated with the commercially available amine X using a coupling reagent such as DCC, CDI, EDC, optionally with a tertiary amine base and/or catalyst, e.g., DMAP to afford compound Y. The BOC group in compound Y can be removed with acids such as TFA or HCl in a solvent such as $CH_2Cl_2$ or dioxane. The resulting amine can be coupled with a fatty acid of the Formula D using a coupling agent such as HATU in the presence of an amine such as DIEA to afford compounds of the Formula Z.

Compound A can be amidated with the commercially available cysteine methyl ester using a coupling reagent such as DCC, CDI, EDC, or optionally with a tertiary amine base and/or catalyst, e.g., DMAP, to afford compound AA. The commercially available maleimide derivative BB can be coupled with a fatty acid of the Formula D using a coupling agent such as HATU or EDCI to afford compounds of the Formula CC. Compound AA can be coupled to compounds of the Formula CC in a solvent such as acetonitrile to afford compounds of the Formula DD.

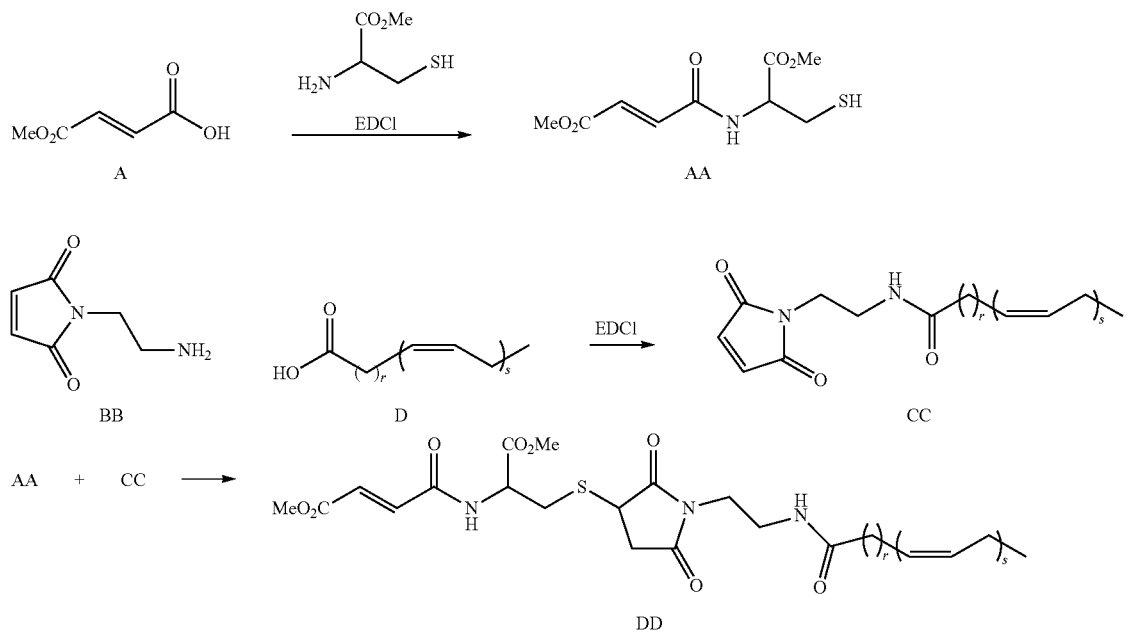

Scheme 9

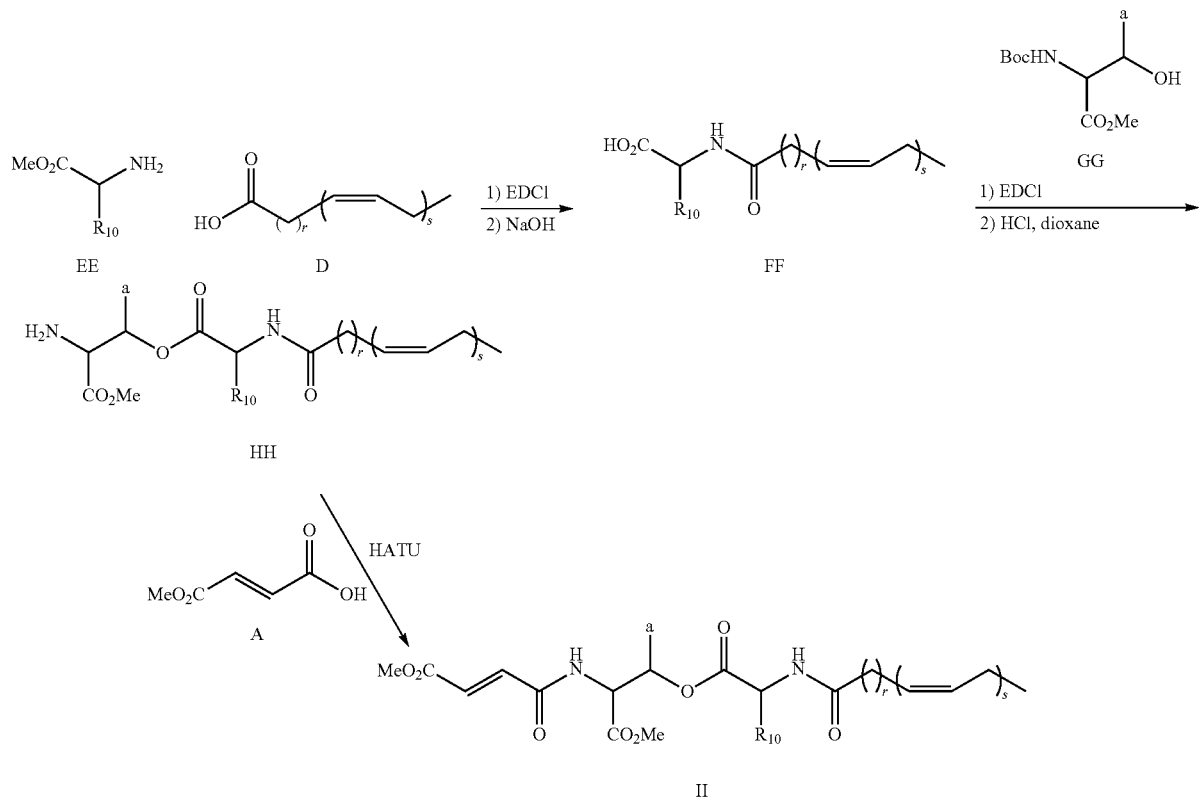

The commercially available amino acid esters EE can be coupled with a fatty acid of the Formula D using a coupling agent such as EDCI or HATU, followed by alkaline hydrolysis of the methyl ester to afford compounds of the Formula FF. Compounds of the Formula FF can be coupled with the commercially available BOC-amino acid derivatives GG using a coupling agent such as EDCI or HATU. The BOC group can be removed by treatment with acids such as TFA or HCl to afford compounds of the Formula HH which can then be coupled with compound A to afford compounds of the Formula II.

Scheme 10

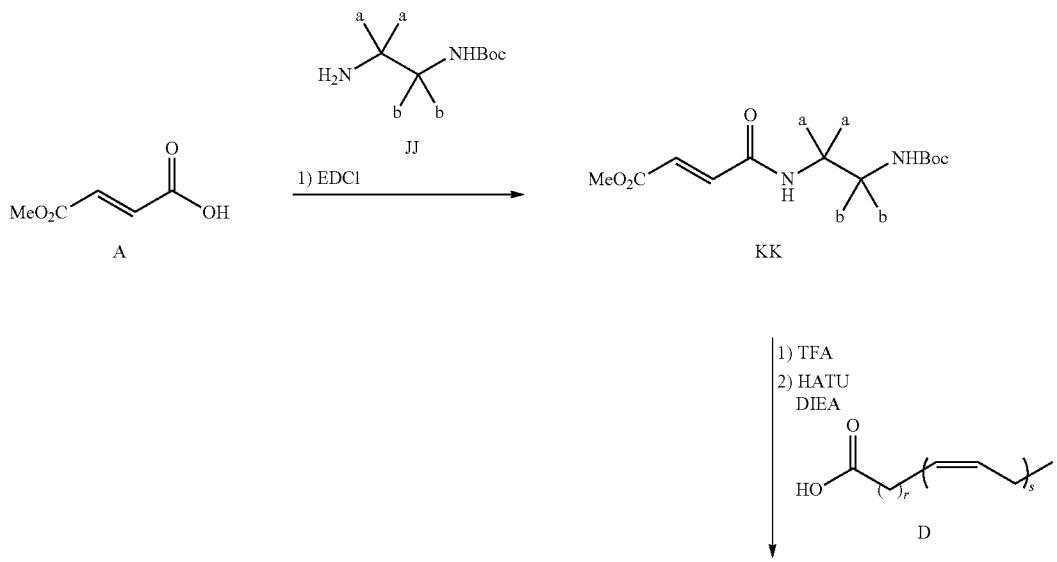

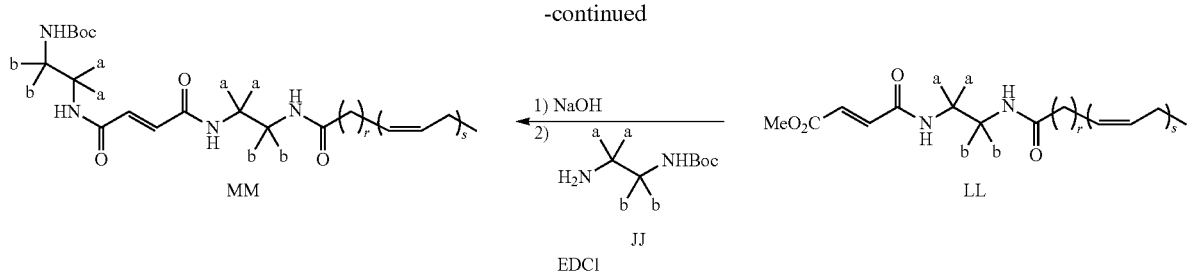

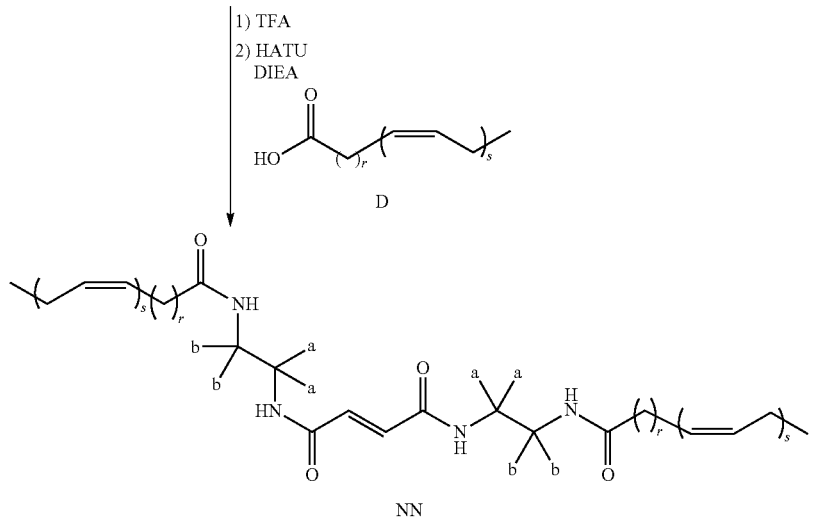

Compound A can be coupled with the amine of Formula JJ using either EDCI or HATU to afford compounds of the Formula KK. The BOC group can be removed by treatment with acids such as TFA or HCl and the resulting amine can be coupled with a fatty acid of Formula D to afford compound LL. The methyl ester group can be hydrolyzed by treatment with a base such as LiOH or NaOH and the resulting acid can be coupled with the amine JJ to afford compound MM. The BOC group can be removed by treatment with acids such as TFA or HCl and the resulting amine can be coupled with a fatty acid of Formula D using either EDCI or HATU to afford compound NN.

Scheme 11

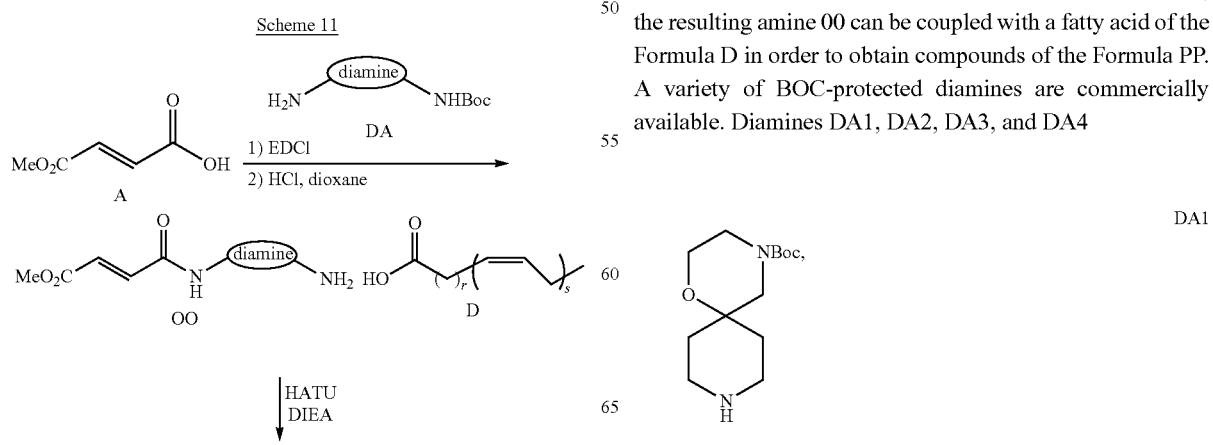

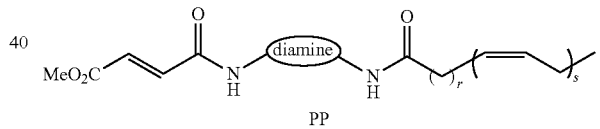

Compound A can be coupled with a BOC-protected diamine of the general Formula DA to obtain the BOC-protected amide derivative. After treatment with HCl in dioxane, the resulting amine OO can be coupled with a fatty acid of the Formula D in order to obtain compounds of the Formula PP. A variety of BOC-protected diamines are commercially available. Diamines DA1, DA2, DA3, and DA4

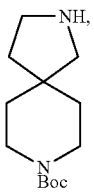

DA2

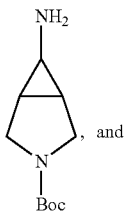

DA3

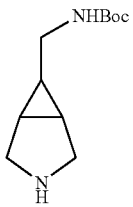

DA4 and derivatives thereof, can be prepared according to the procedures outlined in the corresponding references: diamine DA1, Stocks et al, *Bioorganic and Medicinal Chemistry Letters* 2010, p. 7458; diamine DA2, Fritch et al, *Bioorganic and Medicinal Chemistry Letters* 2010, p. 6375; diamine DA3 and DA4, Moffat et al, *J. Med. Chem.* 2010, 53, p. 8663-8678), the disclosures of the foregoing references are incorporated herein in their entireties. Detailed procedures to prepare a variety of mono-protected diamines can also be found in the following references: WO 2004092172, WO 2004092171, and WO 2004092173, the disclosures of which are incorporated herein in their entireties.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Effects of Compounds of the Invention on NfκB Levels in RAW 264.7 Macrophages

RAW 264.7 cells stably expressing a 3× NFkB response element-drive luciferase reporter were seeded into 96 well plates in sera-free medium (Optimem) 18 hours prior to compound application. Compounds of the invention were prepared by first making 100 mM stock solutions in EtOH. Stock solutions were then diluted 1:100 in low LPS FBS (Gemini BenchMark 100-106), mixed vigorously and allowed to incubate at room temperature for 30 minutes. 1:2 serial dilutions were then made in FBS supplemented with 1% EtOH, mixed vigorously, and again allowed to incubate at room temperature for 30 minutes before adding to RAW 264.7 reporter cells (final concentrations: 10% FBS, 100 uM highest compound dilution, 0.1% EtOH) for a 2 hour pretreatment prior to stimulation with LPS. Cells were then stimulated with 200 ng/ml LPS or vehicle control for 3 hours in the presence of the compounds of the invention. A set of six vehicles was left unstimulated with LPS in order to measure the assay floor. AlamarBlue viability dye (Invitrogen) was added to cells simultaneously with the delivery of LPS (final AlamarBlue concentration of 10%). After the 3 h incubation period with LPS, cell viability was measured by reading fluorescence (excitation 550 nm, emission 595 nm) with a Perkin Elmer Victor V plate reader. Then cell media was aspirated from each well. Luciferase signal was then developed by addition of the Britelite Plus reagent (Perkin Elmer). Luciferase activity was measured with the Perkin Elmer Victor V plate reader. NF-κB activity was expressed as a percent of the vehicle control wells (stimulated with LPS). Compounds were tested at 6 dose point titrations in triplicate to determine $IC_{50}$ values.

Table 1 summarizes the IC50 values for a number of fatty acid fumarate conjugates in this NF-κB luciferase reporter assay. In this table, MMF=mono methyl fumarate. A (−) indicates that the compound showed no inhibitory activity≤200 μM. A (+) indicates that the compound showed inhibitory activity between >50 μM and ≤200 μM. A (++) indicates that the compound showed inhibitory activity at ≤50 μM.

TABLE 1

| Compound | NF-kB inhibitory activity |
|---|---|
| MMF | − |
| MMF + DHA | − |
| I-1 | ++ |
| I-2 | ++ |
| I-3 | ++ |
| I-4 | ++ |
| I-5 | + |
| I-6 | ++ |
| I-22 | ++ |
| I-39 | + |
| I-40 | ++ |
| I-41 | + |
| I-66 | + |
| I-67 | ++ |
| I-72 | + |
| I-102 | − |
| I-103 | + |
| I-104 | − |

Example 2

Effect of Fatty Acid Fumarate Derivatives on IL-1β and TNF-α

RAW264.7 macrophages were seeded at a density of 100,000 cells/well in a 96-well plate in DMEM supplemented with 10% FBS and Penn/strep. 16 hours later, medium was aspirated and replaced with 90 μL/well of serum-free DMEM. A fatty acid fumarate conjugate, DHA and monomethyl-fumarate (MMF) were brought up in 100% EtOH to a concentration of 100 mM and then diluted 1:100 in 100% FBS for a stock solution consisting of 1 mM compound and 1% EtOH. These stock solutions were then diluted 1:10 in FBS supplemented with 1% EtOH to generate a 100.M of a fatty acid fumarate conjugate and 100 μM each of DHA and MMF. 10 μL was then added to the RAW246.7 cells to generate final concentrations 10M of the fatty acid fumarate conjugate or 10M each DHA and MMF, along with vehicle only control. The compounds were allowed to pre-incubate for 2 hours before stimulation of 100 ng/ml LPS (10 μL of 1 μg/ml LPS was added to each well). Following 3 hours of LPS stimulation, cells were washed once in 1×PBS, aspirated dry, and flash frozen in liquid nitrogen. RNA was then isolated and converted to cDNA using the Cells to cDNA kit (Ambion) according to the manufacturer's protocol. IL-1β and TNF-α transcript levels were then measured using Taqman primer/probe assay sets (Applied Biosystems), normalized to GAPDH using the deltaCt method, and the data expressed relative to vehicle only control. Macrophages treated with compound I-1 showed greater reduction of IL-1β and TNF-α gene expression than cells that were treated with a combination of mono methyl fumarate (MMF) and DHA (FIG. 1). Statistical analysis was conducted using one-way ANOVA, p<0.05, *p<0.005.

Example 3

TNFα Release Assay in RAW 264.7 Macrophages

The purpose of this assay is to measure the ability of small molecules to inhibit the secretion of TNFα in cultured macrophages stimulated with lipopolysaccharide (LPS). Treatment of macrophages with LPS activates inflammatory cytokine pathways primarily through the TLR4-NFκB signaling axis. Compounds of the invention inhibit the transcriptional activation of NFκB and thus decrease the production and release of TNFα Dexamethasone, a potent agonist of the glucocorticoid receptor is used a positive control for inhibition of TNFα release.

Day 1: Seed RAW 264.7 macrophages into 96 well culture plates. Remove culture media from RAW 264.7 cell growing in a 75 mm² tissue culture flask (cells should be at ~70% confluence) and add 10 mL of warmed complete growth media (DMEM+10% FBS+1× pen/step). The cells are scraped into suspension using a sterile plate scraper and homogenized by pipetting up and down with a 10 mL serological pipette. The cell concentration is determined using a clinical hematoctyometer. Cells are then diluted to 150,000 cells per mL into growth media. The diluted cells are then transferred to a sterile reagent reservoir and 100 μl of cell suspension is pipetted into each well of a 96 well culture plate using a multichannel pipette (15,000 cells/well). Plates are then incubated at 37° C. under normal tissue culture growth conditions (37° C., humidified $CO_2$ chamber).

Day 2: The test compound sample plate is prepared. Test compounds are prepared in growth media. Compounds are delivered to media from 1000× stocks in 100% DMSO (e.g. for a 10 M final concentration of test compound, deliver 2 μl of 10 mM test compound to 2 mL of media). At least 150 μl of 1× compound in media is added to 96 well sample plate. The perimeter wells of the 96 well plate are not used to avoid edge effects. Twelve sample wells are prepared with media plus 0.1% DMSO (these samples will serve as the vehicle controls; LPS-stimulated and non-stimulated; 10 μM dexamethasone is used as a positive control). Culture plates are then returned to the growth incubator for 2 hours. Cells are stimulated afterwards by adding 25 1 of 50 ng/mL LPS is added to every well (except the 6 unstimulated vehicle control wells: final concentration of 10 ng/mL LPS. Plates are returned to growth incubator for 3 hours. Afterwards, 100 μl of media supernatant is removed and transferred to a 96 well v-bottom sample plate. The media supernatant plate is centrifuged for 5 minutes at 1,000 rpm in a swing-bucket centrifuge, pelleting any cellular debris that may remain in supernatant. 80 μl of supernatant is removed from sample plate and transferred to a fresh v-bottom 96 well plate. Cell viability is measured using Celltiter-glo kit. By measuring cell viability, a given compound's effects on TNFα secretion can determine whether effects are due to cytotoxicity or to true inhibition of inflammatory signaling. Add 100 μl of Celltiter-glo reagent to each well of the cell culture plate and afterwards measure the luminescence signal (CPS) of the plate using the Victor 5 plate reader (0.3 second read; 60 second plate shaking prior to read). Cell viability of a given compound at a given concentration is computed as follows:

Cell viability=CPS Sample/(Average CPS unstimulated controls)*100

Use 20 μl of media supernatant per well for TNFα ELISA. Follow Invitrogen/Biosource manufacture's protocol for the mouse TNFα ELISA. Chromogen development is typically conducted for 20-30 minutes as described in the manufacturer's protocol. After addition of stop solution, measure OD 450 nm using the Victor 5 plate reader (0.1 second/well scan). Determine the TNFα secretion percent of control. The following formula is used to determine the TNFα secretion percent of control:

$$\frac{100 \times (OD450 \text{ nm Sample } X) - (\text{Average } OD450 \text{ nm unstimulated vehicle controls})}{(\text{Average } OD450 \text{ nm } LPS \text{ stimulated vehicle controls}) - (\text{Average } OD450 \text{ nm unstimulated vehicle controls})}$$

For each test compound, TNFα secretion percent of control can be plotted as a function of compound concentration using a four parameter dose-response curve fit equation (XLFIT Model #205):

$fit=(A+((B-A)/(1+((C/x)^D))))$ $inv=(C/((((B-A)/(y-A))-1)^(1/D)))$ $res=(y-fit)$ Example 4

Figure 2:
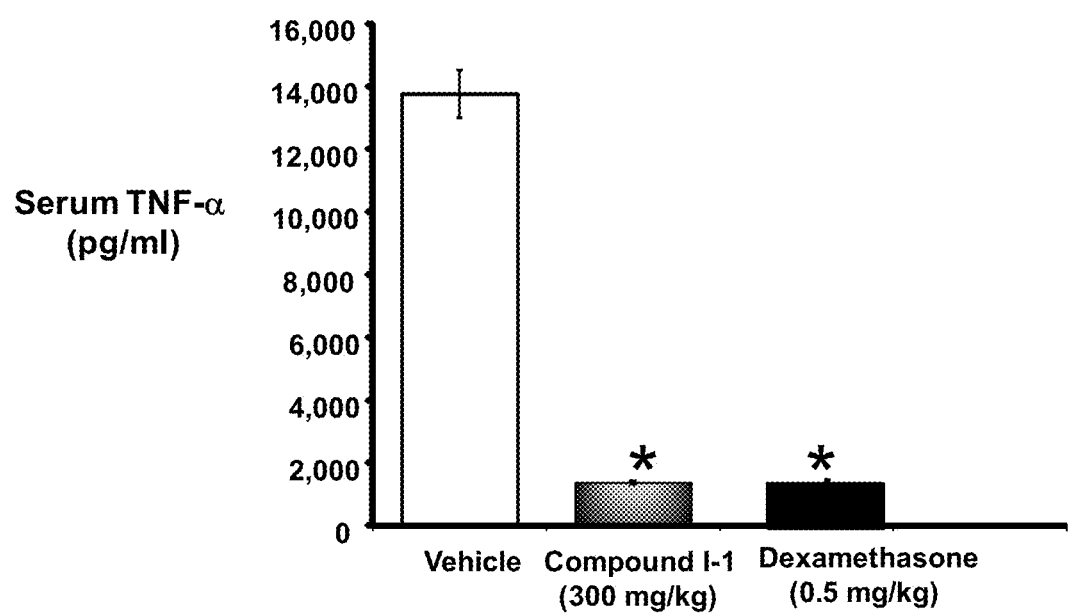
FIG. 2 is a graphical representation of the Serum TNF-α level of Male Swiss Webster mice that have been dosed with either compound I-1 or dexamethasone 90 minutes prior to challenge with LPS.

In Vivo Effects of Compounds of the Invention in an LPS-Challenge TNFα Mouse Model To measure the effects of compounds on TNFα secretion in vivo, Male Swiss Webster mice (n=10 animals per group) are dosed by either oral gavage or by ip injection with each test compound (dosing volume is 15 mL/kg). All compounds are formulated in the appropriate vehicles (Examples of vehicles that can be used include combinations of solvents such as polyethylene glycol and propyleneglycol, lipids such as glycerol monooleate and soybean oil, and surfactants such as polysorbate 80 and cremophor EL). Ninety minutes after compound dosing, animals are treated with 0.2 mg/kg LPS (lipopolysaccharide) by intraperitoneal (IP) injection. Ninety minutes after LPS challenge, mice are anesthetized and bled by cardiac puncture into serum separator tubes (with sodium heparin). Bleeds are allowed to clot at room temperature for 2 hours, and tubes are then spun for 20 minutes at 2,000×g. Serum is harvested from tubes (100-150 μl per animal) and frozen at −70° C. TNFα serum levels are measured using commercially available TNFα ELISA kits (*p<0.05 using a 2-tailed t-test). As a representative example, compound I-1 was dosed by at 300 mg/kg (i.p., formulated at 300 mg/g of compound in 42% Tween, 16% Cremophor, 31% glycerol monoleate, 10% propylene glycol and diluted with 6 mL of water). Dexamethasone (dosed at 0.5 mg/kg po, similarly formulated) was used as the positive control in the experiment. The data is summarized in FIG. 2. Statistical analysis was conducted using one-way ANOVA, *$p<0.05$.

Example 5

Figure 3:
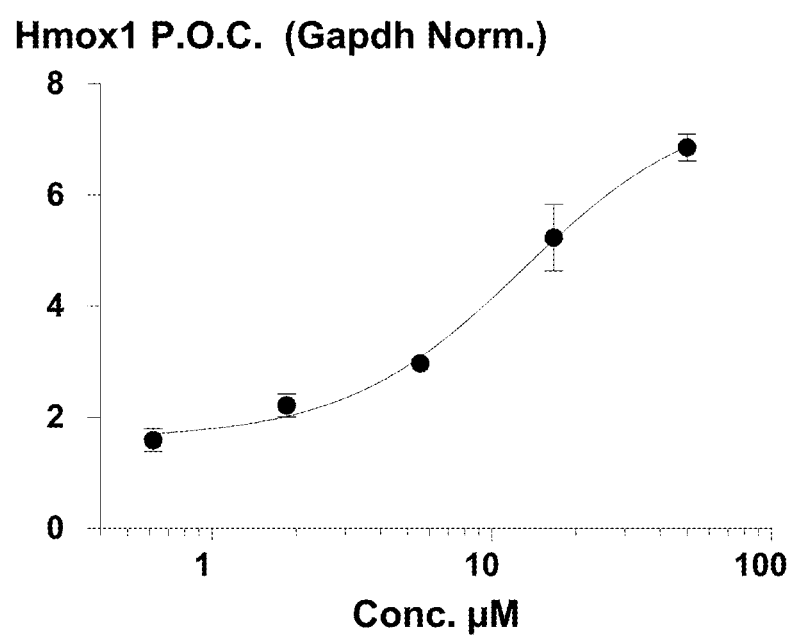
FIG. 3 is a graphical representation of Hmox1 target gene expression in RAW264.7 macrophages that were treated with compound I-1.
Figure 4:
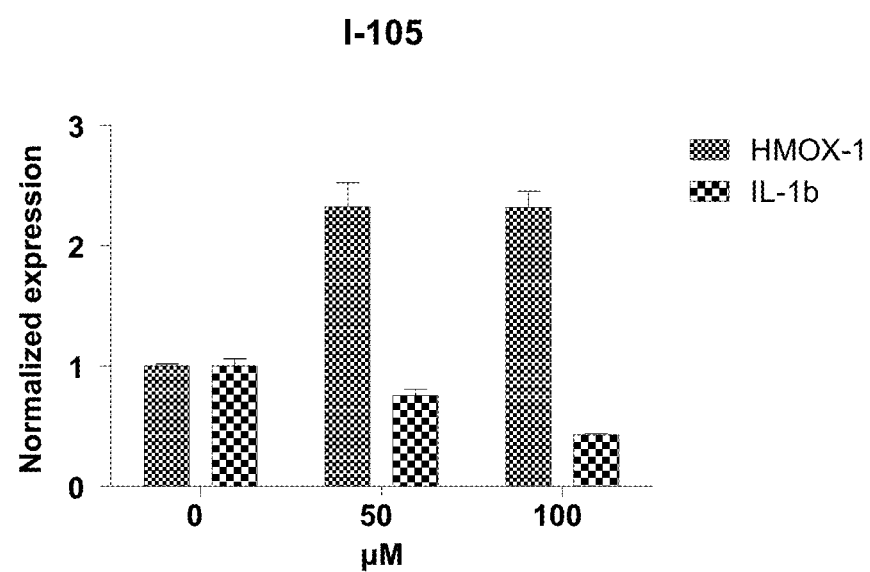
FIG. 4 is a graphical representation of IL-1β and Hmox1 target gene expression in RAW264.7 macrophages that were treated with either control or two different concentrations of compound I-105 (50 μM and 100 μM).

Effect of Fatty Acid Fumarate Derivatives on the Target Gene Hmox1 in RAW Macrophages RAW264.7 macrophages are seeded at a density of 100,000 cells/well in a 96-well plate in DMEM supplemented with 10% FBS and Penn/strep. 16 hours later, medium is aspirated and replaced with 90 µL/well of serum-free DMEM. A fatty acid fumarate conjugate, DHA and EPA are brought up in 100% EtOH to a concentration of 100 mM and then diluted 1:100 in 100% FBS for a 20× stock solution consisting of 1 mM compound and 1% EtOH. The fatty acid fumarate conjugate 20× stock solutions are diluted 1:2 in FBS supplemented with 1% EtOH for a 500 uM 10× stock solution, whereas equal volumes of the DHA and EPA 20× stock solutions are mixed to create a 10× stock solution containing 500 µM each of DHA and EPA. The 10× stock solutions are then serially diluted 1:2 in FBS supplemented with 1% EtOH and 10 µL of each dilution is added to the RAW246.7 cells to generate final concentrations of 50, 25, 12.5, 6.25, 3.12 and 1.6 µM. The compounds are allowed to pre-incubate for 2 hours before stimulation of 100 ng/ml LPS (10 µL of 1 µg/ml LPS is added to each well). Following 3 hours of LPS stimulation, cells are washed once in 1×PBS, aspirated dry, and flash frozen in liquid nitrogen. RNA is then isolated and converted to cDNA using the Cells to cDNA kit (Ambion) according to the manufacturer's protocol. Transcript levels are then measured using ABI Taqman primer/probe assay kits, normalized to GAPDH using the deltaCt method, and the data expressed relative to vehicle only control. FIG. 3 shown below summarizes the positive effect of compound I-1 on the target gene Hmox1. FIG. 4 summarizes the positive effect of the lipoic acid fumarate derivative I-105 on the target gene Hmox1 and IL-1β (protocols for obtaining IL-1β gene expression were detailed in example 1).

Example 6

Effect of Fatty Acid Fumarate Conjugates in the Streptozotocin-Diabetic Rat

Female Sprague-Dawley rats (8 weeks old, with an average weight of 150 g) are used for the study. Diabetes is induced by a single tail vein injection of streptozotocin (STZ) in 0.1 mol/L sodium citrate buffer, pH 4.5. Diabetes is then confirmed by measuring blood glucose levels at two and three days after the STZ treatment. Diabetic animals are classified as those with plasma glucose higher than 16 nmol/L. The diabetic animals are then divided into the vehicle control group and the treatment group (each group having 12 animals). All animals are housed individually with a light dark cycle of 12 hours each, with animals having free access to food and water. In order to maintain body weight and to limit hyperglycemia, diabetic animals are treated with 3 IU of ultralente insulin three times per week in the afternoon (at approximately 3 to 4 pm). In order to maintain glycemic control as the animals gain weight, the dose of insulin is increased to 5 IU at week 15. Animals are dosed with the vehicle or the fatty acid fumarate conjugate over a 28 week period (Examples of vehicles that can be used include combinations of solvents such as polyethylene glycol and propyleneglycol, lipids such as glycerol monooleate and soybean oil, and surfactants such as polysorbate 80 and cremophor EL). Progression of renal disease can be assessed by monthly measurements of urinary albumin and plasma creatinine concentrations. For urinary measurements, rats are housed in metabolic rat cages for 24 hrs. Urinary albumin can be quantified by a competitive ELISA assay according to the protocols outlined in Degenhardt et al, *Kidney International* 2002, 61, p. 939-950. Plasma creatinine concentrations can be measured by the Jaffé picric acid procedure, using the standard kit from Sigma (Sigma cat #555-A). Statistical analyses can be performed using SigmaStat for Windows V1.00. P values can be calculated by non-parametric Mann-Whitney Rank Sum analysis. On week 28, dyslipidemia can also be assessed by measuring plasma triglycerides and total cholesterol. These plasma lipids can be measured by enzymatic, colorimetric, end-point assays using standardized, commercially available kits. Total cholesterol can be analyzed using the Sigma kit (cat #352) and triglycerides can be analyzed by the Sigma kit (cat #37, GOP Grinder).

Example 7

Effect of Fatty Acid Fumarate Conjugates in the Cisplatin-Induced Nephrotoxicity Mouse Model For this study, 10 to 12-week old male C57BL/6 mice of approximately 30 g in body weight are used. After the normal acclimation period, the animals are maintained on a standard diet and water is freely available. Mice are then given a single intraperitoneal injection of either the vehicle or cisplatin (20 mg/kg, at a concentration of 1 mg/mL in saline). Ten animals are used per treatment group. For the drug treatment group, beginning 24 hours prior to the cisplatin injection, animals are dosed with a fatty acid fumarate conjugate (formulated in combinations of solvents such as polyethylene glycol and propyleneglycol, lipids such as glycerol monooleate and soybean oil, and surfactants such as polysorbate 80 and cremophor EL). Dosing is then continued over a period of 72 hours. At this point, animals are sacrificed and blood and kidney tissues are collected. Blood urea nitrogen (BUN) and creatinine are measured. Levels of TNF-α in serum can be determined using a commercially available enzyme-linked immunosorbent assay (ELISA). Tissues are processed for histology and RNA isolation. Tubular injury can be assessed in PAS-stained sections using a semi-quantitative scale described in "G. Ramesh and W. B. Reeves, *Kidney International*, 2004, 65, p. 490-498".

Example 8

Chronic Experimental Autoimmune Encephalomyelitis (EAE) Mouse Model for Multiple Sclerosis (MS)

C57BL/6 female mice that are 8-12 weeks old with body weight in the range of 20-30 g are used for the EAE model. For the induction of EAE, mice receive s.c. injection in the flanks and tail base with 50 µg of MOG35-55 immunopeptide (commercially available from Hooke laboratories, Lawrence, Mass.) in PBS emulsified in an equal volume of complete Freund's adjuvant (CFA) containing *Mycobacterium tuberculosis* H37RA at a final concentration of 0.5 0.5 mg/mL.

Two injections of pertussis toxin (200 ng per mouse i.p.) are given on days 0 and 2. The medication is administered in the indicated vehicle by oral gavage starting from day 3 post immunization until the termination of the study. Each treatment group consists of 8 animals; vehicle alone as a negative control or the Fatty Acid Fumarate Derivative. Animals are weighed and scored for clinical signs of disease on a daily basis over the course of the study (28 days). Disease severity can be assessed using a scale ranging from 0 to 10; with scores as follows: 0=normal; 1=reduced tone of tail; 2=limp tail, impaired righting; 3=absent righting; 4=gait ataxia; 5=mild paraparesis or paraplegia; 8=tetraparesis; 9=moribund; 10=death. Mice are usually sacrificed with scores 7 or higher.

The following non-limiting compound examples serve to illustrate further embodiments of the Fatty Acid Fumarate Derivatives. It is to be understood that any embodiments listed in the Examples section are embodiments of the Fatty Acid Fumarate Derivatives and, as such, are suitable for use in the methods and compositions described above.

Example 9

Preparation of (E)-methyl 4-(2-(4Z,7Z,10Z,13Z,16Z, 19Z)-docosa-4,7,10,13,16,19-hexaenamidoethylamino)-4-oxobut-2-enoate (Compound I-1)

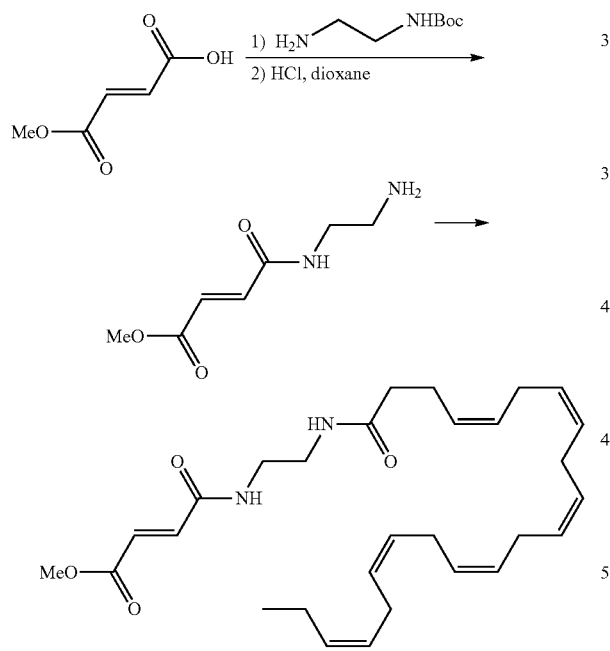

Mono methyl fumarate (1.7 g, 13.1 mmol) was taken up in 20 mL of $CH_2Cl_2$ along with oxalyl chloride (1.1 mL, 13.1 mmol). After a few drops of DMF were added, the reaction mixture was stirred at room temperature until all the solids had dissolved and all gas evolution had ceased (1 h). This freshly prepared solution of the acid chloride was added dropwise at 0° C. to a solution containing tert-butyl 2-aminoethylcarbamate (2.1 g, 13.1 mmol) and $Et_3N$ (2.8 mL, 19.6 mmol) in 200 mL of $CH_2Cl_2$. The resulting reaction mixture was warmed to room temperature and stirred for 2 h. It was then washed with brine, dried ($Na_2SO_4$) and concentrated under reduced pressure. Purification by chromatography ($CH_2Cl_2$) afforded 2.2 g of (E)-methyl 4-(2-(tert-butoxycarbonyl)ethylamino)-4-oxobut-2-enoate (62% yield). (E)-Methyl 4-(2-(tert-butoxycarbonyl)ethylamino)-4-oxobut-2-enoate (2.2 g, 8.1 mmol) was taken up in 10 mL of 4 M HCl in dioxane. The resulting reaction mixture was allowed to stand at room temperature for 1 h, then diluted with 50 mL of EtOAc and concentrated under reduced pressure to afford the HCl salt of (E)-methyl 4-(2-aminoethylamino)-4-oxobut-2-enoate.

The HCl salt of (E)-methyl 4-(2-aminoethylamino)-4-oxobut-2-enoate (8.1 mmol) was taken up in 40 mL of $CH_3CN$ along with (4Z,7Z,10Z,13Z,16Z,19Z)-docosa-4,7,10,13,16, 19-hexaenoic acid (DHA, 2.66 g, 8.1 mmol), HATU (3.4 g, 12.1 mmol) and DIEA (4.2 mL). The resulting reaction mixture was stirred at room temperature for 2 h and diluted with EtOAc. The organic layer was washed with saturated aqueous $NaHCO_3$, brine, dried ($Na_2SO_4$) and concentrated under reduced pressure. Purification by chromatography (95% $CH_2Cl_2$, 5% MeOH) afforded 1.4 g of (E)-methyl 4-(2-(4Z, 7Z,10Z,13Z,16Z,19Z)-docosa-4,7,10,13,16,19-hexaenamidoethylamino)-4-oxobut-2-enoate. MS (EI) calcd for $C_{29}H_{42}N_2O_4$: 482.31. found 483 (M+1).

Example 10

Preparation of (E)-4-(2-(4Z,7Z,10Z,13Z,16Z,19Z)-docosa-4,7,10,13,16,19-hexaenamidoethylamino)-4-oxobut-2-enoic acid (Compound I-102)

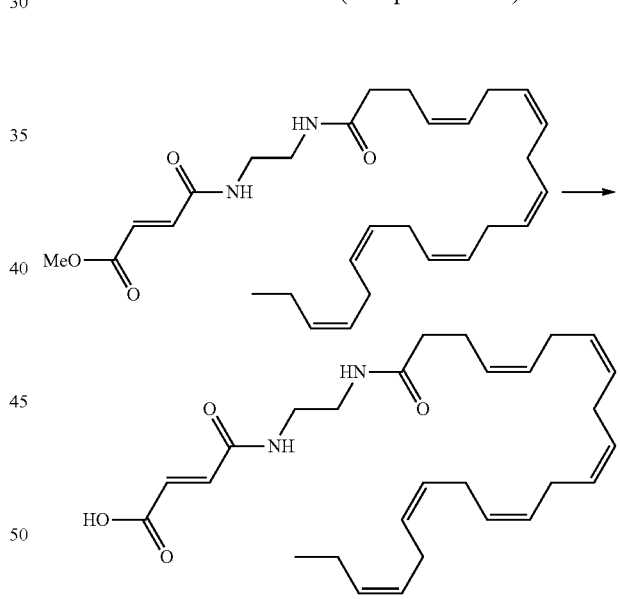

(E)-Methyl 4-(2-(4Z,7Z,10Z,13Z,16Z,19Z)-docosa-4,7, 10,13,16,19-hexaenamidoethylamino)-4-oxobut-2-enoate (200 mg, 0.41 mmol) was taken up in 5 mL of THF along with 2 mL of a 5 N NaOH. The resulting reaction mixture was stirred at room temperature for 1 h, concentrated under reduced pressure to remove the THF, and diluted with water (10 mL). The aqueous layer was acidified to pH=2 with 3 N HCl and then extracted with EtOAc. The combined organic layers were washed with brine, dried ($Na_2SO_4$) and concentrated under reduced pressure to afford 190 mg of (E)-4-(2-(4Z,7Z,10Z,13Z,16Z,19Z)-docosa-4,7,10,13,16,19-hexaenamidoethylamino)-4-oxobut-2-enoic acid (97% yield). MS (EI) calcd for $C_{28}H_{40}N_2O_4$: 468.30. found 469 (M+1).

Example 11

Preparation of (E)-methyl 4-(1-(4Z,7Z,10Z,13Z,16Z, 19Z)-docosa-4,7,10,13,16,19-hexaenamido-2-methylpropan-2-ylamino)-4-oxobut-2-enoate (Compound I-22)

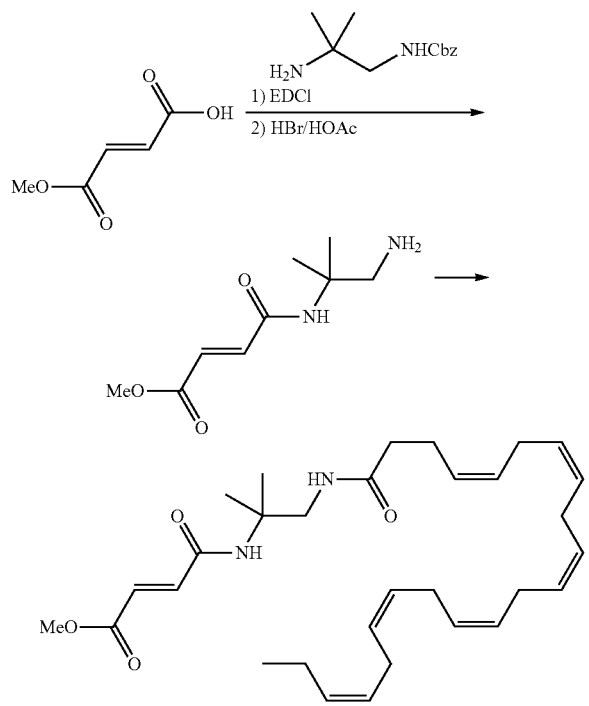

2-Methylpropane-1,2-diamine (1.52 g, 14.5 mmol) was dissolved in 50 mL of CH$_2$Cl$_2$ and cooled to 0° C. Benzyl chloroformate (2.0 mL, 14.5 mmol) was then added dropwise at 0° C. over a period of 10 min. The resulting reaction mixture was warmed to room temperature, stirred for 4 h and then concentrated under reduced pressure to afford benzyl 2-amino-2-methylpropylcarbamate as the HCl salt.

Mono methyl fumarate (455 mg, 3.5 mmol) was taken up in 10 mL of CH$_3$CN along with the HCl salt of benzyl 2-amino-2-methylpropylcarbamate (3.5 mmol), DIEA (0.50 mL) and EDCI (1.2 g). The resulting reaction mixture was stirred at room temperature for 6 h and diluted with EtOAc. The organic layer was washed with saturated aqueous NaHCO$_3$, brine, dried (Na$_2$SO$_4$) and concentrated under reduced pressure. Purification by chromatography (95% CH$_2$Cl$_2$, 5% MeOH) afforded 400 mg of 3-(2-tert-butoxycarbonylamino-1,1-dimethyl-ethylcarbamoyl)-acrylic acid methyl ester (34% yield).

3-(2-tert-Butoxycarbonylamino-1,1-dimethyl-ethylcarbamoyl)-acrylic acid methyl ester (400 mg, 1.2 mmol) was taken up in 3 mL of 33% HBr in glacial acetic acid and allowed to stand at room temperature for 1 h. The resulting reaction mixture was concentrated under reduced pressure to afford the HBr salt of 3-(2-amino-1,1-dimethyl-ethylcarbamoyl)-acrylic acid methyl ester. This material was taken up in 5 mL of CH$_3$CN along with (4Z,7Z,10Z,13Z,16Z,19Z)-docosa-4,7,10,13,16,19-hexaenoic acid (DHA, 393 mg, 1.2 mmol), HATU (547 mmol, 1.3 mmol) and DIEA (0.63 mL). The resulting reaction mixture was stirred at room temperature for 2 h and diluted with EtOAc. The organic layer was washed with saturated aqueous NaHCO$_3$, brine, dried (Na$_2$SO$_4$) and concentrated under reduced pressure. Purification by chromatography (95% CH$_2$Cl$_2$, 5% MeOH) afforded 200 mg of (E)-methyl 4-(1-(4Z,7Z,10Z,13Z,16Z,19Z)-docosa-4,7,10,13,16,19-hexaenamido-2-methylpropan-2-ylamino)-4-oxobut-2-enoate (33% yield). MS (EI) calcd for C$_{31}$H$_{46}$N$_2$O$_4$: 510.35. found 511 (M+1).

Example 12

Preparation of (E)-methyl 4-(2-(2-(2-(4Z,7Z,10Z, 13Z,16Z,19Z)-docosa-4,7,10,13,16,19-hexaenamidoethyl)disulfanyl)ethylamino)-4-oxobut-2-enoate (Compound I-5)

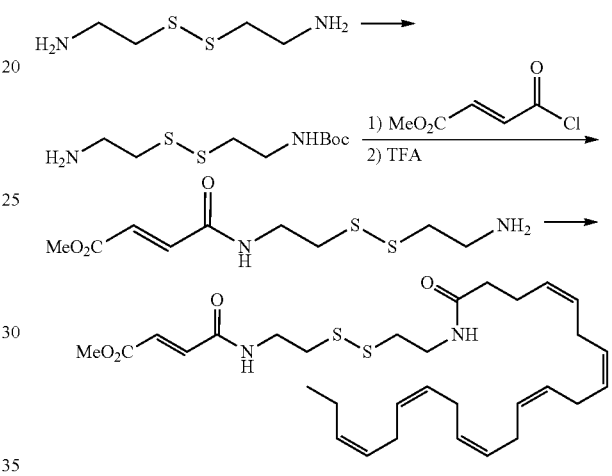

Cystamine dihydrochloride (1.0 g, 4.44 mmol) was dissolved in 50 mL of MeOH. Triethylamine (1.85 mL, 3 eq) was added at room temperature, followed by dropwise addition of Boc$_2$O (0.97 g, 4.44 mmol) as a solution in 5 mL of MeOH The resulting reaction mixture was stirred at room temperature for 3 h. It was then concentrated under reduced pressure and the resulting residue was taken up in 20 mL of 1M NaH$_2$PO$_4$. The aqueous layer was washed with 10 mL of a 1:1 solution of pentane/EtOAc, basified to pH 9 with 1M NaOH, and extracted with EtOAc. The combined organic layers were washed with brine, dried (Na$_2$SO$_4$) and concentrated under reduced pressure to afford 500 mg of tert-butyl 2-(2-(2-aminoethyl)disulfanyl)ethylcarbamate (44% yield).

Separately, mono methyl fumarate (263 mg, 2.02 mmol) was taken up in 10 mL of CH$_2$Cl$_2$ along with oxalyl chloride (170 μL, 2.02 mmol). After a few drops of DMF were added, the reaction mixture was stirred at room temperature until all the solids had dissolved and all gas evolution had ceased (1 h). This freshly prepared solution of the acid chloride was added dropwise at 0° C. to a solution containing tert-butyl 2-(2-(2-aminoethyl)disulfanyl)ethylcarbamate (500 mg) and Et$_3$N (420 μL, 3 mmol) in 20 mL of CH$_2$Cl$_2$. The resulting reaction mixture was warmed to room temperature and stirred for 2 h. It was then washed with brine, dried (Na$_2$SO$_4$) and concentrated under reduced pressure. Purification by chromatography (CH$_2$Cl$_2$) afforded 450 mg of (E)-methyl 4-(2-(2-(2-(tert-butoxycarbonyl)ethyl)disulfanyl)ethylamino)-4-oxobut-2-enoate. This material was taken up in 5 mL of a 25% TFA in CH$_2$Cl$_2$ solution and allowed to stand at room temperature for 4 h. The reaction mixture was then concentrated under reduced pressure to afford the TFA salt of (E)-methyl 4-(2-(2-(2-aminoethyl)disulfanyl)ethylamino)-4-oxobut-2-enoate. This material was taken up in 10 mL of CH$_3$CN along with (4Z,7Z,10Z,13Z,16Z,19Z)-docosa-4,7,10,13,16,19-hexaenoic acid (DHA, 403 mg, 1.23 mmol), HATU (517 mg, 1.35 mmol) and DIEA (0.640 mL). The resulting reaction mixture was stirred at room temperature for 2 h. It was then diluted with EtOAc and washed successively with saturated aqueous NaHCO$_3$ and brine. The organic layer was dried (Na$_2$SO$_4$) and concentrated under reduced pressure. Purification by chromatography (95% CH$_2$Cl$_2$, 5% MeOH) afforded 200 mg of (E)-methyl 4-(2-(2-(2-(4Z,7Z,10Z,13Z,16Z,19Z)-docosa-4,7,10,13,16,19-hexaenamidoethyl)disulfanyl)ethylamino)-4-oxobut-2-enoate. MS (EI) calcd for C$_{31}$H$_{46}$N$_2$O$_4$S$_2$: 574.29. found: 575 (M+1).

Example 13

Preparation of (E)-methyl 4-(2-(2-(4Z,7Z,10Z,13Z,16Z,19Z)-docosa-4,7,10,13,16,19-hexaenamidoethoxy)ethylamino)-4-oxobut-2-enoate (Compound I-3)

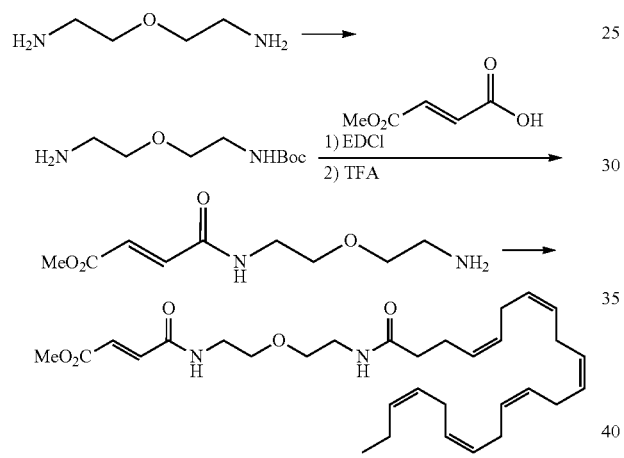

Sodium hydroxide (400 mg, 10 mmol) was dissolved in 70 mL of MeOH and 2-(2-aminoethoxy)ethanamine dihydrochloride (1.0 g, 5.65 mmol) was added. The resulting reaction mixture was stirred at room temperature for 30 min. A solution containing Boc$_2$O (740 mg, 3.40 mmol) in 15 mL of THF was then added dropwise, at room temperature, over a period of 15 min. The resulting reaction mixture was stirred at room temperature for 18 h, then concentrated under reduced pressure. The resulting residue was taken up in 200 mL of CH$_2$Cl$_2$ and stirred vigorously at room temperature for 4 h. The mixture was filtered and the filtrate was concentrated under reduced pressure to afford 850 mg of tert-butyl 2-(2-aminoethoxy)ethylcarbamate (74% yield).

tert-Butyl 2-(2-aminoethoxy)ethylcarbamate (1.0 g, 4.90 mmol) was then taken up in 20 mL of CH$_3$CN along with mono methyl fumarate (637 mg, 4.90 mmol) and EDCI (1.7 g. 5.39 mmol). The resulting reaction mixture was stirred at room temperature for 18 h. It was then diluted with EtOAc (20 mL), washed with saturated aqueous NaHCO$_3$, brine, dried (Na$_2$SO$_4$) and concentrated under reduced pressure. The resulting residue was purified by chromatography (9:1 CH$_2$Cl$_2$/MeOH) to afford 1.0 g of (E)-methyl 4-(2-(2-(tert-butoxycarbonyl)ethoxy)ethylamino)-4-oxobut-2-enoate (64% yield). MS (EI) calcd for C$_{14}$H$_{24}$N$_2$O$_6$: 316.16. found: 317 (M+1).

(E)-methyl 4-(2-(2-(tert-butoxycarbonyl)ethoxy)ethylamino)-4-oxobut-2-enoate (1.0 g, 3.16 mmol) was taken up in 10 mL of 25% TFA in CH$_2$Cl$_2$. The reaction mixture was allowed to stand at room temperature for 2 h and then concentrated under reduced pressure to afford (E)-methyl 4-(2-(2-aminoethoxy)ethylamino)-4-oxobut-2-enoate as the TFA salt. This material was then taken up in 10 mL of CH$_3$CN along with (4Z,7Z,10Z,13Z,16Z,19Z)-docosa-4,7,10,13,16,19-hexaenoic acid (DHA, 1.0 g, 3.16 mmol), HATU (1.30 g, 3.5 mmol) and DIEA (1.6 mL). The resulting reaction mixture was stirred at room temperature for 2 h, then diluted with EtOAc and washed successively with saturated aqueous NaHCO$_3$ and brine.

The organic layer was dried (Na$_2$SO$_4$) and concentrated under reduced pressure. Purification by chromatography (60% EtOAc, 40% pentane) afforded 220 mg of (E)-methyl 4-(2-(2-(4Z,7Z,10Z,13Z,16Z,19Z)-docosa-4,7,10,13,16,19-hexaenamidoethoxy)ethylamino)-4-oxobut-2-enoate (13% yield). MS (EI) calcd for C$_{31}$H$_{46}$N$_2$O$_5$: 526.34. found: 527 (M+1).

Example 14

Preparation of (E)-methyl 4-(4-(4Z,7Z,10Z,13Z,16Z,19Z)-docosa-4,7,10,13,16,19-hexaenoylpiperazin-1-yl)-4-oxobut-2-enoate (Compound I-40)

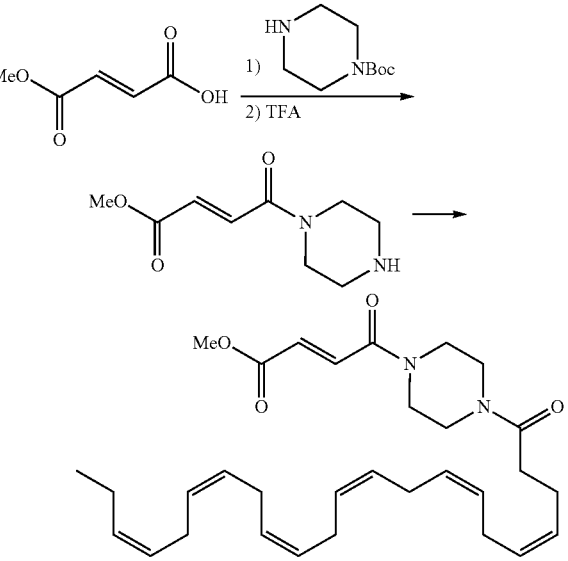

Mono methyl fumarate (650 mg, 5.0 mmol) was taken up in 10 mL of CH$_2$Cl$_2$ and oxalyl chloride (420 µL, 5.0 mmol) was added. After a few drops of DMF was added, the reaction mixture was stirred at room temperature until all gas evolution had ceased (1 h). This freshly prepared solution of acid chloride was then added dropwise at 0° C. to a solution containing Boc-piperazine (930 mg) and triethylamine (1.0 mL, 7.5 mmol) in 20 mL of CH$_2$Cl$_2$. The resulting reaction mixture was stirred at room temperature for 1 h and washed with brine. The organic layer was dried (Na$_2$SO$_4$) and concentrated under reduced pressure. Purification by chromatography (CH$_2$Cl$_2$) afforded 310 mg of (E)-tert-butyl 4-(4-methoxy-4-oxobut-2-enoyl)piperazine-1-carboxylate (21% yield).

(E)-tert-Butyl 4-(4-methoxy-4-oxobut-2-enoyl)piperazine-1-carboxylate (310 mg, 1.04 mmol) was taken up in 5 mL of 25% TFA in $CH_2Cl_2$ and allowed to stand at room temperature for 2 h. The reaction mixture was concentrated under reduced pressure to afford the TFA salt of (E)-methyl 4-oxo-4-(piperazin-1-yl)but-2-enoate. This material was taken up in 10 mL of $CH_3CN$ along with (4Z,7Z,10Z,13Z,16Z,19Z)-docosa-4,7,10,13,16,19-hexaenoic acid (DHA, 375 mg, 1.04 mmol), HATU (435 mg, 1.14 mmol) and DIEA (540 μL). The resulting reaction mixture was stirred at room temperature for 2 h. It was then diluted with EtOAc and washed successively with saturated aqueous $NaHCO_3$ and brine. The organic layer was dried ($Na_2SO_4$) and concentrated under reduced pressure. Purification by chromatography ($CH_2Cl_2$) afforded 80 mg of (E)-methyl 4-(4-(4Z,7Z,10Z,13Z,16Z,19Z)-docosa-4,7,10,13,16,19-hexaenoylpiperazin-1-yl)-4-oxobut-2-enoate (15% yield). MS (EI) calcd for $C_{31}H_{44}N_2O_4$: 508.33. found: 509 (M+1).

Example 15

Preparation of 2-(4Z,7Z,10Z,13Z,16Z,19Z)-docosa-4,7,10,13,16,19-hexaenamidoethyl methyl fumarate (Compound I-103)

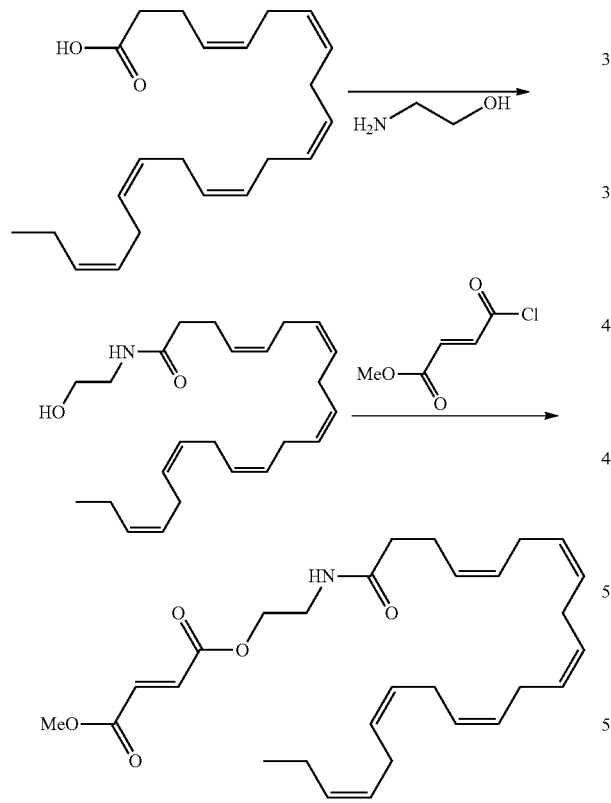

(4Z,7Z,10Z,13Z,16Z,19Z)-Docosa-4,7,10,13,16,19-hexaenoic acid (DHA, 1.2 g, 3.66 mmol) was taken up in 20 mL of $CH_3CN$ along with ethanolamine (220 μL, 3.66 mmol), HATU (1.5 g, 4.0 mmol) and DIEA (950 μL, 5.49 mmol). The resulting reaction mixture was stirred at room temperature for 2 h and then diluted with EtOAc. The organic layer was washed with saturated aqueous $NaHCO_3$, brine, dried ($Na_2SO_4$) and concentrated under reduced pressure to afford crude (4Z,7Z,10Z,13Z,16Z,19Z)—N-(2-hydroxyethyl) docosa-4,7,10,13,16,19-hexaenamide. This material was taken up in 15 mL of $CH_2Cl_2$ along with (E)-methyl 4-chloro-4-oxobut-2-enoate (3.66 mmol) and triethylamine (765 μL, 5.49 mmol). The resulting reaction mixture was stirred at room temperature for 18 h. It was then diluted with $CH_2Cl_2$ and washed with brine. The organic layer was dried ($Na_2SO_4$) and concentrated under reduced pressure. Purification by chromatography (60% EtOAc, 40% pentane) afforded 380 mg of 2-(4Z,7Z,10Z,13Z,16Z,19Z)-docosa-4,7,10,13,16,19-hexaenamidoethyl methyl fumarate (21% yield). MS (EI) calcd for $C_{29}H_{41}NO_5$: 483.3. found: 484 (M+1).

Example 16

Preparation of (E)-methyl 4-((R)-3-(1-(2-(4Z,7Z,10Z,13Z,16Z,19Z)-docosa-4,7,10,13,16,19-hexaenamidoethyl)-2,5-dioxopyrrolidin-3-ylthio)-1-methoxy-1-oxopropan-2-ylamino)-4-oxobut-2-enoate (Compound I-39)

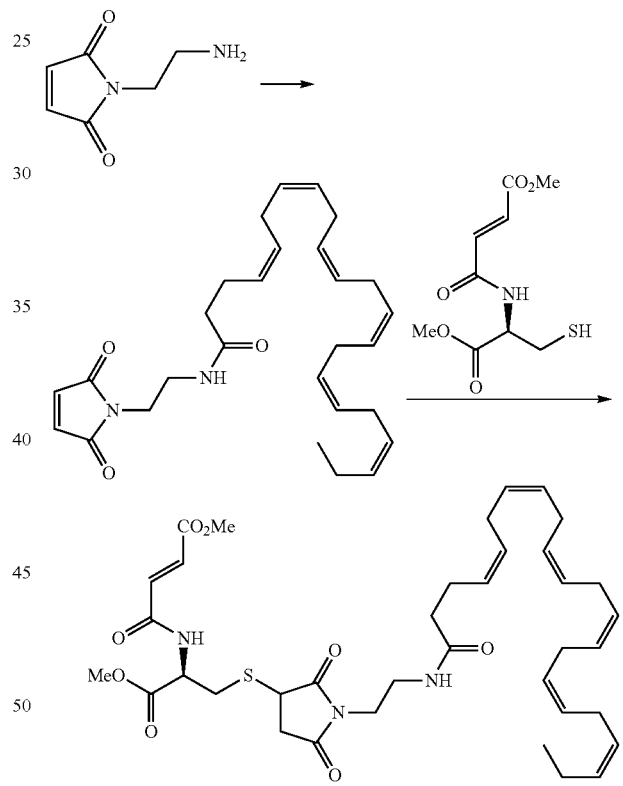

The TFA salt of 1-(2-aminoethyl)-1H-pyrrole-2,5-dione (Aldrich, 280 mg, 1.10 mmol) was taken up in 10 mL of $CH_3CN$ along with (4Z,7Z,10Z,13Z,16Z,19Z)-docosa-4,7,10,13,16,19-hexaenoic acid (DHA, 360 mg, 1.1 mmol), HATU (460 mg, 1.2 mmol) and DIEA (0.58 mL). The resulting reaction mixture was stirred at room temperature for 3 h. It was then diluted with EtOAc and washed successively with saturated aqueous $NaHCO_3$ and brine. The organic layer was dried ($Na_2SO_4$) and concentrated under reduced pressure. Purification by chromatography ($CH_2Cl_2$) afforded 350 mg of (4Z,7Z,10Z,13Z,16Z,19Z)—N-(2-(2,5-dioxo-2H-pyrrol-1(5H)-yl)ethyl)docosa-4,7,10,13,16,19-hexaenamide (70% yield).

Separately, mono methyl fumarate (100 mg, 0.77 mmol) was taken up in 4 mL of $CH_3CN$ along with L-cysteine methyl ester hydrochloride (132 mg, 0.77 mmol), EDCI (245 mg, 0.77 mmol) and N-methylmorpholine (85 μL, 0.77 mmol). The reaction mixture was stirred at room temperature for 3 h. It was then diluted with EtOAc. The organic layer was washed with saturated aqueous $NaHCO_3$ and brine. The organic layer was dried ($Na_2SO_4$) and concentrated under reduced pressure to afford crude (R,E)-methyl 4-(3-mercapto-1-methoxy-1-oxopropan-2-ylamino)-4-oxobut-2-enoate. This material was then taken up in 3 mL of $CH_3CN$ along with (4Z,7Z,10Z,13Z,16Z,19Z)—N-(2-(2,5-dioxo-2H-pyrrol-1(5H)-yl)ethyl)docosa-4,7,10,13,16,19-hexaenamide (173 mg, 0.38 mmol) and stirred at room temperature for 30 min. The reaction mixture was then concentrated under reduced pressure. Purification by chromatography ($CH_2Cl_2$) afforded 60 mg of (E)-methyl 4-((R)-3-(1-(2-(4Z,7Z,10Z,13Z,16Z,19Z)-docosa-4,7,10,13,16,19-hexaenamidoethyl)-2,5-dioxopyrrolidin-3-ylthio)-1-methoxy-1-oxopropan-2-ylamino)-4-oxobut-2-enoate (22%). MS (EI) calcd for $C_{37}H_{51}N_3O_8S$: 697.34. found: 698 (M+1).

Example 17

Preparation of (E)-methyl 4-(2-((2-(4Z,7Z,10Z,13Z,16Z,19Z)-docosa-4,7,10,13,16,19-hexaenamidoethyl)(methyl)amino)ethylamino)-4-oxobut-2-enoate (Compound I-4)

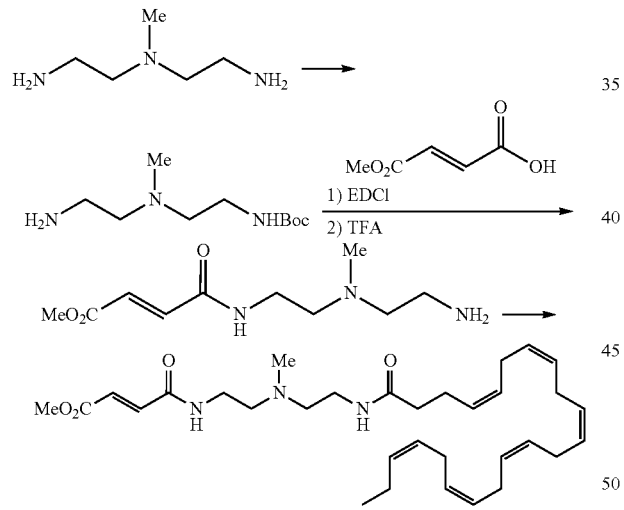

N1-(2-Aminoethyl)-N1-methylethane-1,2-diamine (5.0 g, 42.7 mmol) was dissolved in 100 mL of $CH_2Cl_2$ and cooled to 0° C. A solution of di-tert-butylcarbonate (0.93 g, 4.27 mmol) in $CH_2Cl_2$ (10 mL) was then added dropwise at 0° C. over a period of 15 min. The resulting reaction mixture was stirred at 0° C. for 30 min and then warmed to room temperature. After stirring at room temperature for 2 h, the reaction mixture was diluted with $CH_2Cl_2$ (100 mL). The organic layer was washed with brine (3×25 mL), dried ($Na_2SO_4$) and concentrated under reduced pressure to afford 1.1 g of tert-butyl 2-((2-aminoethyl)(methyl)amino)ethylcarbamate.

tert-Butyl 2-((2-aminoethyl)(methyl)amino)ethylcarbamate (500 mg, 2.3 mmol) was taken up in 10 mL of $CH_3CN$ along with salicylic acid (310 mg, 2.3 mmol) and EDCI (485 mg, 2.53 mmol). The resulting reaction mixture was stirred at room temperature for 18 h and then diluted with EtOAc. The organic layer was washed with saturated aqueous $NaHCO_3$, brine, dried ($Na_2SO_4$) and concentrated under reduced pressure. The resulting residue was purified by chromatography (95% $CH_2Cl_2$, 5% MeOH) to afford 380 mg of tert-butyl 2-((2-(2-hydroxybenzamido)ethyl)(methyl)amino)ethylcarbamate (49% yield). MS (EI) calcd for $C_{17}H_{27}N_3O_4$: 337.2. found: 338 (M+1).

tert-Butyl 2-((2-(2-hydroxybenzamido)ethyl)(methyl)amino)ethylcarbamate (380 mg, 1.13 mmol) was taken up in 5 mL of a 25% TFA in $CH_2Cl_2$ and allowed to stand at room temperature for 3 h. The reaction mixture was concentrated under reduced pressure to afford the TFA salt of N-(2-((2-aminoethyl)(methyl)amino)ethyl)-2-hydroxybenzamide. This material was taken up in 10 mL of $CH_3CN$ along with (4Z,7Z,10Z,13Z,16Z,19Z)-docosa-4,7,10,13,16,19-hexaenoic acid (DHA, 370 mg, 1.13 mmol), HATU (472 mg, 1.24 mmol) and DIEA (0.59 mL). The resulting reaction mixture was stirred at room temperature for 2 h. It was then diluted with EtOAc and washed successively with saturated aqueous $NaHCO_3$ and brine. The organic layer was dried ($Na_2SO_4$) and concentrated under reduced pressure. Purification by chromatography (95% $CH_2Cl_2$, 5% MeOH) afforded 420 mg of N-(2-((2-(4Z,7Z,10Z,13Z,16Z,19Z)-docosa-4,7,10,13,16,19-hexaenamidoethyl)(methyl)amino)ethyl)-2-hydroxybenzamide. MS (EI) calcd for $C_{34}H_{49}N_3O_3$: 547.38. found: 548 (M+1).

Example 18

Preparation of (E)-methyl 4-(2-(5Z,8Z,11Z,14Z,17Z)-eicosa-5,8,11,14,17-pentaenamidoethylamino)-4-oxobut-2-enoate (Compound I-2)

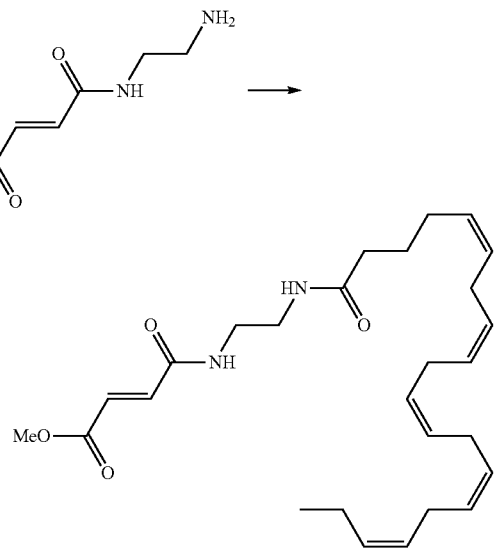

The HCl salt of (E)-methyl 4-(2-aminoethylamino)-4-oxobut-2-enoate (0.735 mmol) was taken up in 40 mL of $CH_3CN$ along with (5Z,8Z,11Z,14Z,17Z)-eicosa-5,8,11,14,17-pentaenoic acid (EPA, 222 mg, 0.735 mmol), HATU (307 mg, 0.81 mmol) and DIEA (380 μL). The resulting reaction mixture was stirred at room temperature for 2 h and diluted with EtOAc. The organic layer was washed with saturated aqueous $NaHCO_3$, brine, dried ($Na_2SO_4$) and concentrated under reduced pressure. Purification by chromatography (95% CH$_2$Cl$_2$, 5% MeOH) afforded 300 mg of (E)-methyl 4-(2-(5Z,8Z,11Z,14Z,17Z)-eicosa-5,8,11,14,17-pentaenamidoethylamino)-4-oxobut-2-enoate (89% yield). MS (EI) calcd for C$_{27}$H$_{40}$N$_2$O$_4$: 456.3. found: 457 (M+1).

Example 19

Preparation of (E)-ethyl 4-(2-(4Z,7Z,10Z,13Z,16Z,19Z)-docosa-4,7,10,13,16,19-hexaenamidoethylamino)-4-oxobut-2-enoate (Compound I-66)

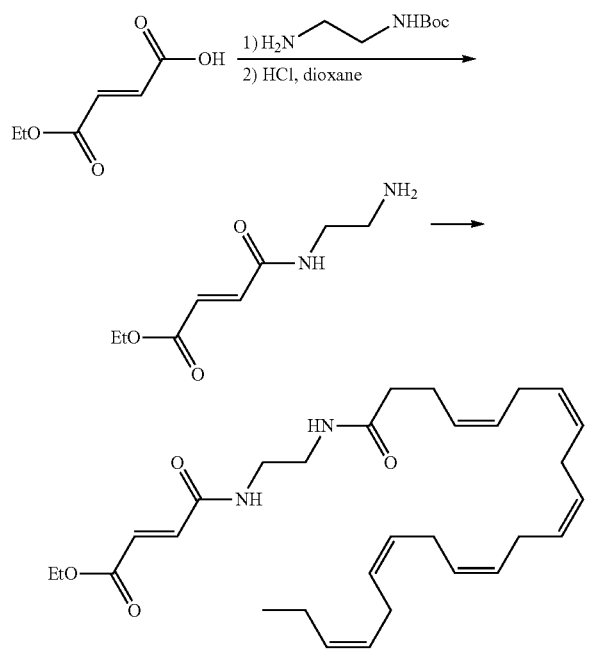

Mono ethyl fumarate (commercially available) was subjected to the same reaction conditions outlined earlier in the preparation of (E)-methyl 4-(2-(4Z,7Z,10Z,13Z,16Z,19Z)-docosa-4,7,10,13,16,19-hexaenamidoethylamino)-4-oxobut-2-enoate. The desired product, namely (E)-ethyl 4-(2-(4Z,7Z,10Z,13Z,16Z,19Z)-docosa-4,7,10,13,16,19-hexaenamidoethylamino)-4-oxobut-2-enoate, was obtained after purification by silica gel chromatography. MS (EI) calcd for C$_{30}$H$_{40}$N$_2$O$_4$: 496.33. found 497 (M+1).

Example 20

Preparation of (E)-methyl 4-(methyl(2-((4Z,7Z,10Z,13Z,16Z,19Z)—N-methyldocosa-4,7,10,13,16,19-hexaenamido)ethyl)amino)-4-oxobut-2-enoate (Compound I-104)

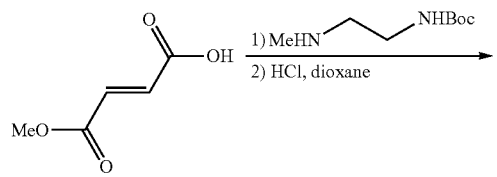

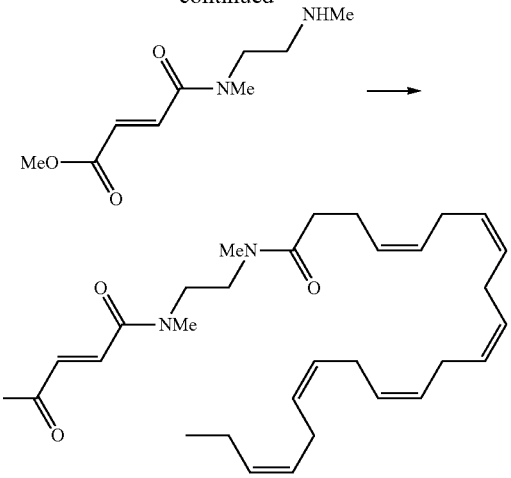

tert-Butyl methyl(2-(methylamino)ethyl)carbamate was prepared as follows: N$^1$,N$^2$-dimethylethane-1,2-diamine (40 mmol) was dissolved in 100 mL of CH$_2$Cl$_2$ and cooled to 0° C. A solution of di-tert-butylcarbonate (4.0 mmol) in CH$_2$Cl$_2$ (10 mL) was then added dropwise at 0° C. over a period of 15 min. The resulting reaction mixture was stirred at 0° C. for 30 min and then warmed to room temperature. After stirring at room temperature for 2 h, the reaction mixture was diluted with CH$_2$Cl$_2$ (100 mL). The organic layer was washed with brine (3×25 mL), dried (Na$_2$SO$_4$) and concentrated under reduced pressure to afford tert-butyl methyl(2-(methylamino)ethyl)carbamate. This amine was subjected to the same reaction conditions outlined earlier in the preparation of (E)-methyl 4-(2-(4Z,7Z,10Z,13Z,16Z,19Z)-docosa-4,7,10,13,16,19-hexaenamidoethylamino)-4-oxobut-2-enoate. The desired product, namely (E)-methyl 4-(methyl(2-((4Z,7Z,10Z,13Z,16Z,19Z)—N-methyldocosa-4,7,10,13,16,19-hexaenamido)ethyl)amino)-4-oxobut-2-enoate, was obtained after purification by silica gel chromatography. MS (EI) calcd for C$_{31}$H$_{46}$N$_2$O$_4$: 510.35. found 511 (M+1).

Example 21

Preparation of (E)-methyl 4-((2R,6S)-4-((4Z,7Z,10Z,13Z,16Z,19Z)-docosa-4,7,10,13,16,19-hexaenoyl)-2,6-dimethylpiperazin-1-yl)-4-oxobut-2-enoate (Compound I-41)

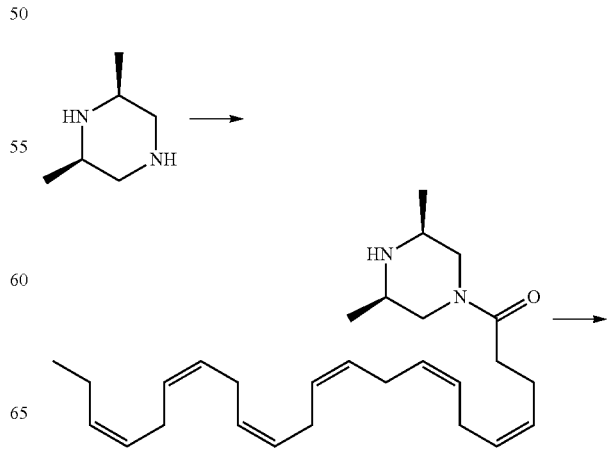

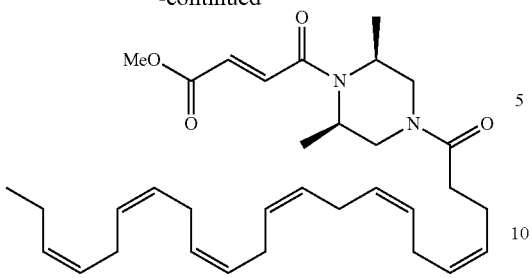

(2R,6S)-2,6-Dimethylpiperazine (173 mg, 1.52 mmol) was taken up in 8 mL of $CH_3CN$ along with DHA (500 mg, 1.52 mmol) and EDC (320 mg). The resulting reaction mixture was stirred at room temperature for 2 h and concentrated under reduced pressure. The resulting residue was taken up in EtOAc, washed with brine, dried ($Na_2SO_4$) and concentrated under reduced pressure to afford (4Z,7Z,10Z,13Z,16Z,19Z)-1-((3R,5S)-3,5-dimethylpiperazin-1-yl)docosa-4,7,10,13, 16,19-hexaen-1-one. This material was taken up in mL of $CH_3CN$ along with mono methyl fumarate (198 mg, 1.52 mmol) and HATU (635 mg, 1.67 mmol). The resulting reaction mixture was stirred at room temperature for 2 h and diluted with EtOAc. The organic layer was washed with brine, dried ($Na_2SO_4$) and concentrated under reduced pressure. Purification by silica gel chromatography (gradient elution, pentane to 80% EtOAc, 20% pentane) afforded 180 mg of (E)-methyl 4-((2R,6S)-4-((4Z,7Z,10Z,13Z,16Z,19Z)-docosa-4,7,10,13,16,19-hexaenoyl)-2,6-dimethylpiperazin-1-yl)-4-oxobut-2-enoate. MS (EI) calcd for $C_{33}H_{48}N_2O_4$: 536.36. found 537 (M+1).

Example 22

Preparation of (R,E)-methyl 4-(2-(5-(1,2-dithiolan-3-yl)pentanamido)ethylamino)-4-oxobut-2-enoate (Compound I-105)

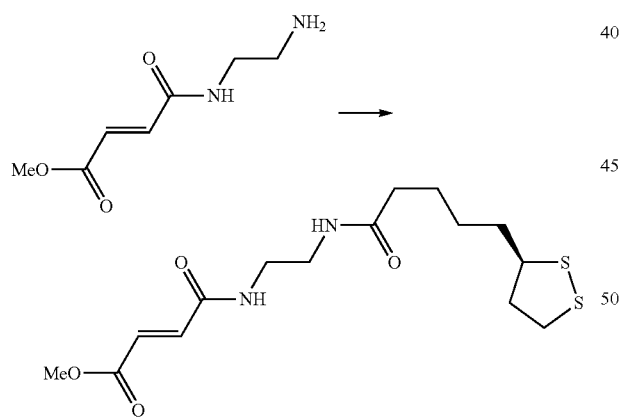

The HCl salt of (E)-methyl 4-(2-aminoethylamino)-4-oxobut-2-enoate (0.515 mmol) was taken up in 10 mL of $CH_3CN$ along with R-lipoic acid (TCI, 106 mg, 0.515 mmol), HATU (215 mg, 0.567 mmol) and DIEA (270 µL, 1.55 mmol). The resulting reaction mixture was stirred at room temperature for 18 h and diluted with EtOAc. The organic layer was washed with brine, dried ($Na_2SO_4$) and concentrated under reduced pressure. Purification by silica gel chromatography (95% $CH_2Cl_2$, 5% MeOH) afforded 120 mg of (R,E)-methyl 4-(2-(5-(1,2-dithiolan-3-yl)pentanamido)ethylamino)-4-oxobut-2-enoate. MS (EI) calcd for $C_{15}H_{24}N_2O_4S$: 360.12. found 361 (M+1).

Example 23

Preparation of (S)-2-((5Z,8Z,11Z,14Z,17Z)-icosa-5,8,11,14,17-pentaenamido)-6-((E)-4-methoxy-4-oxobut-2-enamido)hexanoic acid (I-72)

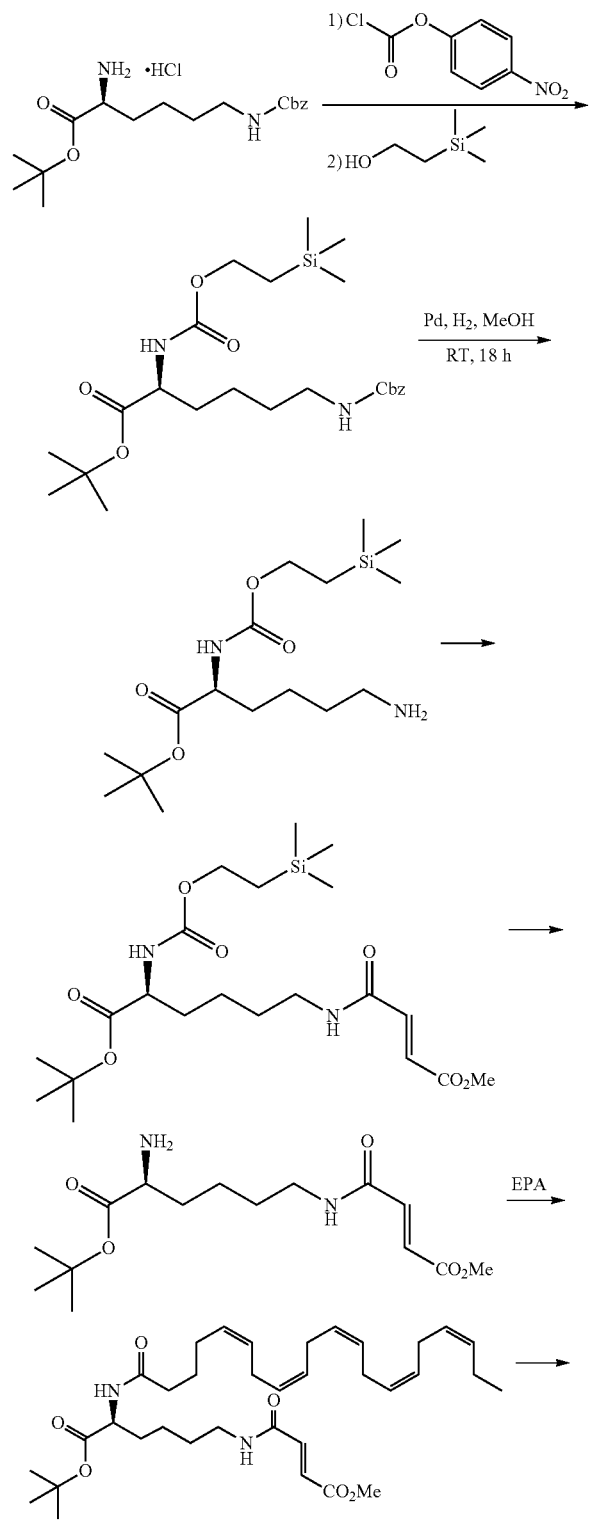

-continued

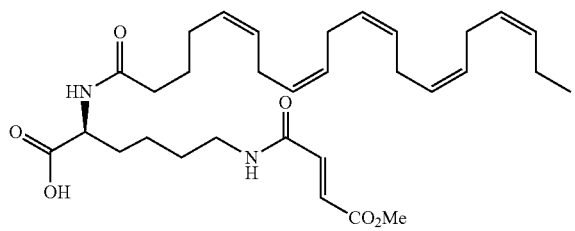

In a typical run, Cbz-Lys(OtBu) $NH_2$ hydrochloride (10 g, 26.8 mmol) was taken up in $CH_2Cl_2$ (100 mL) and treated with N-methylmorpholine (6.18 mL, 56.3 mmol). This solution was added slowly to a solution of 4-nitrophenyl chloroformate (5.66 g, 28.2 mmol) in 100 mL of $CH_2Cl_2$ at 0° C. The reaction was then allowed to warm to RT and stirred at RT overnight. After washing with saturated aqueous $NaHCO_3$ (3×100 mL), brine, the solution was dried over $Na_2SO_4$ and concentrated under reduced pressure. The residue was purified by silica gel chromatography (10% EtOAc/90% pentane) to provide the intermediate 4-nitrophenyl derivative (11 g; 81%). This intermediate 4-nitrophenyl derivative (10 g, 20 mmol) was taken up in 150 mL of anhydrous THF along with 2-(trimethylsilyl)ethanol (4.3 mL, 30 mmol) and cooled to 0° C. t-BuOK (2.9 g, 26 mmol) was then added under a blanket of argon. The mixture was stirred at room temperature overnight and then partitioned between EtOAc (300 mL) and brine (300 mL). The organic layer was washed with brine, dried over $Na_2SO_4$ and concentrated under reduced pressure. The resulting residue was purified by silica gel chromatography (gradient elution using a mixture of EtOAc/pentane) to afford (S)-tert-butyl 6-(benzyloxycarbonyl)-2-((2-(trimethylsilyl)ethoxy)carbonyl)hexanoate (4 g; 37%).

(S)-tert-Butyl 6-(benzyloxycarbonyl)-2-((2-(trimethylsilyl)ethoxy)carbonyl)hexanoate (4 g, 8.33 mmol) was taken up in 40 mL of MeOH along Pd/C (10%, 400 mg). The resulting reaction mixture was thoroughly purged with nitrogen and then stirred under 1 atm of $H_2$ at room temperature overnight. The reaction mixture was filtered through a pad of Celite and the filtrate was concentrated under reduced pressure. The resulting residue was purified by silica gel chromatography (95% $CH_2Cl_2$, 5% MeOH) to afford (S)-tert-butyl 6-amino-2-((2-(trimethylsilyl)ethoxy)carbonyl)hexanoate (2 g; 69%).

To a stirring mixture of (S)-tert-butyl 6-amino-2-((2-(trimethylsilyl)ethoxy)carbonyl)hexanoate (800 mg, 2.31 mmol), monomethyl fumarate (361 mg, 2.77 mmol), DIEA (1.1 mL, 6.93 mmol) in 10 mL acetonitrile was added HATU (1.14 g, 3.00 mmol) in one portion at 0° C. under an inert atmosphere of argon. The resulting reaction mixture was stirred at room temperature for 2 h and then concentrated under reduced pressure. The resulting residue was diluted with EtOAc (50 mL) and washed with brine, dried over $Na_2SO_4$, and concentrated under reduced pressure. Purification by silica gel chromatography (EtOAc/pentane) afforded (S,E)-tert-butyl 6-(4-methoxy-4-oxobut-2-enamido)-2-((2-(trimethylsilyl)ethoxy)carbonyl)hexanoate (900 mg, 85%).

This silylated material (900 mg, 1.97 mmol) was taken up in 15 mL of a 1M solution of tetra-n-butylammonium fluoride in THF and stirred at room temperature under an inert atmosphere of argon for 18 h. The reaction mixture was concentrated under reduced pressure to afford (S,E)-tert-butyl 2-amino-6-(4-methoxy-4-oxobut-2-enamido)hexanoate. This material was used for the next step without further purification.

The crude (S,E)-tert-butyl 2-amino-6-(4-methoxy-4-oxobut-2-enamido)hexanoate prepared above was taken up in 40 mL acetonitrile along with EPA (654 mg, 2.17 mmol), DIEA (1.6 mL, 9.85 mmol), HATU (973 mg, 2.56 mmol). The resulting reaction mixture was stirred at room temperature for 2 h and then concentrated under reduced pressure. The resulting residue was taken up in 50 mL of EtOAc and washed with water, brine. The organic layer was dried over $Na_2SO_4$ and concentrated under reduced pressure. Purification by silica gel chromatography (EtOAc/pentane) afforded (S)-tert-butyl 2-((5Z,8Z,11Z,14Z,17Z)-icosa-5,8,11,14,17-pentaenamido)-6-((E)-4-methoxy-4-oxobut-2-enamido) hexanoate (200 mg, 17% for the 2 steps).

(S)-tert-Butyl 2-((5Z,8Z,11Z,14Z,17Z)-icosa-5,8,11,14,17-pentaenamido)-6-((E)-4-methoxy-4-oxobut-2-enamido) hexanoate (200 mg, 0.334 mmol) was taken up in 3 mL of a 4 N HCl solution in dioxane and stirred at room temperature under an inert atmosphere of argon for 2 h. The reaction mixture was concentrated under reduced pressure and the resulting residue was portioned between 30 mL of EtOAc and 30 mL of water. The organic layer was further washed with brine until the pH of the water layer was close to neutral, dried over $Na_2SO_4$ and concentrated under reduced pressure. Purification by preparative HPLC using a mixture of aqueous acetonitrile that has been buffered with 0.1% TFA afforded (S)-2-((5Z,8Z,11Z,14Z,17Z)-icosa-5,8,11,14,17-pentaenamido)-6-((E)-4-methoxy-4-oxobut-2-enamido)hexanoic acid. (90 mg; 50%). MS (EI) calcd for $C_{31}H_{46}N_2O_6$: 542.34. found 543 (M+1).

Example 24

Preparation of (S)-6-((4Z,7Z,10Z,13Z,16Z,19Z)-docosa-4,7,10,13,16,19-hexaenamido)-2-((E)-4-methoxy-4-oxobut-2-enamido)hexanoic acid (I-7)

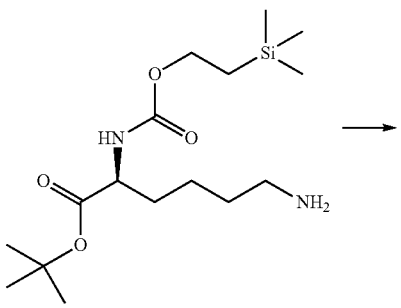

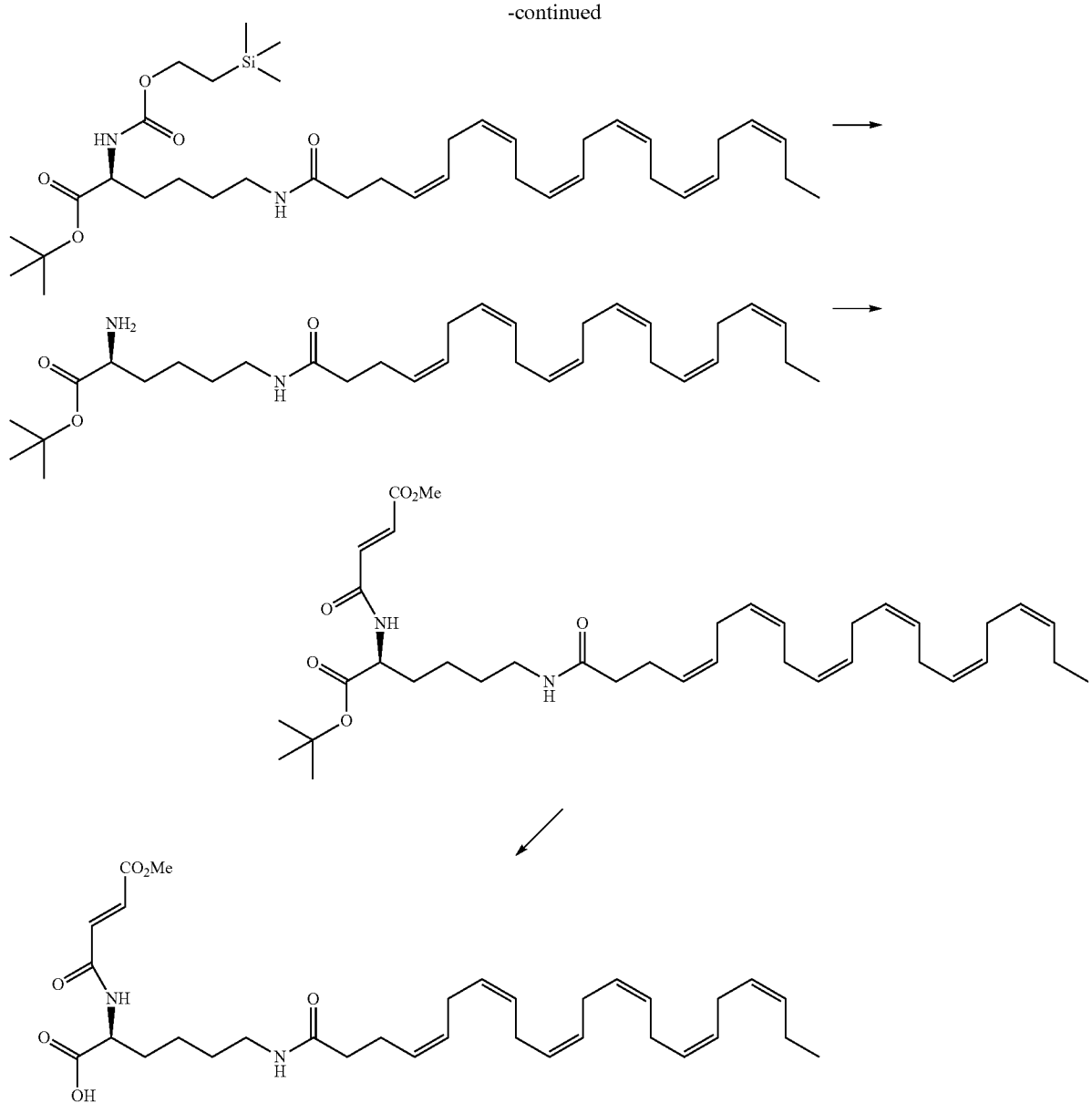

In a typical run, (S)-tert-butyl 6-amino-2-((2-(trimethylsilyl)ethoxy)carbonyl)hexanoate, (2 g, 5.78 mmol) was taken up in 30 mL of acetonitrile along with HATU (3.29 g, 8.67 mmol), DHA (2.28 g, 6.94 mmol) and DIEA (2.9 mL, 17.4 mmol). The resulting reaction mixture was stirred at room temperature under an inert atmosphere of argon for 2 h and then concentrated under reduced pressure. The resulting residue was taken up in 100 mL of EtOAc and washed with brine. The organic layer was dried over Na$_2$SO$_4$ and concentrated under reduced pressure. Purification by silica gel chromatography (EtOAc/pentane) afforded (S)-tert-butyl 6-((4Z,7Z,10Z,13Z,16Z,19Z)-docosa-4,7,10,13,16,19-hexaenamido)-2-((2-(trimethylsilyl)ethoxy)carbonyl)hexanoate (2.8 g; 80%).

(S)-tert-Butyl 6-((4Z,7Z,10Z,13Z,16Z,19Z)-docosa-4,7,10,13,16,19-hexaenamido)-2-((2-(trimethylsilyl)ethoxy)carbonyl)hexanoate (2.8 g, 4.26 mmol) was taken up in 50 mL of a 1M solution of tetra-n-butylammonium fluoride in THF and was stirred at room temperature under an inert atmosphere of argon for 18 h. The reaction mixture was concentrated under reduced pressure and the resulting crude product was used for the next step without further purification.

The crude (S)-tert-butyl 2-amino-6-((4Z,7Z,10Z,13Z,16Z,19Z)-docosa-4,7,10,13,16,19-hexaenamido)hexanoate, prepared above, was taken up in 40 mL acetonitrile along with monomethyl fumarate (610 mg, 4.69 mmol), DIEA (3.0 mL, 18.8 mmol) and HATU (2.4 g, 6.39 mmol). The resulting reaction mixture was stirred at room temperature for 2 h and then concentrated under reduced pressure. The resulting residue was taken up in 100 mL of EtOAc and washed with water and brine. The organic layer was dried over Na$_2$SO$_4$ and concentrated under reduced pressure. Purification by silica gel chromatography (EtOAc/pentane) afforded (S)-tert-butyl 6-((4Z,7Z,10Z,13Z,16Z,19Z)-docosa-4,7,10,13,16,19-hexaenamido)-2-((E)-4-methoxy-4-oxobut-2-enamido)hexanoate (500 mg, 30%).

(S)-tert-butyl 6-((4Z,7Z,10Z,13Z,16Z,19Z)-docosa-4,7,10,13,16,19-hexaenamido)-2-((E)-4-methoxy-4-oxobut-2-enamido)hexanoate (500 mg) was taken up in 6 mL of a 4 N HCl solution in dioxane and stirred at room temperature under an inert atmosphere of argon for 2 h. The reaction mixture was concentrated under reduced pressure and the resulting residue was partitioned between 30 mL of EtOAc and 30 mL of water. The organic layer was further washed with brine until the pH of the water layer was close to neutral, dried over $Na_2SO_4$ and concentrated under reduced pressure. Purification by preparative HPLC using a mixture of aqueous acetonitrile that has been buffered with 0.1% TFA afforded (S)-6-((4Z,7Z,10Z,13Z,16Z,19Z)-docosa-4,7,10,13,16,19-hexaenamido)-2-((E)-4-methoxy-4-oxobut-2-enamido)hexanoic acid (160 mg; 35%). MS (EI) calcd for $C_{33}H_{48}N_2O_6$: 568.35. found 569 (M+1).

Example 25

Preparation of (E)-methyl 4-(2-(2-(4Z,7Z,10Z,13Z,16Z,19Z)-docosa-4,7,10,13,16,19-hexaenamidoethylamino)ethylamino)-4-oxobut-2-enoate (I-24)

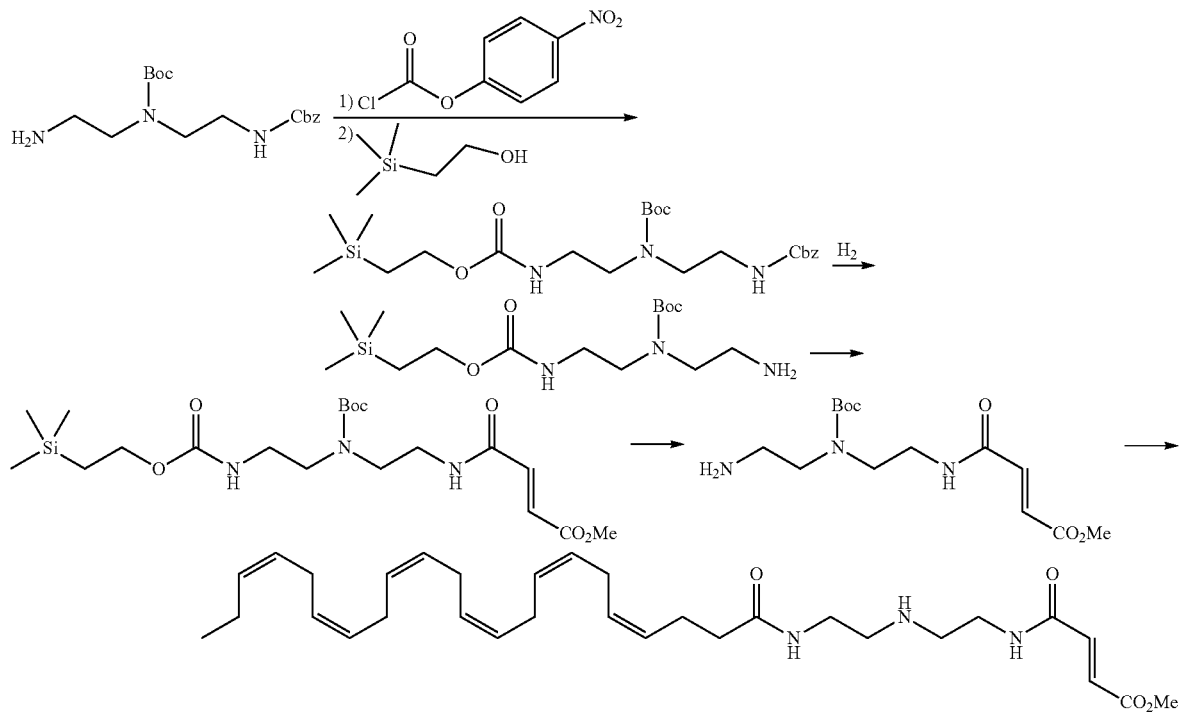

(2-Amino-ethyl)-(2-benzyloxycarbonylamino-ethyl)-carbamic acid tert-butyl ester was prepared from benzyl 2-aminoethylcarbamate using the same reaction sequence outlined by Andruszkiewicz et al in *Synthetic Communications* 2008, 38, p. 905-913 (reaction with acrylonitrile, followed by protection of the secondary amine with the BOC group, and conversion of the nitrile group to an amino group with one less methylene unit using the Hoffmann rearrangement). (2-Amino-ethyl)-(2-benzyloxycarbonylamino-ethyl)-carbamic acid tert-butyl ester (500 mg, 1.48 mmol) was taken up in 15 mL of $CH_2Cl_2$ along with 4-methylmorpholine (449 mg, 4.44 mmol) and cooled to 0° C. 4-Nitrophenyl chloroformate (328 mg, 1.63 mmol) was then added at 0° C. The resulting reaction mixture was warmed to room temperature and stirred for 16 h. It was then diluted with water. The organic layer was separated, dried ($Na_2SO_4$), and concentrated under reduced pressure. Purification by chromatography (95% $CH_2Cl_2$, 5% MeOH) afforded the intermediate nitrophenyl carbamate (480 mg; 64%).

Potassium tert-butoxide (113 mg, 1.01 mmol) was added a mixture containing the intermediate nitrophenyl carbamate (480 mg, 0.96 mmol) and 2-(trimethylsilyl)ethanol (136 mg, 1.15 mmol) in THF (10 mL) at 0° C. The resulting reaction mixture was stirred at rt for 18 h and then concentrated under reduced pressure. The resulting residue was partitioned between EtOAc and water. The organic layer was dried over $Na_2SO_4$ and concentrated under reduced pressure. Purification by silica gel chromatography (3:1 pentane/EtOAc) afforded the fully protected triamine derivative (190 mg; 41%). This fully protected triamine (190 mg, 0.40 mmol) was taken up in MeOH (5 mL) along 5% Pd/C (50 mg), and the resulting mixture was stirred under 1 atm of hydrogen at room temperature for 16 h. The reaction mixture was filtered through a pad of Celite and the clear filtrate was concentrated under reduced pressure. Purification by silica gel chromatography (9:1 $CH_2Cl_2$/MeOH) afforded (2-amino-ethyl)-[2-(2-trimethylsilanyl-ethoxycarbonylamino)-ethyl]-carbamic acid tert-butyl ester (80 mg; 58%).

(2-Amino-ethyl)-[2-(2-trimethylsilanyl-ethoxycarbonylamino)-ethyl]-carbamic acid tert-butyl ester (80 mg, 0.23 mmol) was taken up in 5 mL of acetonitrile along with mono methyl fumarate (30 mg, 0.23 mmol), DIEA (90 mg, 0.69 mmol) and HATU (105 mg, 0.28 mmol). The resulting reaction mixture was stirred at room temperature for 2 h and then concentrated under reduced pressure. The resulting residue was taken up EtOAc and washed with brine. The organic layer was dried over $Mg_2SO_4$ and then concentrated under reduced pressure. Purification by silica gel chromatography (3:1 pentane/EtOAc) afforded the desired amide derivative as an oil (80 mg; 75%). This material was taken up in 3 mL of a 4 N HCl solution in dioxane and stirred at room temperature under an inert atmosphere of argon for 1 h. The reaction mixture was concentrated under reduced pressure and the resulting residue was partitioned between 30 mL of EtOAc and 30 mL of water. The organic layer was further washed with brine until the pH of the water layer was close to neutral, dried over $Na_2SO_4$ and concentrated under reduced pressure. Purification by preparative HPLC using a mixture of aqueous acetonitrile that has been buffered with 0.1% TFA afforded (E)-methyl 4-(2-(2-(4Z,7Z,10Z,13Z,16Z,19Z)-docosa-4,7,10,13,16,19-hexaenamidoethylamino)ethylamino)-4-oxobut-2-enoate. MS (EI) calcd for $C_{31}H_{47}N_3O_4$: 525.36. found 526 (M+1).

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula I:

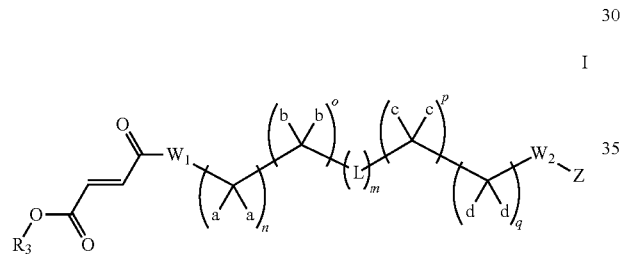

I or a pharmaceutically acceptable salt, hydrate, enantiomer, or stereoisomer thereof;
wherein
each $W_1$ and $W_2$ is independently null, O, S, NH, or NR, or $W_1$ and $W_2$ can be taken together to form an optionally substituted imidazolidine or piperazine group;
each a, b, c, and d, is independently —H, -D, —$CH_3$, —$OCH_3$, —$OCH_2CH_3$, —C(O)OR, —O—Z, or benzyl, or two of a, b, c, and d can be taken together, along with the single carbon to which they are bound, to form a cycloalkyl or heterocycle;
each n, o, p, and q is independently 0, 1, or 2;
each L is independently null, —O—, —C(O)—, —S—, —S(O)—, —S(O)$_2$—, —S—S—, —($C_1$-$C_6$ alkyl)-, —($C_3$-$C_6$ cycloalkyl)-, a heterocycle, a heteroaryl,

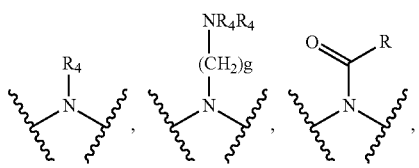

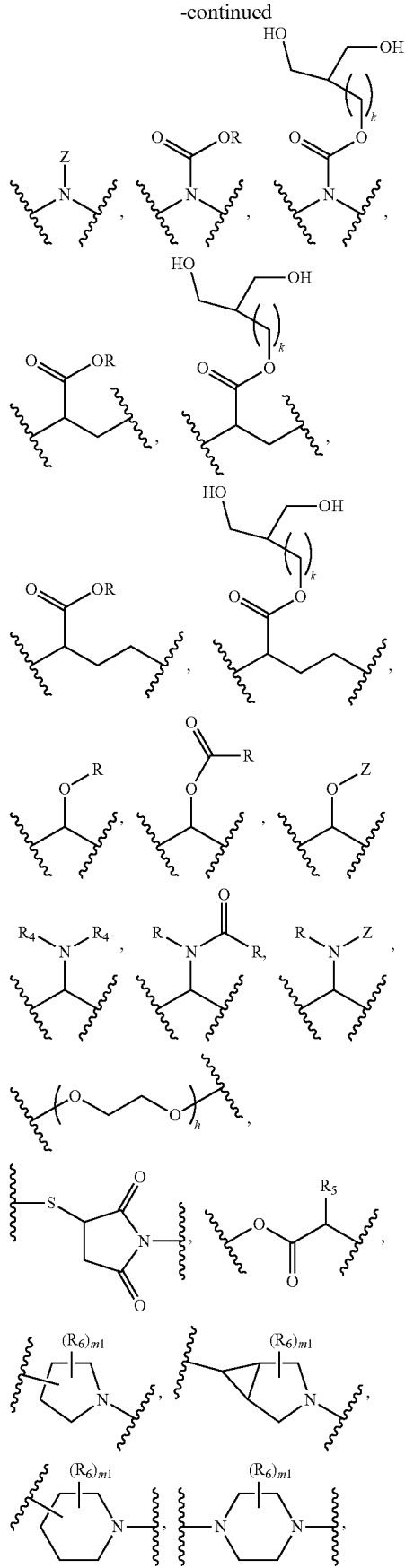

-continued

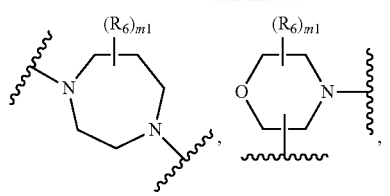

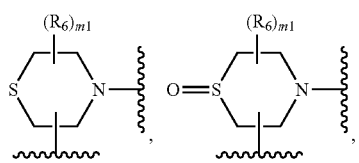

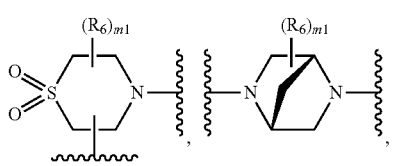

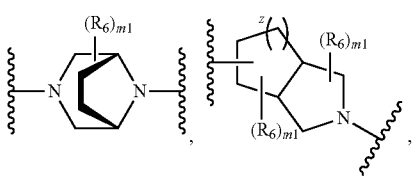

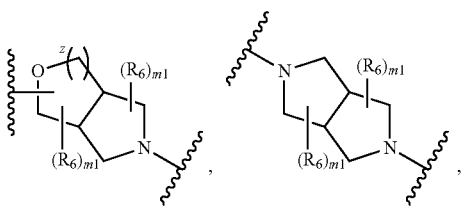

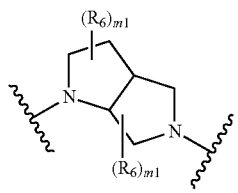

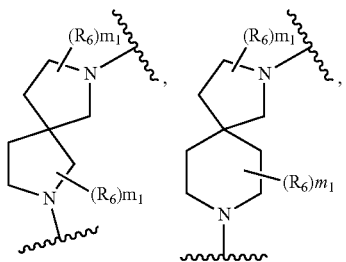

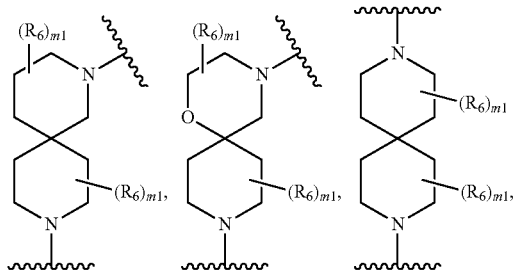

-continued

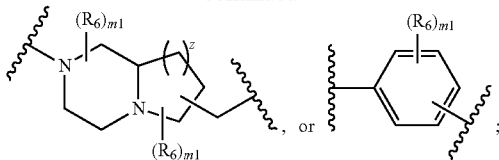

wherein the representation of L is not limited directionally left to right as is depicted, rather either the left side or the right side of L can be bound to the $W_1$ side of the compound of Formula I;

each $R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_2$-$C_3$ alkene, —$C_2$-$C_3$ alkyne, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2$$C_1$-$C_3$ alkyl;

each g is independently 2, 3, or 4;

each h is independently 1, 2, 3, or 4;

each m is independently 0, 1, 2, or 3; if m is more than 1, then L can be the same or different;

each m1 is independently 0, 1, 2, or 3;

k is 0, 1, 2, or 3;

z is 1, 2, or 3;

each $R_4$ is independently H or optionally substituted $C_1$-$C_6$ alkyl, wherein a methylene unit of the $C_1$-$C_6$ alkyl can be optionally substituted for either O or NR, and in $NR_4R_4$, both $R_4$ when taken together with the nitrogen to which they are attached can form a heterocyclic ring such as a pyrrolidine, piperidine, morpholine, piperazine or pyrrole;

each Z is independently H,

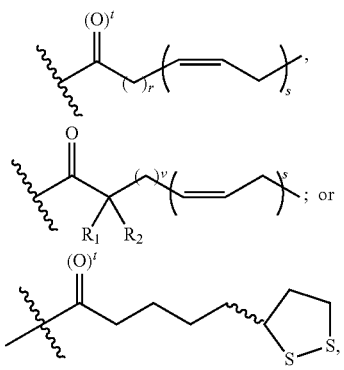

provided that
there is at least one

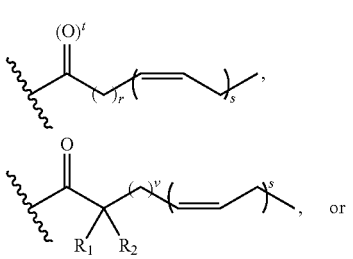

-continued

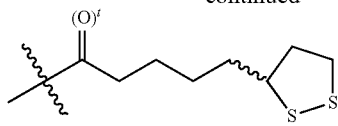

in the compound;
each t is independently 0 or 1;
each r is independently 2, 3, or 7;
each s is independently 3, 5, or 6;
each v is independently 1, 2, or 6;
each $R_1$ and $R_2$ is independently —H, -D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_2$-$C_3$ alkene, —$C_2$-$C_3$ alkyne, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2$ $C_1$-$C_3$ alkyl;
each $R_3$ is independently H, or —$C_1$-$C_6$ alkyl;
each $R_5$ is independently e, H, or straight or branched $C_1$-$C_{10}$ alkyl which can be optionally substituted with OH, $NH_2$, $CO_2R$, $CONH_2$, phenyl, $C_6H_4OH$, imidazole or arginine;
each e is independently H or any one of the side chains of the naturally occurring amino acids;
each R is independently —H, —$C_1$-$C_3$ alkyl, or straight or branched $C_1$-$C_4$ alkyl optionally substituted with OH, or halogen;
provided that
when each of m, n, o, p, and q is 0, $W_1$ and $W_2$ are each null, and Z is

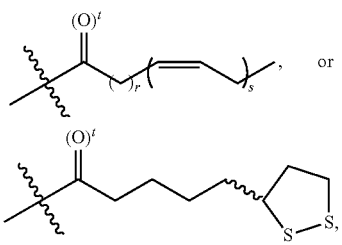

then t must be 0; and
when each of m, n, o, p, and q is 0, and $W_1$ and $W_2$ are each null, then Z must not be

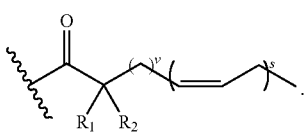

2. The compound of claim 1, wherein $W_1$ and $W_2$ are each NH.
3. The compound of claim 2, wherein Z is

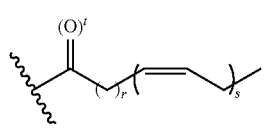

and t=1, r=2, s=6 or t=1, r=3, and s=5.

4. The compound of claim 2 selected from the group consisting of:
(E)-methyl 4-(2-(5Z,8Z,11Z,14Z,17Z)-icosa-5,8,11,14,17-pentaenamidoethylamino)-4-oxobut-2-enoate (I-2);
(S)-6-((5Z,8Z,11Z,14Z,17Z)-icosa-5,8,11,14,17-pentaenamido)-2-((E)-4-methoxy-4-oxobut-2-enamido)hexanoic acid (I-71);
(S)-1,3-dihydroxypropan-2-yl 6-((4Z,7Z,10Z,13Z,16Z,19Z)-docosa-4,7,10,13,16,19-hexaenamido)-2-((E)-4-methoxy-4-oxobut-2-enamido)hexanoate (I-8);
(S)-1,3-dihydroxypropan-2-yl 6-((5Z,8Z,11Z,14Z,17Z)-icosa-5,8,11,14,17-pentaenamido)-2-((E)-4-methoxy-4-oxobut-2-enamido)hexanoate (I-96);
(S)-2-((5Z,8Z,11Z,14Z,17Z)-icosa-5,8,11,14,17-pentaenamido)-6-((E)-4-methoxy-4-oxobut-2-enamido)hexanoic acid (I-72);
(S)-1,3-dihydroxypropan-2-yl 2-((4Z,7Z,10Z,13Z,16Z,19Z)-docosa-4,7,10,13,16,19-hexaenamido)-6-((E)-4-methoxy-4-oxobut-2-enamido)hexanoate (I-11);
(S)-1,3-dihydroxypropan-2-yl 2-((5Z,8Z,11Z,14Z,17Z)-icosa-5,8,11,14,17-pentaenamido)-6-((E)-4-methoxy-4-oxobut-2-enamido)hexanoate (I-97);
(E)-methyl 4-(2-(2-(5Z,8Z,11Z,14Z,17Z)-icosa-5,8,11,14,17-pentaenamidoethylamino)ethylamino)-4-oxobut-2-enoate (I-73);
(S)-5-((4Z,7Z,10Z,13Z,16Z,19Z)-docosa-4,7,10,13,16,19-hexaenamido)-2-((E)-4-methoxy-4-oxobut-2-enamido)pentanoic acid (I-80);
(S)-2-((4Z,7Z,10Z,13Z,16Z,19Z)-docosa-4,7,10,13,16,19-hexaenamido)-5-((E)-4-methoxy-4-oxobut-2-enamido)pentanoic acid (I-81);
(S)-1,3-dihydroxypropan-2-yl 5-((4Z,7Z,10Z,13Z,16Z,19Z)-docosa-4,7,10,13,16,19-hexaenamido)-2-((E)-4-methoxy-4-oxobut-2-enamido)pentanoate (I-82);
(S)-1,3-dihydroxypropan-2-yl 2-((4Z,7Z,10Z,13Z,16Z,19Z)-docosa-4,7,10,13,16,19-hexaenamido)-5-((E)-4-methoxy-4-oxobut-2-enamido)pentanoate (I-83);
(S)-5-((5Z,8Z,11Z,14Z,17Z)-icosa-5,8,11,14,17-pentaenamido)-2-((E)-4-methoxy-4-oxobut-2-enamido)pentanoic acid (I-84);
(S)-2-((5Z,8Z,11Z,14Z,17Z)-icosa-5,8,11,14,17-pentaenamido)-5-((E)-4-methoxy-4-oxobut-2-enamido)pentanoic acid (I-85);
(S)-1,3-dihydroxypropan-2-yl 5-((5Z,8Z,11Z,14Z,17Z)-icosa-5,8,11,14,17-pentaenamido)-2-((E)-4-methoxy-4-oxobut-2-enamido)pentanoate (I-86);
(S)-1,3-dihydroxypropan-2-yl 2-((5Z,8Z,11Z,14Z,17Z)-icosa-5,8,11,14,17-pentaenamido)-5-((E)-4-methoxy-4-oxobut-2-enamido)pentanoate (I-87);
(E)-ethyl 4-(2-(5Z,8Z,11Z,14Z,17Z)-icosa-5,8,11,14,17-pentaenamidoethylamino)-4-oxobut-2-enoate (1-75);
(S)-2-((E)-4-ethoxy-4-oxobut-2-enamido)-6-((5Z,8Z,11Z,14Z,17Z)-icosa-5,8,11,14,17-pentaenamido)hexanoic acid (I-76);
(S)-1,3-dihydroxypropan-2-yl 6-((4Z,7Z,10Z,13Z,16Z,19Z)-docosa-4,7,10,13,16,19-hexaenamido)-2-((E)-4-ethoxy-4-oxobut-2-enamido)hexanoate (I-98);
(S)-1,3-dihydroxypropan-2-yl 2-((E)-4-ethoxy-4-oxobut-2-enamido)-6-((5Z,8Z,11Z,14Z,17Z)-icosa-5,8,11,14,17-pentaenamido)hexanoate (I-99);
(S)-6-((E)-4-ethoxy-4-oxobut-2-enamido)-2-((5Z,8Z,11Z,14Z,17Z)-icosa-5,8,11,14,17-pentaenamido)hexanoic acid (I-77);
(S)-1,3-dihydroxypropan-2-yl 2-((4Z,7Z,10Z,13Z,16Z,19Z)-docosa-4,7,10,13,16,19-hexaenamido)-6-((E)-4-ethoxy-4-oxobut-2-enamido)hexanoate (I-100);

(S)-1,3-dihydroxypropan-2-yl 6-((E)-4-ethoxy-4-oxobut-2-enamido)-2-((5Z,8Z,11Z,14Z,17Z)-icosa-5,8,11,14,17-pentaenamido)hexanoate (I-101);

(E)-ethyl 4-(2-(2-(5Z,8Z,11Z,14Z,17Z)-icosa-5,8,11,14,17-pentaenamidoethylamino)ethylamino)-4-oxobut-2-enoate (I-79);

(E)-ethyl 4-(2-((2-(5Z,8Z,11Z,14Z,17Z)-icosa-5,8,11,14,17-pentaenamidoethyl)(methyl)amino)ethylamino)-4-oxobut-2-enoate (I-78);

(S)-5-((4Z,7Z,10Z,13Z,16Z,19Z)-docosa-4,7,10,13,16,19-hexaenamido)-2-((E)-4-ethoxy-4-oxobut-2-enamido)pentanoic acid (I-88);

(S)-2-((4Z,7Z,10Z,13Z,16Z,19Z)-docosa-4,7,10,13,16,19-hexaenamido)-5-((E)-4-ethoxy-4-oxobut-2-enamido)pentanoic acid (I-89);

(S)-1,3-dihydroxypropan-2-yl 5-((4Z,7Z,10Z,13Z,16Z,19Z)-docosa-4,7,10,13,16,19-hexaenamido)-2-((E)-4-ethoxy-4-oxobut-2-enamido)pentanoate (I-90);

(S)-1,3-dihydroxypropan-2-yl 2-((4Z,7Z,10Z,13Z,16Z,19Z)-docosa-4,7,10,13,16,19-hexaenamido)-5-((E)-4-ethoxy-4-oxobut-2-enamido)pentanoate (I-91);

(S)-2-((E)-4-ethoxy-4-oxobut-2-enamido)-5-((5Z,8Z,11Z,14Z,17Z)-icosa-5,8,11,14,17-pentaenamido)pentanoic acid (I-92);

(S)-5-((E)-4-ethoxy-4-oxobut-2-enamido)-2-((5Z,8Z,11Z,14Z,17Z)-icosa-5,8,11,14,17-pentaenamido)pentanoic acid (I-93);

(S)-1,3-dihydroxypropan-2-yl 2-((E)-4-ethoxy-4-oxobut-2-enamido)-5-((5Z,8Z,11Z,14Z,17Z)-icosa-5,8,11,14,17-pentaenamido)pentanoate (I-94); and (S)-1,3-dihydroxypropan-2-yl 5-((E)-4-ethoxy-4-oxobut-2-enamido)-2-((5Z,8Z,11Z,14Z,17Z)-icosa-5,8,11,14,17-pentaenamido)pentanoate (I-95).

5. The compound of claim 2 having the Formula IA:

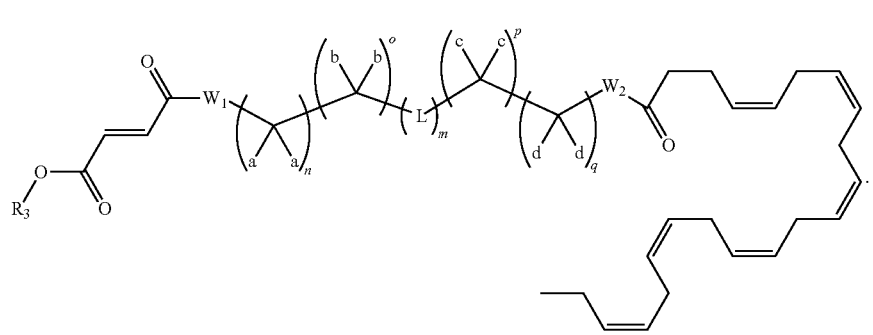

IA

6. The compound of claim 5 selected from the group consisting of

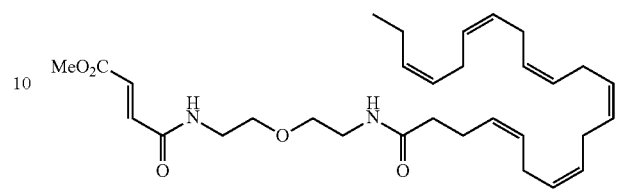

(E)-methyl 4-(2-(2-(4Z,7Z,10Z,13Z,16Z,19Z)-docosa-4,7,10,13,16,19-hexaenamidoethoxy)ethylamino)-4-oxobut-2-enoate (I-3);

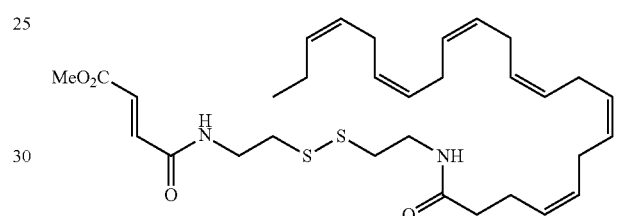

(E)-methyl 4-(2-(2-(2-(4Z,7Z,10Z,13Z,16Z,19Z)-docosa-4,7,10,13,16,19-hexaenamidoethyl)disulfanyl)ethylamino)-4-oxobut-2-enoate (I-5);

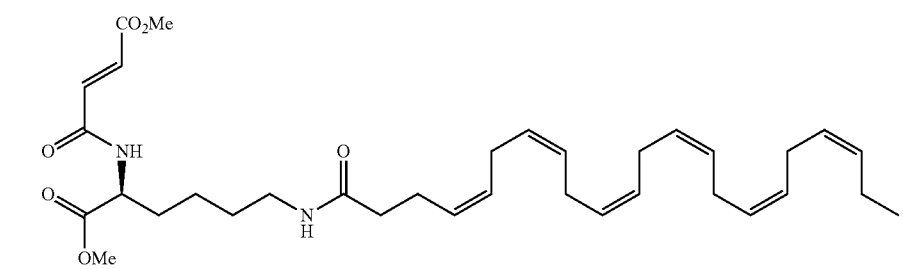 [SMILES: CC/C=C\C/C=C\C/C=C\C/C=C\C/C=C\C/C=C\CCC(=O)NCCCC[C@H](NC(=O)/C=C/C(=O)OC)C(=O)OC]

(S)-methyl 6-((4Z,7Z,10Z,13Z,16Z,19Z)-docosa-4,7,10,
13,16,19-hexaenamido)-2-((E)-4-methoxy-4-oxobut-
2-enamido)hexanoate (I-6);
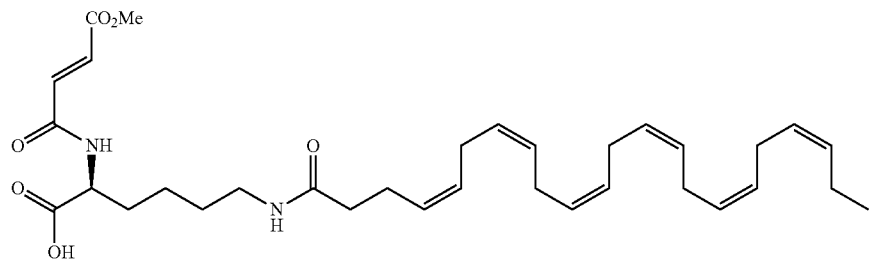
(S)-6-((4Z,7Z,10Z,13Z,16Z,19Z)-docosa-4,7,10,13,16,
19-hexaenamido)-2-((E)-4-methoxy-4-oxobut-2-ena-
mido)hexanoic acid (I-7);
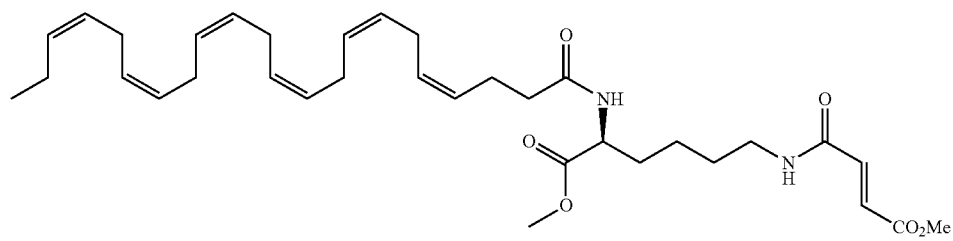 [SMILES: CC/C=C\C/C=C\C/C=C\C/C=C\C/C=C\C/C=C\CCC(=O)N[C@@H](CCCCNC(=O)/C=C/C(=O)OC)C(=O)OC]
(S)-methyl 2-((4Z,7Z,10Z,13Z,16Z,19Z)-docosa-4,7,10,
13,16,19-hexaenamido)-6-((E)-4-methoxy-4-oxobut-
2-enamido)hexanoate (I-9);
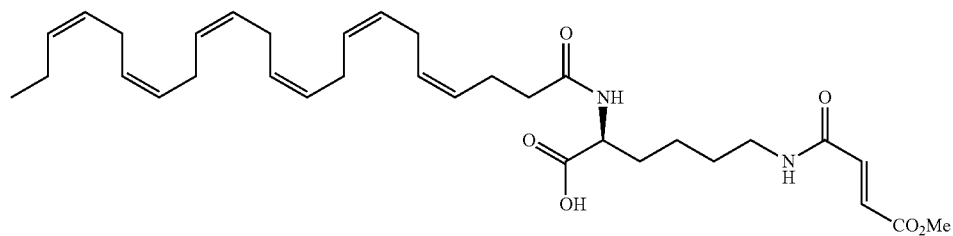 [SMILES: CC/C=C\C/C=C\C/C=C\C/C=C\C/C=C\C/C=C\CCC(=O)N[C@@H](CCCCNC(=O)/C=C/C(=O)OC)C(=O)O]
(S)-2-((4Z,7Z,10Z,13Z,16Z,19Z)-docosa-4,7,10,13,16,
19-hexaenamido)-6-((E)-4-methoxy-4-oxobut-2-ena-
mido)hexanoic acid (1-10);
(E)-methyl 4-((3-((4Z,7Z,10Z,13Z,16Z,19Z)-docosa-4,7,
10,13,16,19-hexaenamido)propyl)amino)-4-oxobut-2-
enoate (I-21);

(E)-methyl 4-(1-(4Z,7Z,10Z,13Z,16Z,19Z)-docosa-4,7,10,13,16,19-hexaenamido-2-methylpropan-2-ylamino)-4-oxobut-2-enoate (I-22);

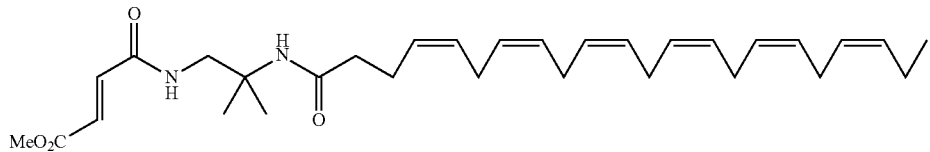 [SMILES: CC/C=C\C/C=C\C/C=C\C/C=C\C/C=C\C/C=C\CCC(=O)NC(C)(C)CNC(=O)/C=C/C(=O)OC]

(E)-methyl 4-(2-(4Z,7Z,10Z,13Z,16Z,19Z)-docosa-4,7,10,13,16,19-hexaenamido-2-methylpropylamino)-4-oxobut-2-enoate (I-23);

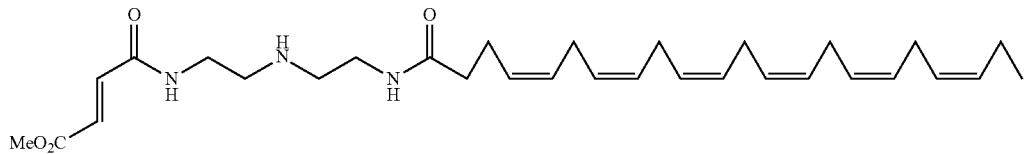 [SMILES: CC/C=C\C/C=C\C/C=C\C/C=C\C/C=C\C/C=C\CCC(=O)NCCNCCNC(=O)/C=C/C(=O)OC]

(E)-methyl 4-(2-(2-(4Z,7Z,10Z,13Z,16Z,19Z)-docosa-4,7,10,13,16,19-hexaenamidoethylamino)ethylamino)-4-oxobut-2-enoate (I-24);

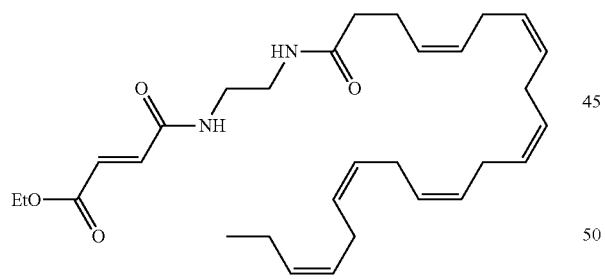

(E)-ethyl 4-(2-(4Z,7Z,10Z,13Z,16Z,19Z)-docosa-4,7,10,13,16,19-hexaenamidoethylamino)-4-oxobut-2-enoate (I-66);

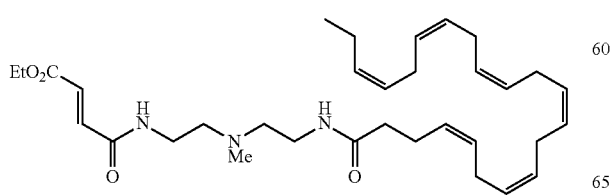

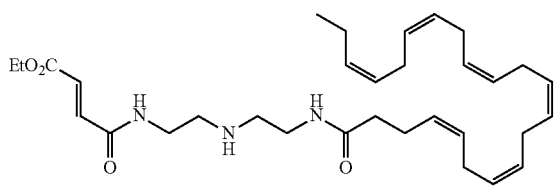 [SMILES: CC/C=C\C/C=C\C/C=C\C/C=C\C/C=C\C/C=C\CCC(=O)NCCNCCNC(=O)/C=C/C(=O)OCC]

(E)-ethyl 4-(2((2-(4Z,7Z,10Z,13Z,16Z,19Z)-docosa-4,7,10,13,16,19-hexaenamidoethyl)(methyl)amino)ethylamino)-4-oxobut-2-enoate (I-67);

(E)-ethyl 4-(2-(2-(4Z,7Z,10Z,13Z,16Z,19Z)-docosa-4,7,10,13,16,19-hexaenamidoethylamino)ethylamino)-4-oxobut-2-enoate (I-68);

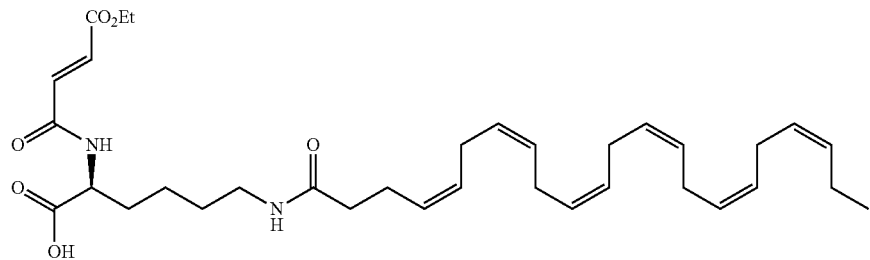 [SMILES: CC/C=C\C/C=C\C/C=C\C/C=C\C/C=C\C/C=C\CCC(=O)NCCCC[C@H](NC(=O)/C=C/C(=O)OCC)C(=O)O]

(S)-6-((4Z,7Z,10Z,13Z,16Z,19Z)-docosa-4,7,10,13,16,19-hexaenamido)-2-((E)-4-ethoxy-4-oxobut-2-enamido)hexanoic acid (I-69); and

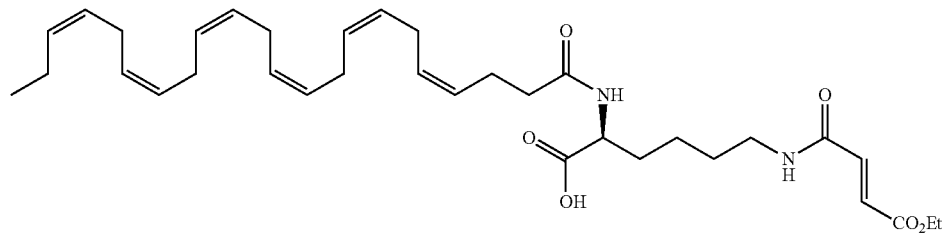 [SMILES: CC/C=C\C/C=C\C/C=C\C/C=C\C/C=C\C/C=C\CCC(=O)N[C@@H](CCCCNC(=O)/C=C/C(=O)OCC)C(=O)O]

(S)-2-((4Z,7Z,10Z,13Z,16Z,19Z)-docosa-4,7,10,13,16,19-hexaenamido)-6-((E)-4-ethoxy-4-oxobut-2-enamido)hexanoic acid (I-70).

7. The compound of claim 6 having the structure:

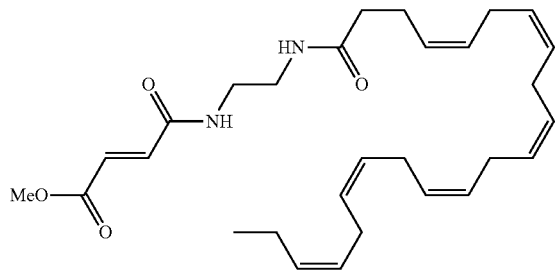

(E)-methyl 4-(2-(4Z,7Z,10Z,13Z,16Z,19Z)-docosa-4,7,10,13,16,19-hexaenamidoethylamino)-4-oxobut-2-enoate (I-1).

8. The compound of claim 6 having the structure:

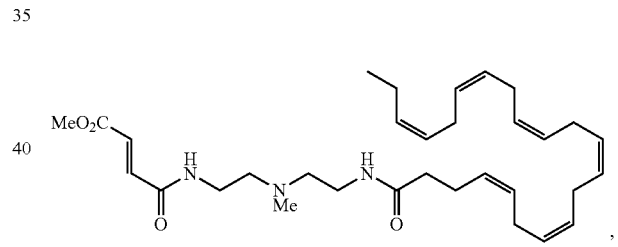

(E)-methyl 4-(2((2-(4Z,7Z,10Z,13Z,16Z,19Z)-docosa-4,7,10,13,16,19-hexaenamidoethyl)(methyl)amino)ethylamino)-4-oxobut-2-enoate (I-4).

9. The compound of claim 2 having the structure:

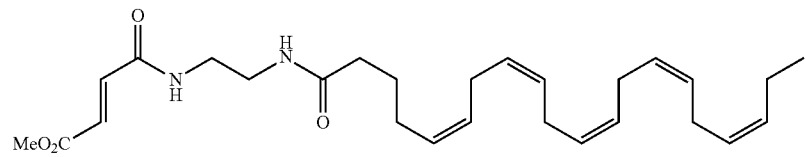 [SMILES: CC/C=C\C/C=C\C/C=C\C/C=C\C/C=C\CCCC(=O)NCCNC(=O)/C=C/C(=O)OC]

(E)-methyl 4-(2-(5Z,8Z,11Z,14Z,17Z)-icosa-5,8,11,14,17-pentaenamidoethylamino)-4-oxobut-2-enoate (I-2).

10. The compound of claim 2 having the structure:

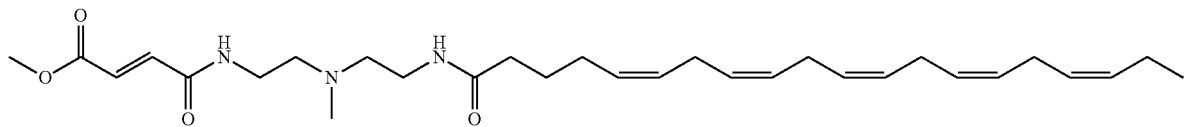 [SMILES: CC/C=C\C/C=C\C/C=C\C/C=C\C/C=C\CCCC(=O)NCCN(C)CCNC(=O)/C=C/C(=O)OC]

(E)-methyl 4-(2-((2-(5Z,8Z,11Z,14Z,17Z)-icosa-5,8,11,14,17-pentaenamidoethyl)(methyl)amino)ethylamino)-4-oxobut-2-enoate (I-74).

11. A pharmaceutical composition comprising a compound of claim 2 and a pharmaceutically acceptable carrier.

12. The pharmaceutical composition of claim 11, wherein the compound is of Formula IA

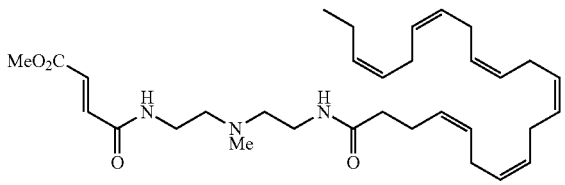

IA

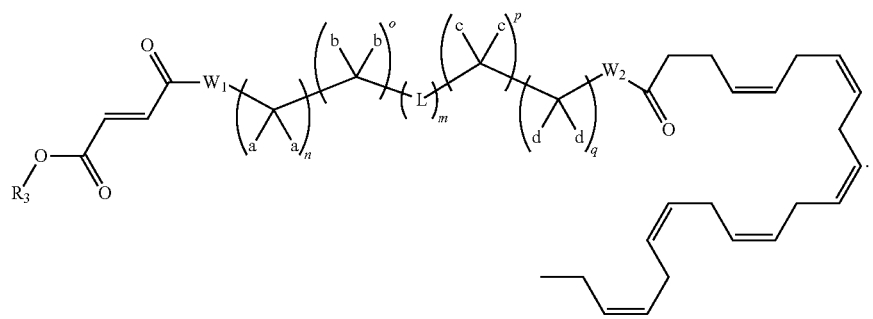

13. The pharmaceutical composition of claim 12, wherein the compound is

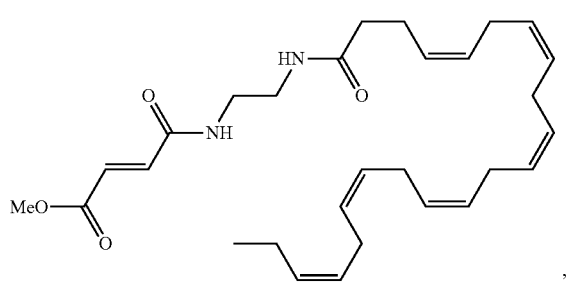 [SMILES: CC/C=C\C/C=C\C/C=C\C/C=C\C/C=C\C/C=C\CCC(=O)NCCNC(=O)/C=C/C(=O)OC]

(E)-methyl 4-(2-(4Z,7Z,10Z,13Z,16Z,19Z)-docosa-4,7,10,13,16,19-hexaenamidoethylamino)-4-oxobut-2-enoate (I-1).

14. The pharmaceutical composition of claim 12, wherein the compound is (E)-methyl 4-(2((2-(4Z,7Z,10Z,13Z,16Z,19Z)-docosa-4,7,10,13,16,19-hexaenamidoethyl)(methyl)amino)ethylamino)-4-oxobut-2-enoate (I-4).

15. A method of treating inflammation or an inflammatory disease, comprising administering to a patient in need thereof, an effective amount of a compound of claim 1.

16. The method of claim 15, wherein the inflammatory disease is associated with a metabolic disorder.

17. The method of claim 16, wherein the metabolic disorder is Type II diabetes, insulin resistance cardiovascular disease, arrhythmia, atherosclerosis, coronary artery disease, hypertriglyceridemia, dyslipidemia, retinopathy, neuropathy, macular edema, diabetic nephropathy, IgA nephropathy, chronic kidney disease (CKD), inflammatory diseases of the kidney including uremic complications, glomerulonephritis and nephrosis.

18. The method of claim 15, wherein the compound of Formula I is a compound of Formula IA

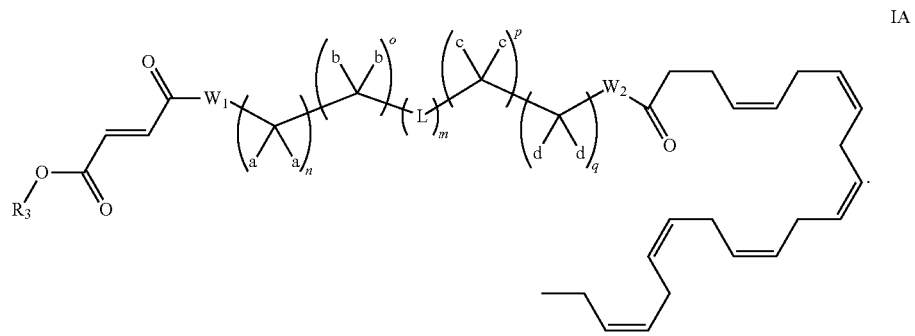

IA

19. The method of claim 15, wherein the inflammatory disease is cystic fibrosis, asthma, sclerodermatitis, psoriasis or eczema.

20. The method of claim 19, wherein the inflammatory disease is psoriasis.

21. The method of claim 20, wherein the compound is

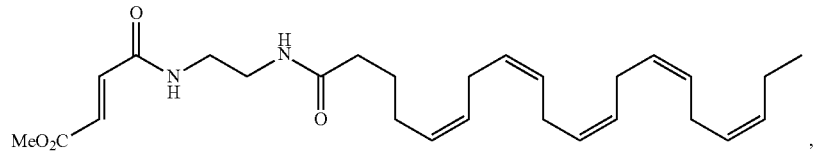 [SMILES: CC/C=C\C/C=C\C/C=C\C/C=C\C/C=C\CCCC(=O)NCCNC(=O)/C=C/C(=O)OC]

(E)-methyl 4-(2-(5Z,8Z,11Z,14Z,17Z)-icosa-5,8,11,14,17-pentaenamidoethylamino)-4-oxobut-2-enoate (I-2).

22. The method of claim 20, wherein the compound is

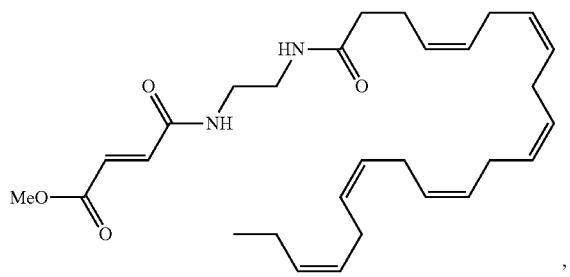 [SMILES: CC/C=C\C/C=C\C/C=C\C/C=C\C/C=C\C/C=C\CCC(=O)NCCNC(=O)/C=C/C(=O)OC]

(E)-methyl 4-(2-(4Z,7Z,10Z,13Z,16Z,19Z)-docosa-4,7,10,13,16,19-hexaenamidoethylamino)-4-oxobut-2-enoate (I-1).

23. The method of claim 20, wherein the compound is

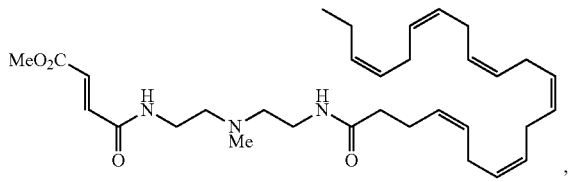 [SMILES: CC/C=C\C/C=C\C/C=C\C/C=C\C/C=C\C/C=C\CCC(=O)NCCN(C)CCNC(=O)/C=C/C(=O)OC]

(E)-methyl 4-(2-((2-(4Z,7Z,10Z,13Z,16Z,19Z)-docosa-4,7,10,13,16,19-hexaenamidoethyl)(methyl)amino)ethylamino)-4-oxobut-2-enoate (I-4).

24. The method of claim 15, wherein the disease is an inflammatory disease of the central nervous system.

25. The method of claim 24, wherein the inflammatory disease of the central nervous system is multiple sclerosis, Parkinson's disease, Huntington's disease, amyotrophic lateral sclerosis (ALS), or Alzheimer's disease.

26. The method of claim 25, wherein the inflammatory disease of the central nervous system is multiple sclerosis.

27. The method of claim 26, wherein the compound is

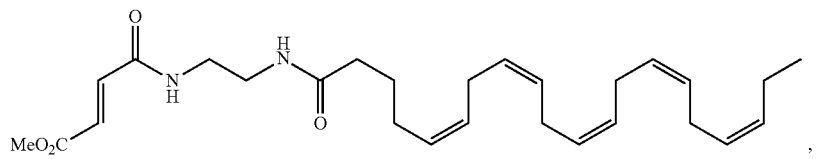 [SMILES: CC/C=C\C/C=C\C/C=C\C/C=C\C/C=C\CCCC(=O)NCCNC(=O)/C=C/C(=O)OC]

(E)-methyl 4-(2-(5Z,8Z,11Z,14Z,17Z)-icosa-5,8,11,14,17-pentaenamidoethylamino)-4-oxobut-2-enoate (I-2).

28. The method of claim 27, wherein the compound is (E)-methyl 4-(2-(4Z,7Z,10Z,13Z,16Z,19Z)-docosa-4,7,10,13,16,19-hexaenamidoethylamino)-4-oxobut-2-enoate (I-1).

29. The method of claim 27, wherein the compound is

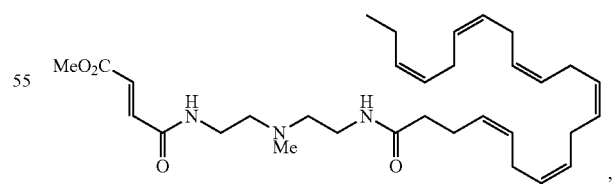

(E)-methyl 4-(2-((2-(4Z,7Z,10Z,13Z,16Z,19Z)-docosa-4,7,10,13,16,19-hexaenamidoethyl)(methyl)amino)ethylamino)-4-oxobut-2-enoate (I-4).

30. A method of treating muscular dystrophy, comprising administering to a patient in need thereof, an effective amount of a compound of claim 1.

31. The method of claim 30, wherein the compound is
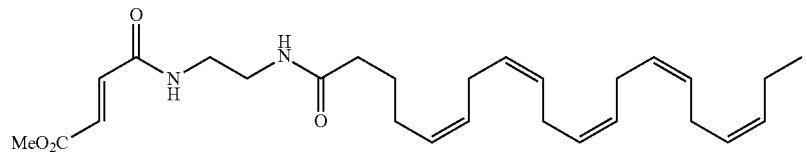 [SMILES: CC/C=C\C/C=C\C/C=C\C/C=C\C/C=C\CCCC(=O)NCCNC(=O)/C=C/C(=O)OC]
(E)-methyl 4-(2-(5Z,8Z,11Z,14Z,17Z)-icosa-5,8,11,14,17-pentaenamidoethylamino)-4-oxobut-2-enoate (I-2).
32. The method of claim 30, wherein the compound is
33. The method of claim 30, wherein the compound is
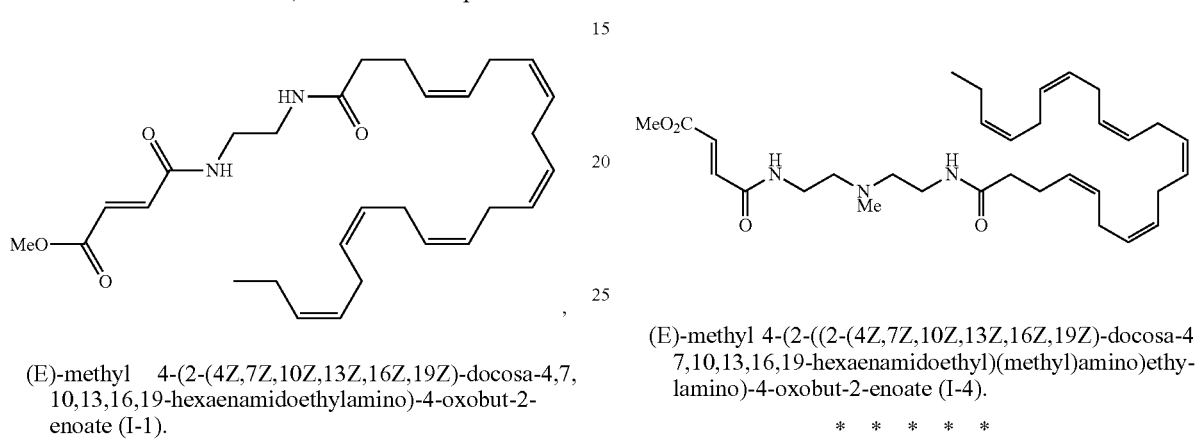
(E)-methyl 4-(2-(4Z,7Z,10Z,13Z,16Z,19Z)-docosa-4,7,10,13,16,19-hexaenamidoethylamino)-4-oxobut-2-enoate (I-1).
(E)-methyl 4-(2-((2-(4Z,7Z,10Z,13Z,16Z,19Z)-docosa-4,7,10,13,16,19-hexaenamidoethyl)(methyl)amino)ethylamino)-4-oxobut-2-enoate (I-4).
\* \* \* \* \*

UNITED STATES PATENT AND TRADEMARK OFFICE
CERTIFICATE OF CORRECTION

PATENT NO. : 8,969,354 B2
APPLICATION NO. : 13/673588
DATED : March 3, 2015
INVENTOR(S) : Jill C. Milne et al.

It is certified that error appears in the above-identified patent and that said Letters Patent is hereby corrected as shown below:

In the specification

At column 3, lines 30-38, replace

"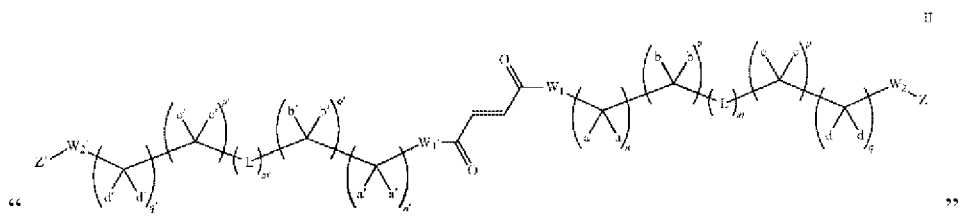"

with

-- 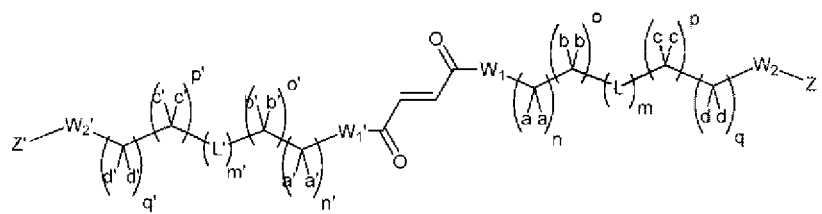 II --.

At column 5, lines 1-11, replace " 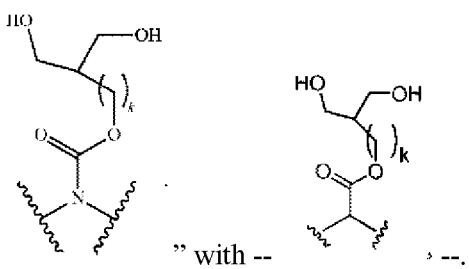 " with -- , --.

Signed and Sealed this
Twenty-fourth Day of November, 2015

Michelle K. Lee
*Director of the United States Patent and Trademark Office*

CERTIFICATE OF CORRECTION (continued)
U.S. Pat. No. 8,969,354 B2

At column 6, lines 30-35, replace " 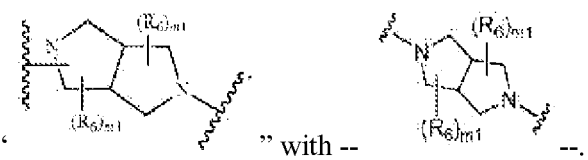 " with -- --.

At column 9, lines 45-54, replace " 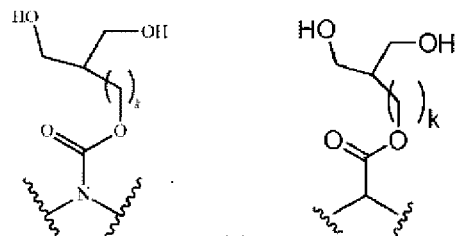 " with -- , --.

At column 10, lines 60-65, replace " 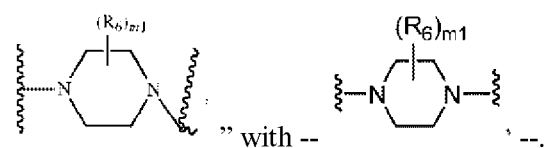 " with -- , --.

At column 11, lines 26-32, replace " 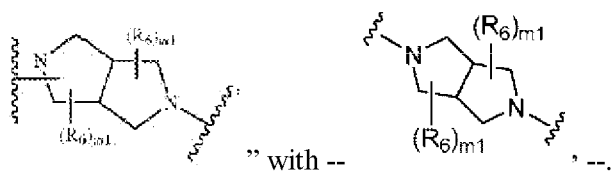 " with -- , --.

At column 12, lines 8-13, delete " 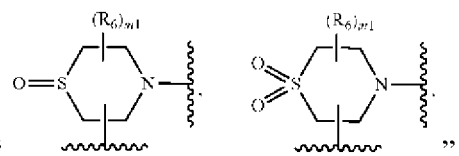 ".

At column 23, lines 54-67, replace

" 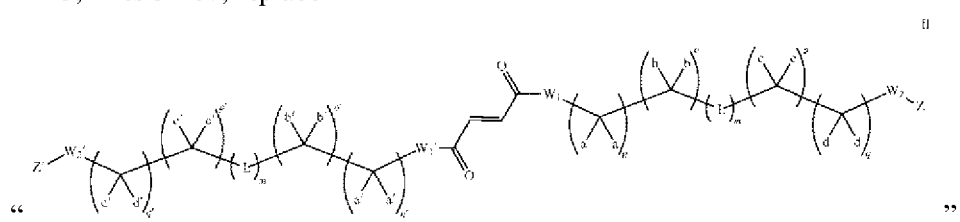 "

with

-- 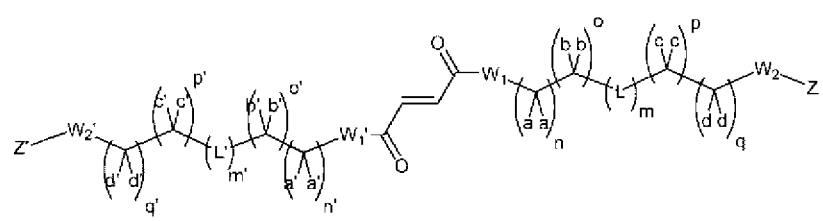 --.

At column 28, line 30, replace "$W_t$ is O" with -- $W_1$ is O --.

At column 31, line 61, replace "and s are 6" with -- and s is 6 --.

At column 31, line 62, replace "and s are 5" with -- and s is 5 --.

At column 32, lines 23-24, replace "k is O" with -- k is 0 --.

At column 42, line 39, replace "100Z" with -- 10Z --.

At column 47, lines 28-51, replace Scheme 1 with the following:

Scheme 1

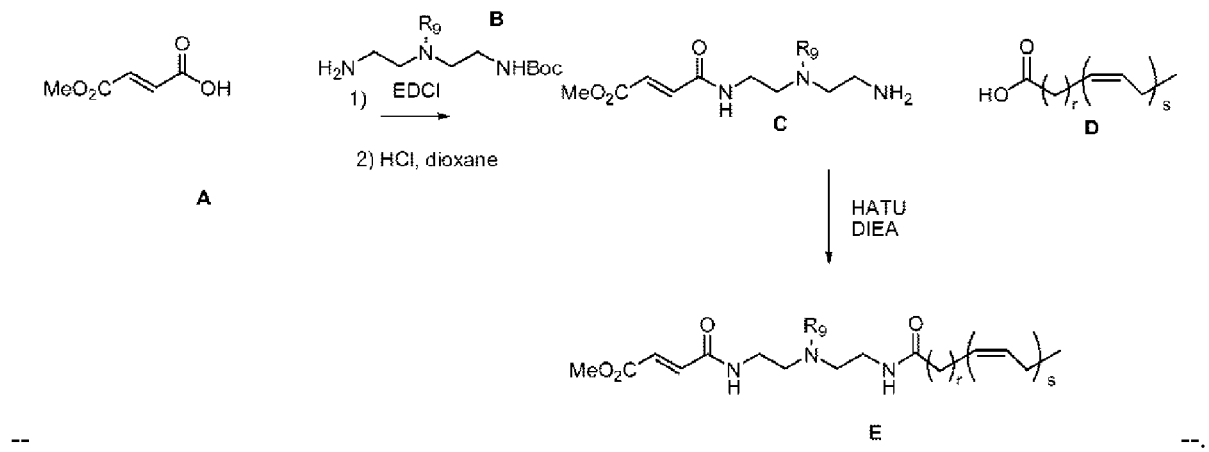

--                                                                                         --.

At column 62, line 67, replace "100.M" with -- 100μM --.

At column 63, line 3, replace "10M" with -- 10μM --.

At column 63, line 4, replace "10M" with -- 10μM --.

At column 63, line 33, add a -- . -- after "TNFα".

At column 63, line 54, replace "10 M" with -- 10μM --.

At column 63, line 63, replace "25 l" with -- 25μl --.

CERTIFICATE OF CORRECTION (continued)

In the claims

In claim 1 at column 88, lines 1-11, replace

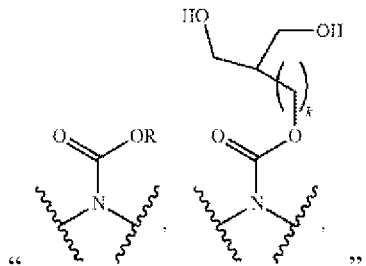

" "

with

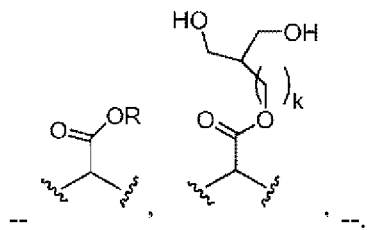

-- , --.

In claim 1 at column 91, line 21, replace "H, or" with -- H or --.

In claim 3 at column 91, line 58, replace "claim 2" with -- claim 1 --.

In claim 4 at column 92, line 1, replace "claim 2" with -- claim 1 --.

In claim 5 at column 93, line 34, replace "claim 2" with -- claim 1 --.

At column 99, line 36, delete "<".

In claim 7 at column 99, line 37, replace "claim 6" with -- claim 5 --.

In claim 8 at column 100, line 33, replace "claim 6" with -- claim 5 --.

In claim 9 at column 100, line 53, replace "claim 2" with -- claim 1 --.

In claim 10 at column 101, line 1, replace "claim 2" with -- claim 1 --.

In claim 11 at column 101, line 15, replace "claim 2" with -- claim 1 --.

In claim 13 at column 101, line 32, replace "claim 12" with -- claim 11 --.

In claim 14 at column 101, line 50, replace "claim 12" with -- claim 11 --.

In claim 17 at column 102, lines 42-43, replace "insulin resistance cardiovascular disease" with -- insulin resistance, cardiovascular disease --.

CERTIFICATE OF CORRECTION (continued)
U.S. Pat. No. 8,969,354 B2

In claim 17 at column 102, line 46, replace "(CKD), inflammatory diseases" with -- (CKD), or inflammatory diseases --.

In claim 28 at column 104, line 31, replace "claim 27" with -- claim 26 --.

In claim 29 at column 104, line 49, replace "claim 27" with -- claim 26 --.